United States Patent
Niikura et al.

(10) Patent No.: US 10,716,289 B2
(45) Date of Patent: Jul. 21, 2020

(54) SIGNAL TRANSMISSION DEVICE AND MANAGEMENT SYSTEM

(71) Applicant: Sony Corporation, Tokyo (JP)

(72) Inventors: Hideo Niikura, Tokyo (JP); Masakazu Yajima, Kanagawa (JP); Junya Matsui, Kanagawa (JP); Tamotsu Kiyakawauchi, Aichi (JP); Hiromitsu Komatsu, Kanagawa (JP); Chisako Kajihara, Tokyo (JP); Shingo Seto, Kanagawa (JP); Nobuharu Murashima, Tokyo (JP); Masaaki Masuda, Tokyo (JP)

(73) Assignee: Sony Corporation, Tokyo (JP)

( * ) Notice: Subject to any disclaimer, the term of this patent is extended or adjusted under 35 U.S.C. 154(b) by 71 days.

(21) Appl. No.: 16/093,222

(22) PCT Filed: Mar. 8, 2017

(86) PCT No.: PCT/JP2017/009187
§ 371 (c)(1),
(2) Date: Oct. 12, 2018

(87) PCT Pub. No.: WO2017/183344
PCT Pub. Date: Oct. 26, 2017

(65) Prior Publication Data
US 2019/0380306 A1    Dec. 19, 2019

(30) Foreign Application Priority Data

Apr. 21, 2016    (JP) .................................. 2016-085248

(51) Int. Cl.
*A01K 11/00* (2006.01)
*H02S 10/10* (2014.01)
(Continued)

(52) U.S. Cl.
CPC .......... *A01K 11/008* (2013.01); *A01K 11/004* (2013.01); *A01K 29/005* (2013.01);
(Continued)

(58) Field of Classification Search
CPC combination set(s) only.
See application file for complete search history.

(56) References Cited

U.S. PATENT DOCUMENTS

| 10,212,922 B2 | 2/2019 | Yajima et al. |
| 2011/0221578 A1 | 9/2011 | Sekiguchi et al. |

(Continued)

FOREIGN PATENT DOCUMENTS

| EP | 2 330 539 A1 | 6/2011 |
| EP | 2 899 526 A1 | 7/2015 |

(Continued)

OTHER PUBLICATIONS

International Written Opinion and English translation thereof dated Jun. 13, 2017 in connection with International Application No. PCT/JP2017/009187.

(Continued)

*Primary Examiner* — Travis R Hunnings
(74) *Attorney, Agent, or Firm* — Wolf, Greenfield & Sacks, P.C.

(57) ABSTRACT

[Object] To provide a signal transmission device and management system which are capable of transmitting a signal including information of an attachment target or information of the surrounding of an attachment target.
[Solution] A management system includes: a signal transmission device which includes a housing that is attached to an object to be managed in a predetermined direction, a first optical power generation unit and a second optical power generation unit that have light receiving units on a first surface and a second surface facing outwardly in a prede- (Continued)

termined direction, respectively, a first temperature sensor and a second temperature sensor that have thermal contacts on the first surface and the second surface, respectively, a communication control unit for transmitting a signal including temperature information detected by the first temperature sensor and the second temperature sensor using power generated by at least one of the first optical power generation unit and the second optical power generation unit; and an information processing device which has a control unit for receiving a signal transmitted from the signal transmission device and outputting the state information of an object to be managed to which the signal transmission device is attached on the basis of the temperature information detected by at least the first temperature sensor and the second temperature sensor.

31 Claims, 31 Drawing Sheets

(51) Int. Cl.
*A01K 29/00* (2006.01)
*H01Q 1/27* (2006.01)
*H02N 2/18* (2006.01)

(52) U.S. Cl.
CPC ............. *H01Q 1/273* (2013.01); *H02N 2/186* (2013.01); *H02S 10/10* (2014.12)

(56) References Cited

U.S. PATENT DOCUMENTS

| | | | |
|---|---|---|---|
| 2015/0057963 A1 | 2/2015 | Zakharov et al. | |
| 2015/0247777 A1 | 9/2015 | Kondou | |
| 2016/0359325 A1 | 12/2016 | Kawata et al. | |
| 2018/0242515 A1 | 8/2018 | Yajima et al. | |
| 2018/0279583 A1 | 10/2018 | Yajima et al. | |
| 2018/0295809 A1 | 10/2018 | Yajima et al. | |
| 2019/0116764 A1* | 4/2019 | Komatsu | A01K 29/00 |
| 2019/0133087 A1 | 5/2019 | Yajima et al. | |
| 2019/0163941 A1* | 5/2019 | Niikura | H04B 1/04 |
| 2019/0183436 A1* | 6/2019 | Yajima | A61B 5/0022 |

FOREIGN PATENT DOCUMENTS

| | | |
|---|---|---|
| EP | 3 104 494 A1 | 12/2016 |
| JP | 2000-149625 A | 5/2000 |
| JP | 2004-008471 A | 1/2004 |
| JP | 2004-298020 A | 10/2004 |
| JP | 2007-124966 A | 5/2007 |
| JP | 2007-319505 A | 12/2007 |
| JP | 2008-073005 A | 4/2008 |
| JP | 2009-222543 A | 10/2009 |
| JP | 2010-067086 A | 3/2010 |
| JP | 3160909 U | 7/2010 |
| JP | 2014-219341 A | 11/2014 |
| WO | WO 2009/014034 A1 | 1/2009 |
| WO | WO 2011/121753 A1 | 10/2011 |
| WO | WO 2015/025311 A1 | 2/2015 |
| WO | WO 2015/115663 A1 | 8/2015 |

OTHER PUBLICATIONS

International Preliminary Report on Patentability and English translation thereof dated Nov. 1, 2018 in connection with International Application No. PCT/JP2017/009187.

International Search Report and English translation thereof dated Jun. 13, 2017 in connection with International Application No. PCT/JP2017/009187.

* cited by examiner

FIG. 22

| ITEM | CONTENT |
|---|---|
| HARDWARE VERSION INFORMATION | 001 |
| SOFTWARE VERSION INFORMATION | 003 |
| IDENTIFICATION INFORMATION | 110001 |
| RECEPTION AVAILABILITY CONTROL INFORMATION | 0/31 |
| TRANSMISSION AVAILABILITY CONTROL INFORMATION | 0/31 |
| DESTINATION INFORMATION | 110003 |

FIG. 24

| CONTENT |
|---|
| DATA FORMAT INFORMATION OF SIGNAL |
| IDENTIFICATION INFORMATION OF SIGNAL TRANSMISSION DEVICE |
| FIRST TEMPERATURE T1 |
| SECOND TEMPERATURE T2 |
| VIBRATION INFORMATION V |

FIG. 26

| CONTENT | |
|---|---|
| DATA FORMAT INFORMATION OF SIGNAL | INFORMATION INCLUDED IN RECEIVED SIGNAL |
| IDENTIFICATION INFORMATION OF SIGNAL TRANSMISSION DEVICE | |
| FIRST TEMPERATURE T1 | |
| SECOND TEMPERATURE T2 | |
| VIBRATION INFORMATION V | |
| IDENTIFICATION INFORMATION OF SIGNAL TRANSMISSION DEVICE SERVING AS NEXT RECEIVER | INFORMATION ADDED BY DEVICE WHICH HAS RECEIVED SIGNAL |
| IDENTIFICATION INFORMATION OF SIGNAL TRANSMISSION DEVICE WHICH HAS RECEIVED SIGNAL | |
| TIME AT WHICH SIGNAL IS RECEIVED | |
| RECEPTION METHOD (COMMUNICATION METHOD) | |
| RADIO WAVE INTENSITY OF RECEIVED SIGNAL | |

FIG. 28

| CONTENT |
| --- |
| DATA FORMAT INFORMATION OF SIGNAL |
| IDENTIFICATION INFORMATION OF SIGNAL TRANSMISSION DEVICE |
| FIRST TEMPERATURE T1 |
| SECOND TEMPERATURE T2 |
| VIBRATION INFORMATION V |
| IDENTIFICATION INFORMATION OF SIGNAL TRANSMISSION DEVICE WHICH HAS RECEIVED SIGNAL |
| TIME AT WHICH SIGNAL IS RECEIVED |
| RADIO WAVE INTENSITY OF RECEIVED SIGNAL |

SIGNAL TRANSMISSION DEVICE AND MANAGEMENT SYSTEM

CROSS REFERENCE TO RELATED APPLICATIONS

This is a U.S. National Stage Application under 35 U.S.C. § 371, based on International Application No. PCT/JP2017/009187, filed Mar. 8, 2017, which claims priority to Japanese Patent Application JP 2016-085248, filed Apr. 21, 2016, each of which is hereby incorporated by reference in its entirety.

TECHNICAL FIELD

The present disclosure relates to a signal transmission device and a management system.

BACKGROUND ART

In order to ascertain a position of an object which can move freely, there are cases in which a transmitter or the like is attached to the object. For example, a transmitter or the like having a function of detecting a position is attached to livestock to manage livestock grazing in a region partitioned by fences or the like, and a position of each head of livestock to which the transmitter has been attached can be ascertained.

For example, the following Patent Literature 1 discloses a technology for managing grazing of livestock by causing an identification tag including a position detector that acquires positional information using a global navigation satellite system (GNSS) to be attached to the livestock.

CITATION LIST

Patent Literature

Patent Literature 1: JP 2008-73005A

DISCLOSURE OF INVENTION

Technical Problem

In the technology disclosed in Patent Literature 1 described above, it is necessary to mount a power source on an identification tag to receive a signal from a GNSS satellite. However, in a case in which a battery and the like serving as a power source is mounted on an identification tag, portability of the identification tag is decreased due to the weight of the power source. In addition, in such a case, since it is also necessary to manage a lifetime of the battery and the like mounted on the identification tag, management of an attachment target becomes more complicated. On the other hand, if not only positional information of an attachment target but also various types of information can be obtained by a signal transmitted from a transmitter, a usage of the transmitter is expected to expand.

In view of the above, the present disclosure proposes a new and improved signal transmission device and management system which are capable of transmitting a signal including information of an attachment target or information of the surrounding of an attachment target.

Solution to Problem

According to the present disclosure, there is provided a management system including: a signal transmission device including a housing that is attached to an object to be managed in a predetermined direction, a first optical power generation unit that includes a light receiving unit on a first surface facing outward in one direction along the predetermined direction, a second optical power generation unit that includes a light receiving unit on a second surface facing outward in another direction along the predetermined direction, a first temperature sensor that has a thermal contact on the first surface, a second temperature sensor that has a thermal contact on the second surface, a communication control unit that transmits a signal including temperature information detected by the first temperature sensor and the second temperature sensor using power generated by at least one of the first optical power generation unit and the second optical power generation unit; and an information processing device including a control unit configured to receive a signal transmitted from the signal transmission device and output the state information of the object to be managed to which the signal transmission device is attached, on a basis of the temperature information detected by at least the first temperature sensor and the second temperature sensor.

In addition, according to the present disclosure, there is provided a signal transmission device including: a housing that is attached to an object to be managed in a predetermined direction; a first optical power generation unit that includes a light receiving unit on a first surface facing outward in one direction along the predetermined direction; a second optical power generation unit that includes a light receiving unit on a second surface facing outward in another direction along the predetermined direction; a first temperature sensor that has a thermal contact on the first surface; a second temperature sensor that has a thermal contact on the second surface; a communication control unit that transmits a signal including temperature information detected by the first temperature sensor and the second temperature sensor using power generated by at least one of the first optical power generation unit and the second optical power generation unit.

Advantageous Effects of Invention

According to the present disclosure as described above, it is possible to transmit a signal including information of an attachment target or information of the surrounding of an attachment target without including a power source.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 22 is an explanatory diagram which shows an example of information stored in a storage unit.

FIG. 24 is an explanatory diagram in which an example of information included in a signal transmitted by the signal transmission device is shown.

FIG. 26 is an explanatory diagram in which an example of information included in a signal transmitted by a signal relay device is shown.

FIG. 28 is an explanatory diagram in which an example of information included in a signal transmitted from a master relay device to a network connection device is shown.

MODE(S) FOR CARRYING OUT THE INVENTION

Figure 1:
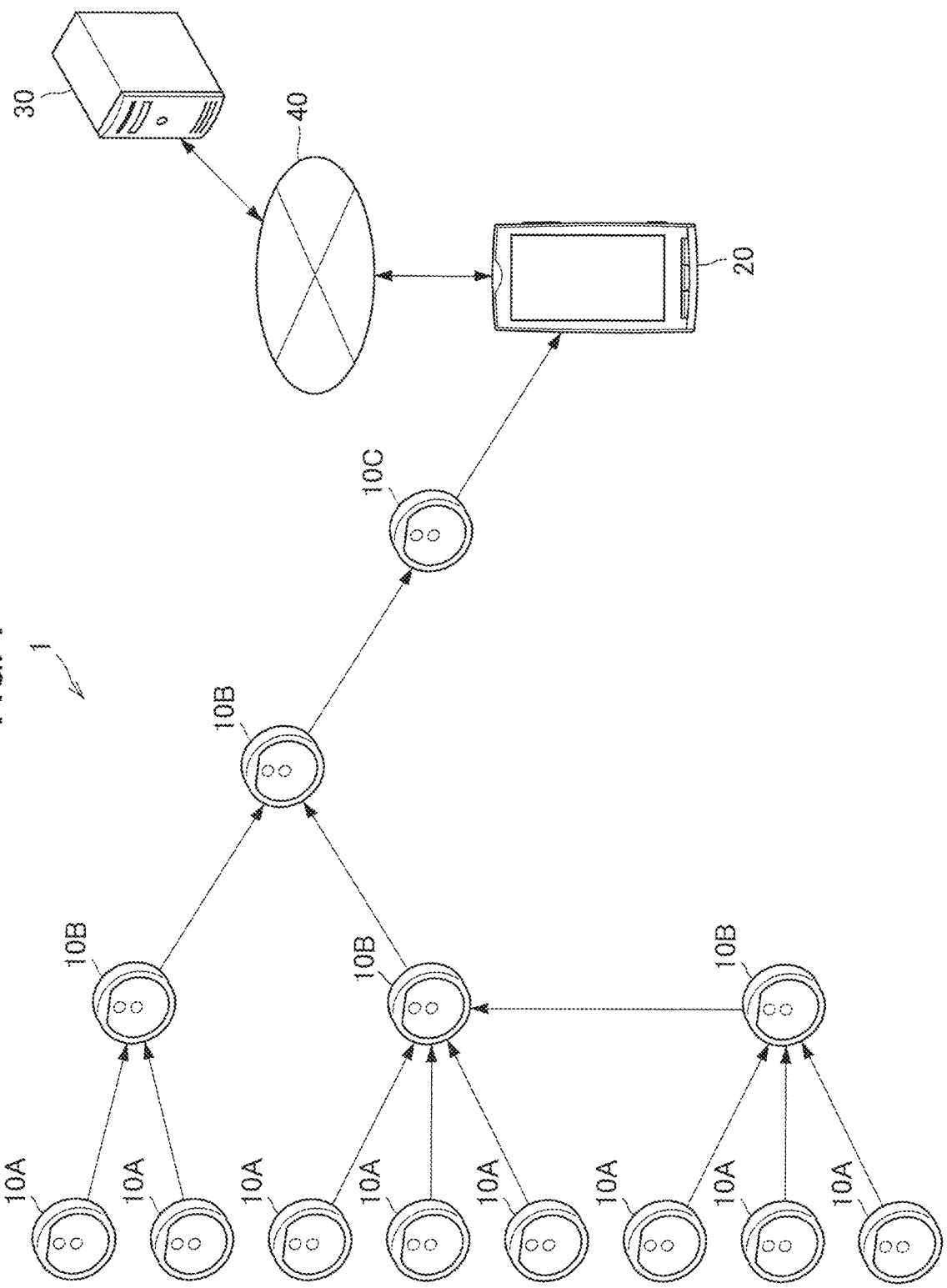
FIG. 1 is an explanatory diagram which shows an outline of a management system according to one embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description will be made in the following order.
1. Management system
1-1. Basic configuration
1-2. Application example
2. Signal transmission device
2-1. Hardware configuration of signal transmission device
2-2. Cover case
2-3. Functional configuration of signal transmission device
2-4. Operation of signal transmission device
3. Information processing device
3-1. Functional configuration of information processing device
3-2. Hardware configuration of information processing device
3-3. Operation of information processing device
4. Other application example of management system
5. Conclusion

1. MANAGEMENT SYSTEM 1-1. Basic Configuration

First, a basic configuration of a management system 1 using a signal transmission device 10 according to an embodiment of the present disclosure will be described with reference to FIG. 1. FIG. 1 is an explanatory diagram which shows the basic configuration of the management system 1 according to the present embodiment.

As shown in FIG. 1, the management system 1 includes a signal transmission device 10A attached to an object to be managed that is freely mobile (for example, a living thing that is not shown (livestock, a person, or the like)), a signal relay device 10B and a master relay device 10C fixed at predetermined positions, a network connection device 20 connected to the master relay device 10C, and an information processing device 30 connected to the network connection device 20 via a communication network 40.

The signal transmission device 10A transmits a signal at a predetermined timing using power generated by a built-in power generation element. The signal relay device 10B receives a signal transmitted from the signal transmission device 10A, and transmits the received signal to the master relay device 10C directly or via another signal relay device 10B or the like. The master relay device 10C receives signals transmitted from respective signal transmission devices 10A, and transmits received signals to the information processing device 30 via the network connection device 20 and the communication network 40.

In addition, the network connection device 20 is an information processing device including a wired or wireless communication device for being connected to the communication network 40. A communication device included in the network connection device 20 may be, for example, a wired or wireless local area network (LAN) compatible communication device, a cable communication device that performs wired cable communication, or a communication device that performs wireless mobile communication. For example, the network connection device 20 may be a mobile phone, a smart phone, a gateway server, or the like.

The communication network 40 is a network in which information is transmitted or received. The communication network 40 may be, for example, the Internet, a satellite communication network, a telephone line network, a mobile communication network (for example, a 3G network and the like), or the like.

The information processing device 30 manages a state of an attachment target to which the signal transmission device 10A is attached by executing information processing on the basis of a signal transmitted from the signal transmission device 10A. As a result, the information processing device 30 can provide a user or the like that manages, monitors, or protects an attachment target to which the signal transmission device 10A is attached with information of the state of the attachment target.

A signal transmitted from the signal transmission device 10A includes identification information of the signal transmission device 10A. In addition, the signal relay device 10B which has received a signal transmitted from the signal transmission device 10A may give the identification information of the signal relay device 10B itself to the received signal and then transmit the signal to another signal relay device 10B. As a result, the management system 1 can ascertain which signal relay device 10B has the signal transmission device 10A that has transmitted a signal in a range in which communication is possible. Therefore, the management system 1 according to the present embodiment can ascertain positions of a signal transmission device 10A that has transmitted a signal and an attachment target to which the signal transmission device 10A is attached on the basis of a position at which the signal relay device 10B which has received a signal is installed.

Moreover, in the management system 1 according to the present embodiment, for a communication method from the signal transmission device 10A to the signal relay device 10B (also referred to as a first communication method), and a communication method between the signal relay devices 10B and from the signal relay device 10B to the master relay device 10C (also referred to as a second communication method), different communication methods or frequencies are used. As a result, the signal relay device 10B can determine whether a received signal is a signal from the signal transmission device 10A or a signal from the signal relay device 10B depending on a communication method or frequency.

Furthermore, in the management system 1 according to the present embodiment, the signal transmission device 10A, the signal relay device 10B, and the master relay device 10C may be configured using the same hardware. In this case, the signal transmission device 10A, the signal relay device 10B, and the master relay device 10C can be configured to exhibit different functions according to communication control information stored in a built-in storage element. That is, functions of the signal transmission device 10A, the signal relay device 10B, and the master relay device 10C can be switched by rewriting the communication control information stored in the built in storage element.

Specifically, the signal transmission device 10A, the signal relay device 10B, and the master relay device 10C are wireless communication devices capable of transmitting or receiving signals by wireless communication, and function as any one of the above devices depending on whether transmission and reception of a signal are possible and a destination of a signal. Note that a connection between the master relay device 10C and the network connection device 20 may be in either a wired or wireless method, and is not particularly limited.

For example, the signal transmission device 10A is a wireless communication device only capable of transmitting a signal to the signal relay device 10B. In addition, the signal relay device 10B is a wireless communication device capable of receiving a signal, and transmitting a received signal to a next signal relay device 10B or the master relay device 10C. Furthermore, the master relay device 10C is a wireless communication device capable of receiving a signal and transmitting a received signal to the network connection device 20 connected via the communication network 40.

Therefore, in the management system 1 according to the present embodiment, an operation of a wireless communication device having the same hardware is controlled according to different communication control information, and thereby causing the wireless communication device to function as each of the signal transmission device 10A, the signal relay device 10B, and the master relay device 10C. Therefore, since a transmission path of a signal from the signal transmission device 10A to the master relay device 10C can be constructed by the same hardware with different communication control information in the management system 1 according to the present embodiment, versatility and flexibility of the whole system can be improved.

Note that the management system 1 according to the present embodiment is not limited to the above example. The signal transmission device 10A, the signal relay device 10B, and the master relay device 10C may be configured by different hardware. For example, the signal transmission device 10A may be configured to be compact and highly portable to reduce a burden on an object to be managed, and the signal relay device 10B and the master relay device 10C may be configured to be fixable at predetermined positions. In addition, the signal relay device 10B and the master relay device 10C may include a power source such as a secondary battery in addition to a power generation element, and may include an input terminal for supplying power from an external power source.

1-2. Application Example of Management System

Figure 2:
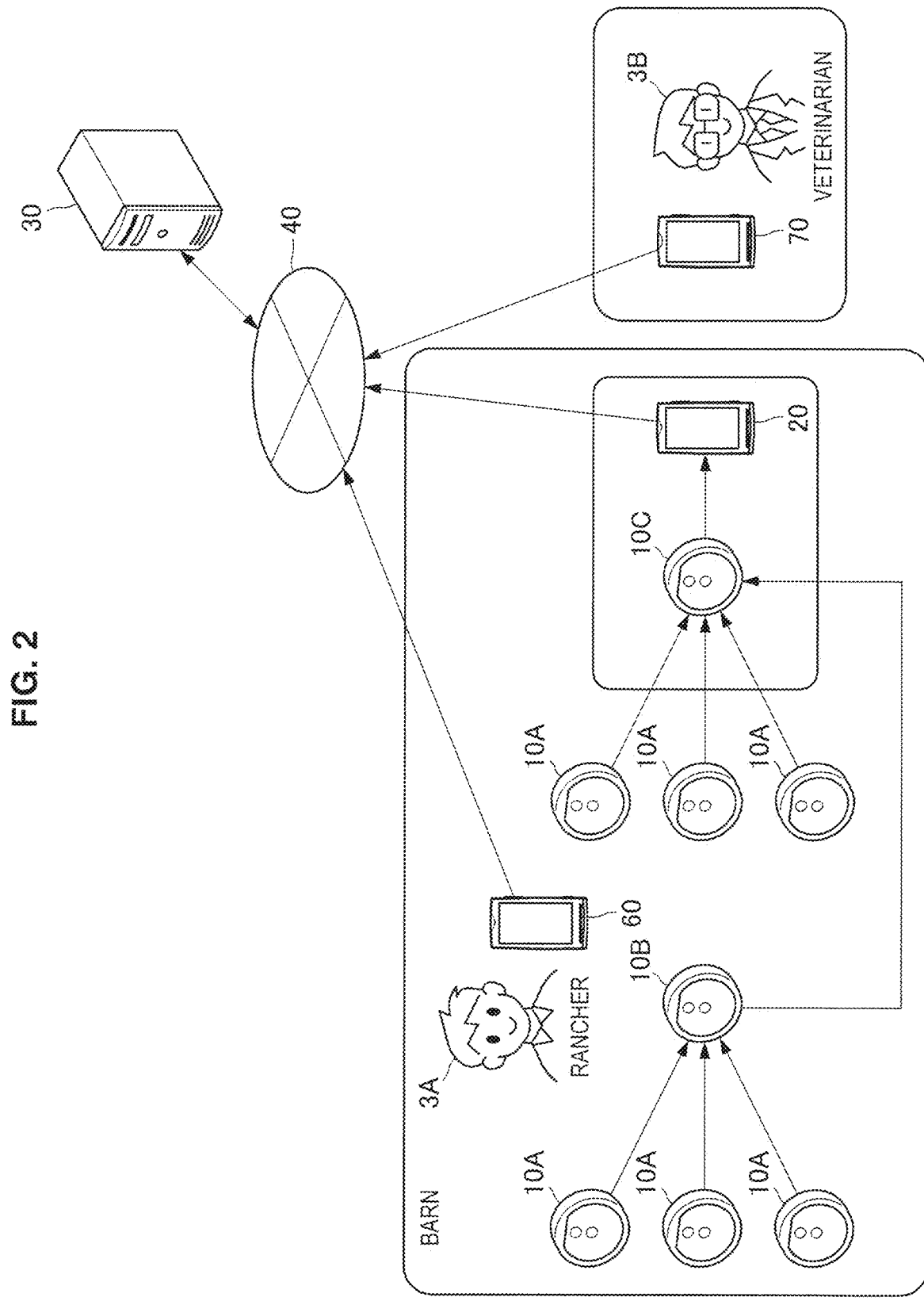
FIG. 2 is an explanatory diagram which describes a first application example of the management system according to the embodiment.

Next, an application example of the management system 1 according to the present embodiment will be described with reference to FIG. 2. FIG. 2 is an explanatory diagram which shows the application example of the management system 1 according to the present embodiment. The application example of the management system 1 according to the present embodiment is an application example to a system that manages livestock by ascertaining a state of livestock such as cattle grazing in a pasture or the like.

The signal transmission device 10A is attached to livestock such as cattle (not shown), and the signal relay device 10B or the master relay device 10C is installed in each of a barn and a grazing area. In a case in which power generated by the built-in power generation element has reached a predetermined amount, the signal transmission device 10A transmits a signal to the signal relay device 10B or the master relay device 10C. Alternatively, the signal transmission device 10A may accumulate power generated by the built-in power generation element, and transmit a signal to the signal relay device 10B or the master relay device 10C at predetermined intervals. A signal received by the signal relay device 10B is transmitted to the master relay device 10C, and is transmitted to the information processing device 30 via the communication network 40 by the network connection device 20 connected to the master relay device 10C.

Here, for communication methods between the signal transmission device 10A and the signal relay device 10B and between the signal transmission device 10A and the master relay device 10C, and a communication method between the signal relay device 10B and the master relay device 10C, different communication methods or frequencies are used. As a result, the master relay device 10C can prevent signals transmitted from the signal transmission device 10A and a signal transmitted from the signal relay device 10B from being confused.

The information processing device 30 determines a position of each signal transmission device 10A on the basis of identification information of the signal transmission device 10A included in a transmitted signal and identification information of the signal relay device 10B which has received the transmitted signal. As a result, the information processing device 30 can ascertain a position of each head of livestock to which the signal transmission device 10A is attached.

Therefore, a rancher 3A who manages livestock to which the signal transmission device 10A is attached can ascertain a position of the livestock to which the signal transmission device 10A is attached by accessing the information processing device 30 using an information terminal 60 such as a smart phone or a tablet terminal. As a result, the rancher 3A can check whether or not the livestock to which the signal transmission device 10A is attached is in the barn or remains in the grazing area.

In addition, in a case in which a signal transmitted to the information processing device 30 includes measurement information from various sensors included in the signal transmission device 10A, the information processing device 30 registers the measurement information from various sensors in association with the identification information of the signal transmission device 10A. Therefore, a veterinarian 3B who manages a health condition of the livestock to which the signal transmission device 10A is attached can ascertain the health condition or biological information of the livestock to which the signal transmission device 10A is attached by accessing the information processing device 30 using an information terminal 70. As a result, the veterinarian 3B can check a presence or absence of livestock to be examined.

For example, in the management system 1 according to the present embodiment, the signal transmission device 10A may include a temperature sensor and a vibration sensor, and a signal transmitted from the signal transmission device 10A may include predetermined temperature information and vibration information. The information processing device 30 can ascertain first state information, for example, activity information of livestock, on the basis of vibration information detected by the vibration sensor. In addition, the information processing device 30 can ascertain second state information, for example, metabolic information of livestock, on the basis of temperature information detected by the temperature sensor. Therefore, the rancher 3A or the veterinarian 3B can manage livestock while checking state information of the livestock, for example, biological information such as an estrus state, a childbirth state, a death or weakness condition, and an injury or disease state.

Hereinafter, the signal transmission device 10 according to the present embodiment will be described in detail with reference to the management system 1 shown in FIG. 2 as an example.

Figure 3:
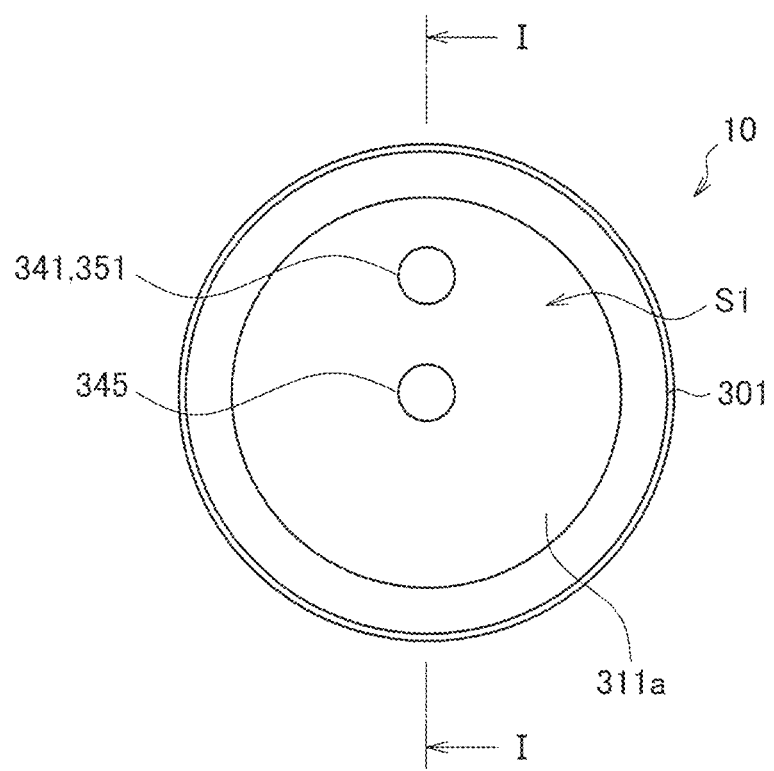
FIG. 3 is a view of a signal transmission device according to the embodiment as seen from a first surface side.
Figure 4:
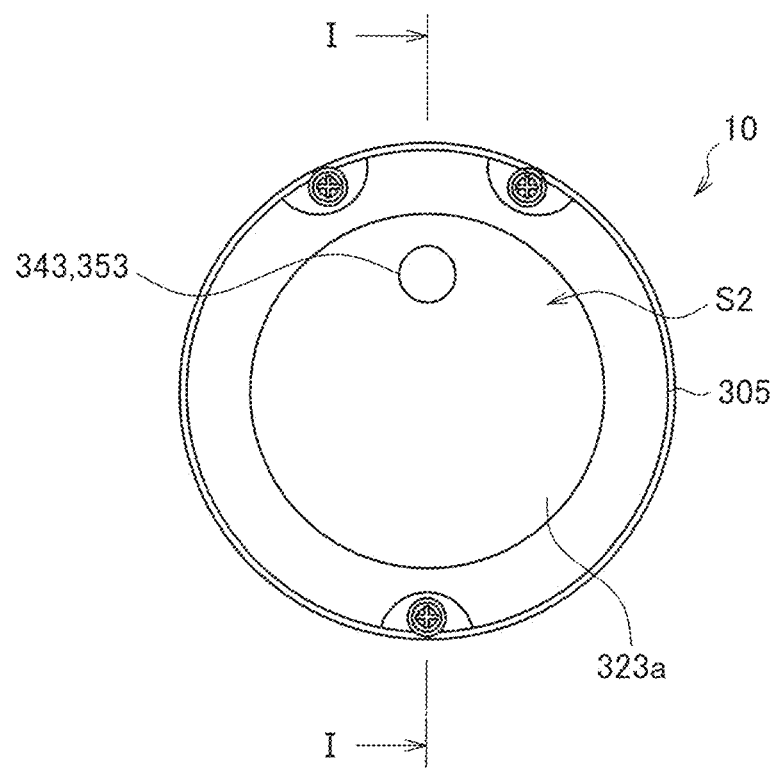
FIG. 4 is a view of the signal transmission device according to the embodiment as seen from a second surface side.
Figure 5:
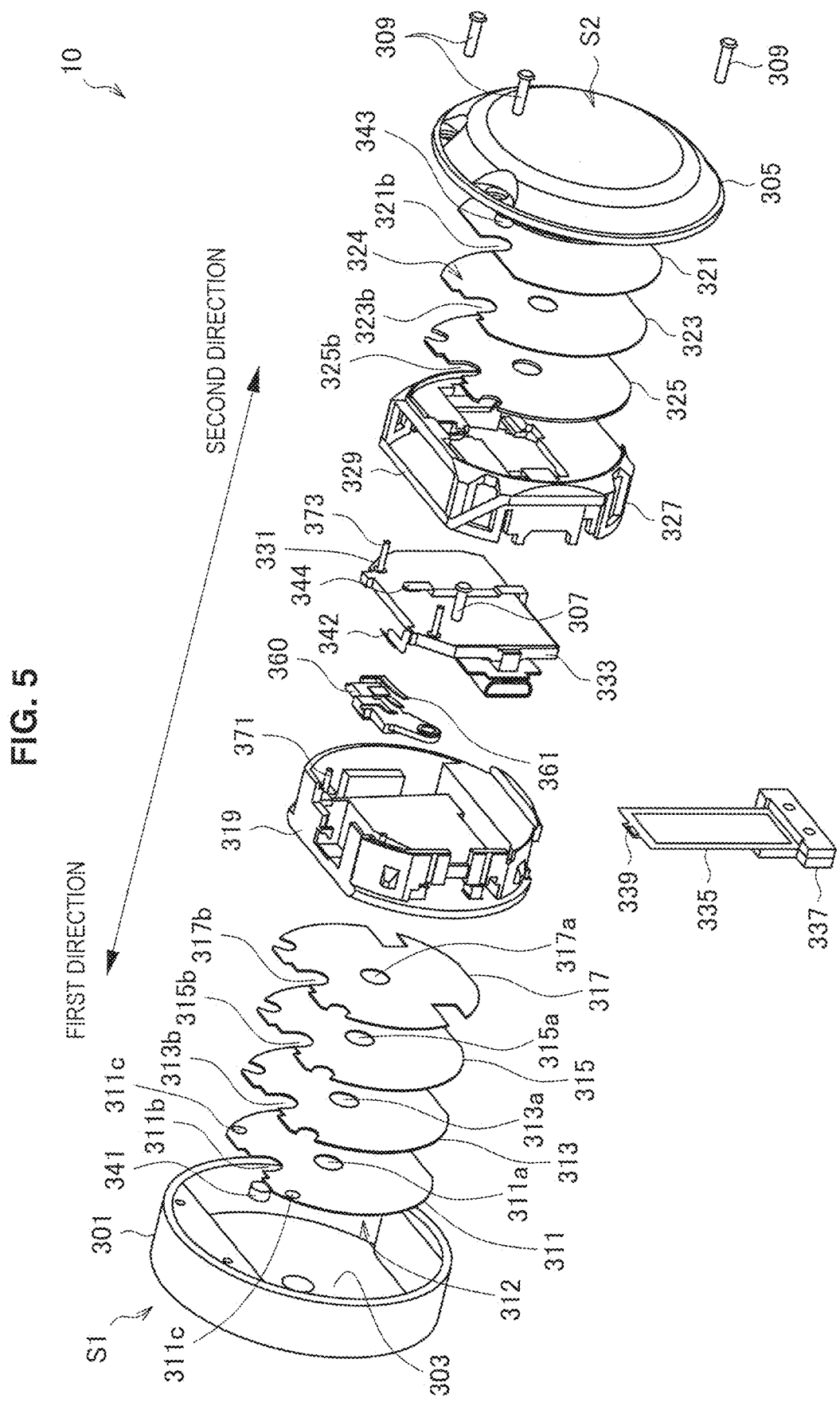
FIG. 5 is an exploded perspective view of the signal transmission device according to the embodiment.
Figure 6:
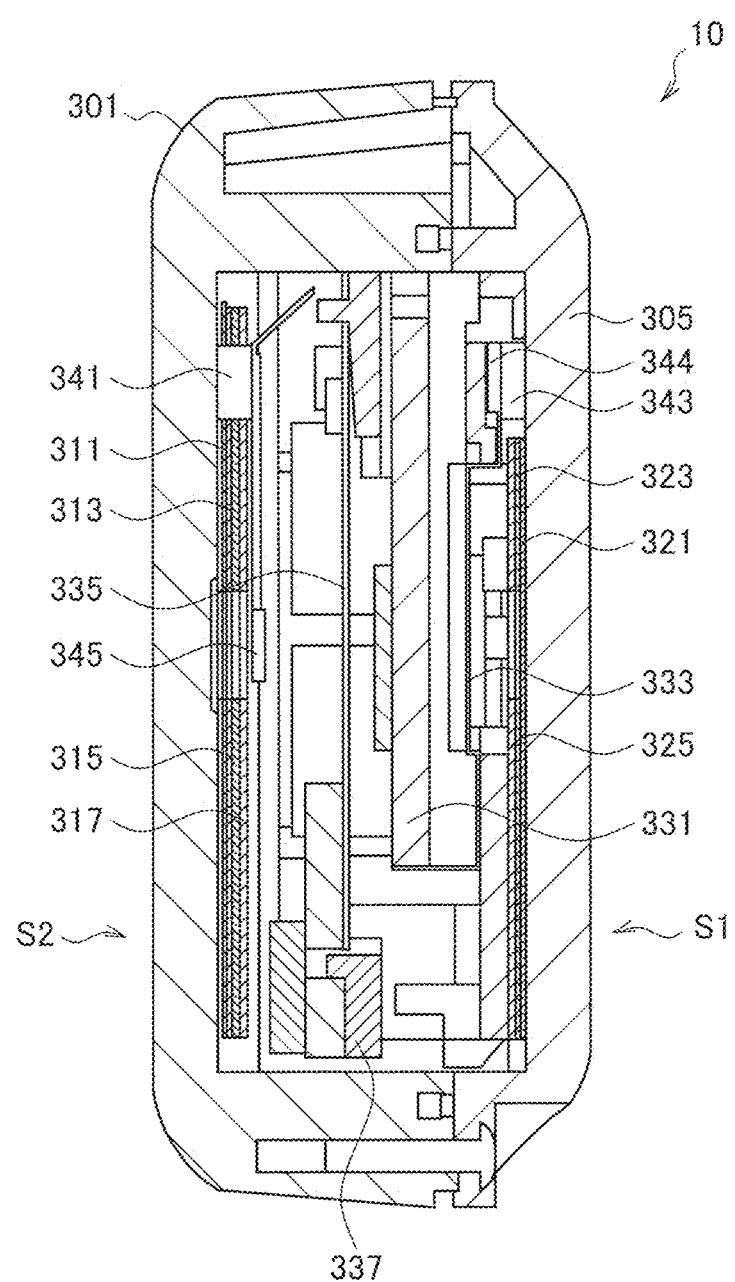
FIG. 6 is a cross-sectional view of the signal transmission device according to the embodiment.

2. SIGNAL TRANSMISSION DEVICE 2-1. Hardware Configuration of Signal Transmission Device A configuration example of the signal transmission device 10 according to the embodiment of the present disclosure will be described with reference to FIGS. 3 to 6. FIG. 3 is a view of the signal transmission device 10 as seen from a first surface S1 side, and FIG. 4 is a view of the signal transmission device 10 as seen from a second surface S2 side. In addition, FIG. 5 is an exploded perspective view of the signal transmission device 10, and FIG. 6 is a cross-sectional view of a I-I cross-section of the signal transmission device 10 of FIGS. 4 and 5, which is viewed in an arrow direction.

Hereinafter, the signal transmission device 10A, the signal relay device 10B, and the master relay device 10C are assumed to be devices including the same hardware although communication control information stored in the built-in storage element is different in the following description. Therefore, in a case in which a configuration of common hardware is described, these devices will be collectively described as a signal transmission device 10. However, in a case in which each function is described, the signal transmission device 10A, the signal relay device 10B, and the master relay device 10C will be described separately.

(2-1-1. Overall Structure)

The signal transmission device 10 includes a first optical power generation unit 311, a second optical power generation unit 323, a non-contact communication antenna 315, a first antenna 328, a second antenna 329, a first temperature sensor 351, a second temperature sensor 353, a vibration sensor 335, and a circuit board 331. These components are accommodated in an accommodating portion 303 of a box-shaped case 301 having a circular outer shape, and furthermore a lid member 305 having a circular outer shape is attached using a fixing screw 309 and held in the case 301. The case 301 and the lid member 305 constitute a housing of the signal transmission device 10. The case 301 and the lid member 305 are outer edge portions in contact with each other, and, for example, a sealing member such as an O-ring is disposed on an inner side from a portion at which the fixing screw 309 is positioned, and is sealed such that moisture or dust does not intrude into the inside. The case 301 and the lid member 305 are made of a transparent resin having optical transparency and can transmit external light such as sunlight and indoor light.

The circuit board 331 is fixed to a base member 319 using a fixing screw 307. At this time, a fixing member 360 is fixed between the circuit board 331 and the base member 319, and one end of the vibration sensor 335 is fixed by the fixing member 360. The fixing member 360 has a conductive electrode extraction spring 361, and the vibration sensor 335 is electrically connected to the circuit board 331 via the electrode extraction spring 361. In addition, an antenna substrate 327 is attached to the base member 319 to further cover the circuit board 331 fixed to the base member 319. The second antenna 329 is disposed on an outer peripheral surface of the antenna substrate 327. The second antenna 329 is electrically connected to the circuit board 331.

A light emitting element 345 (refer to FIG. 3) is provided on a first surface S1 side of the base member 319. The light emitting element 345 is exposed on the first surface S1 via holes 311a, 313a, 315a, and 317a provided in centers of the first optical power generation unit 311, an adhesive sheet 313, a non-contact communication antenna 315, and an adhesive sheet 317. Such a light emitting element 345 may be lit, for example, during power generation by a power generation element or during wireless communication. However, the light emitting element 345 may also be omitted.

The outer shape of the base member 319 into which the antenna substrate 327 is assembled substantially coincides with the outer shape of the accommodating portion 303 of the case 301. The base member 319 into which the antenna substrate 327 is assembled can be sandwiched by the case 301 and the lid member 305 in a case in which the lid member 305 is fixed to the case 301. For this reason, a position of each component in the case 301 is fixed.

The adhesive sheet 317, the non-contact communication antenna 315, the adhesive sheet 313, and the first optical power generation unit 311 are disposed to be sequentially superimposed from an inner side to an outer side further on the first surface S1 side than the base member 319. In addition, an adhesive sheet 325, a second optical power generation unit 323, and a machine nameplate 321 are disposed to be sequentially superimposed from an inner side to an outer side further on the second surface S2 side than the antenna substrate 327. The machine nameplate 321 may be omitted. The signal transmission device 10 is a wireless communication device that includes the first optical power generation unit 311, the second optical power generation unit 323, and the vibration sensor 335 as power generation elements, and is capable of transmitting or receiving a signal via at least one antenna among the first antenna 328 and the second antenna 329 using power generated by the first optical power generation unit 311, the second optical power generation unit 323, and the vibration sensor 335.

Note that a direction from the second surface S2 to the first surface S1 is referred to as a first direction, and a direction from the first surface S1 to the second surface S2 is referred to as a second direction. That is, the first direction and the second direction are opposite to each other.

(2-1-2. Optical Power Generation Unit)

The first optical power generation unit 311 and the second optical power generation unit 323 are optical power generation elements that photoelectrically convert external light such as sunlight or indoor light. The optical power generation unit includes, for example, a silicon-based optical power generation element, a compound semiconductor-based optical power generation element, or a dye-sensitized optical power generation element, and generates power using sunlight or indoor light. The first optical power generation unit 311 and the second optical power generation unit 323 may be solar batteries. Among them, the first optical power generation unit 311 has a light receiving unit 312 on the first surface S1 side oriented to the outside in the first direction. The first optical power generation unit 311 has an electrode 311c on the rear surface side (the inner side), and is electrically connected to the circuit board 331 via a conductive spring 371 provided in the base member 319.

In addition, the second optical power generation unit 323 has a light receiving unit 324 on the second surface S2 side oriented to the outside in the second direction. Each of the light receiving units 312 and 324 is disposed over substantially an entire surface of the first surface S1 and the second surface S2, and is made to obtain an amount of power generation as much as possible. The second optical power generation unit 323 has an electrode not shown on the rear surface side, and is electrically connected to the circuit board 331 via a conductive spring 373 provided in the circuit board 331. Power generated by the first optical power generation unit 311 and the second optical power generation unit 323 is stored as power used for communication.

The signal transmission device 10A according to the present embodiment is attached to, for example, an ear mark of cattle. At this time, any one of a first surface S1 and a second surface S2 faces the ear mark side. Since the light receiving unit 312 of the first optical power generation unit 311 and the light receiving unit 324 of the second optical power generation unit 323 are oriented to the outside in opposite directions, at least one light receiving unit can be reliably exposed to external light. Accordingly, for example, the signal transmission device 10A can continue to transmit signals in a bright daytime period. The signal transmission device 10A attached to livestock such as cattle is referred to as "tag."

In addition, since the light receiving unit 312 of the first optical power generation unit 311 and the light receiving unit 324 of the second optical power generation unit 323 are oriented to the outside in opposite directions, even if the signal transmission device 10A falls out of the ear mark, at least one light receiving unit can be reliably exposed to external light such as sunlight. Therefore, even in such a case, the signal transmission device 10A can continue to transmit signals.

Note that the ear mark may be an identification marker in which an identification number or identification barcode of livestock is described, and moreover, may be a plate-shaped molding article containing an insecticide for controlling mosquitoes and the like which are harmful to livestock.

(2-1-3. Temperature Sensor)

Each of the first temperature sensor 351 and the second temperature sensor 353 has a thermal contact on a first surface S1 side or a second surface S2 side, and detects a first temperature T1 on the first surface S1 side or a second temperature T2 on the second surface S2 side. The first temperature sensor 351 includes a first heat conductor 341 and a first resistance temperature detector (thermistor) 342. The first resistance temperature detector 342 is provided in a flexible circuit board 333 attached to the circuit board 331, and is disposed on the first surface S1 side of the base member 319. The first heat conductor 341 has, for example, a cylindrical shape, and has one end side disposed as a thermal contact on a first surface S1 and the other end side brought into contact with the first resistance temperature detector 342.

The first heat conductor 341 is disposed in notches 311b, 313b, 315b, and 317b provided in upper side portions of the first optical power generation unit 311, the adhesive sheet 313, the non-contact communication antenna 315, and the adhesive sheet 317, and transmits heat sensed by a thermal contact to the first resistance temperature detector 342 disposed on a rear surface side (an inner side) of the light receiving unit 312 of the first optical power generation unit 311. As a result, a resistance value of the first resistance temperature detector 342 changes in accordance with the first temperature T1 on the first surface S1 side, and the first temperature T1 can be detected. The first heat conductor 341 can be made of, for example, an elastic silicon-based thermally conductive resin.

The second temperature sensor 353 includes a second heat conductor 343 and a second resistance temperature detector (thermistor) 344. The second resistance temperature detector 344 is provided in the flexible circuit board 333 attached to the circuit board 331, and is disposed at a position facing a second surface S2 side of the base member 319. The second heat conductor 343 has, for example, a cylindrical shape, and has one end side disposed as a thermal contact on the second surface S2 and the other end side brought into contact with the second resistance temperature detector 344.

The second heat conductor 343 is disposed in notches 321b, 323b, and 325b provided in upper side portions of the machine nameplate 321, the second optical power generation unit 323, and the adhesive sheet 325, and transmits heat sensed using a thermal contact to the second resistance temperature detector 344 disposed on a rear surface side (an inner side) of the light receiving unit 324 of the second optical power generation unit 323. As a result, a resistance value of the second resistance temperature detector 344 changes in accordance with the second temperature T2 on the second surface S2 side, and the second temperature T2 can be detected. The second heat conductor 343, like the first heat conductor 341, can be made of, for example, an elastic silicon-based thermally conductive resin.

The signal transmission device 10A according to the present embodiment is attached to, for example, the ear mark of livestock such as cattle. For this reason, one of a thermal contact of the first temperature sensor 351 and a thermal contact of the second temperature sensor 353 is oriented to a body surface side of livestock, and the other is oriented to the outside. Therefore, a temperature difference ΔT between a first temperature T1 detected by the first temperature sensor 351 and a second temperature T2 detected by the second temperature sensor 353 may occur while livestock is alive. In particular, a body temperature of livestock rises when metabolism of the livestock increases, and thus the temperature difference ΔT can be increased. For this reason, it is possible to ascertain metabolic information of livestock on the basis of the temperature difference ΔT.

(2-1-4. Vibration Sensor)

The vibration sensor 335 detects a vibration occurring in the signal transmission device 10. The vibration sensor 335 is disposed between the first optical power generation unit 311 and the second optical power generation unit 323. For example, the vibration sensor 335 includes a power generation element of an electrostatic type, an electromagnetic type, an inverse magnetostrictive type, or a piezoelectric type, and generates electricity using vibration. In the present embodiment, the vibration sensor 335 is made of a piezoelectric element. A weight 337 is fixed to one end side of the vibration sensor 335 and an electrode 339 is provided on the other end side thereof. Due to the weight 337 being provided, the signal transmission device 10A attached to livestock has the weight 337 vertically positioned downward. Due to the weight 337, the vibration sensor 335 easily shakes and detection of vibration becomes easy.

The vibration sensor 335 is a plate-shaped piezoelectric element having front and rear surfaces oriented in the first direction and the second direction, and deflection can occur due to an impact caused by vibration in the first direction or the second direction which has occurred in the signal transmission device 10. In the vibration sensor 335, power is generated when the deflection occurs, and is output to the circuit board 331. A part of the generated power may be stored, for example, as power used for communication, and the other part may be stored as information indicating the presence or absence and magnitude of vibration. The signal transmission device 10A according to the present embodiment is attached to the ear mark of livestock, and generates vibration according to an operation of the livestock. In a case in which the livestock is cattle, vibration may occur in the signal transmission device 10 not only by walking motion of the cattle but also by moving the ear. Therefore, the higher voltage is generated in the vibration sensor 335 as an activity amount of livestock becomes larger.

(2-1-5. Antenna)

The signal transmission device 10 includes the non-contact communication antenna 315, the first antenna 328, and the second antenna 329. Among them, the non-contact communication antenna 315 is an antenna for non-contact communication, and is a pattern antenna including a power receiving coil formed in a conductive pattern formed on the substrate. The non-contact communication is a communication method in which at least a communication available range is shorter than that of a wireless communication method for transmitting and receiving a signal among the signal transmission device 10A, the signal relay device 10B, and the master relay device 10C. Specifically, the non-contact communication can perform communication within a range of about several cm to several m. As the non-contact communication, various types of communication methods used in a radio frequency identifier (RFID) are exemplified. As an example, Felica (registered trademark) and near field communication (NFC) of an electromagnetic induction type using a magnetic field of 13.56 MHz band are exemplified.

Since the non-contact communication antenna 315 is disposed away from the first antenna 328, the second antenna 329, and the circuit board 331, electromagnetic and electric field interference does not occur. In addition, the non-contact communication antenna 315 is provided on a rear side of the first optical power generation unit 311, but radio wave interference with the first optical power generation unit 311 hardly occurs, and thus non-contact communication can be properly performed. Therefore, the light receiving unit 312 of the first optical power generation unit 311 can be disposed over the entire first surface S1, and more power generation can be performed by the first optical power generation unit 311. In addition, since the first optical power generation unit 311 and the non-contact communication antenna 315 do not have to be arranged on the same surface, an outer shape of the signal transmission device 10 can be decreased in size.

The non-contact communication antenna 315 is used, for example, at the time of writing and rewriting communication control information stored in the storage element built in the signal transmission device 10. As described above, although the case 301 and the lid member 305 are sealed such that moisture or dust does not intrude into the inside, communication control information is written and rewritten by non-contact communication using the non-contact communication antenna 315 without using a direct connection such as a terminal connection. Therefore, the signal transmission device 10 according to the present embodiment can switch the function of the signal transmission device 10 without including switches, contacts, or terminals, or the like. In this manner, the signal transmission device 10 can realize various functions of the signal transmission device 10A, the signal relay device 10B, and the master relay device 10C. Furthermore, the signal transmission device 10 can also update a control program (so-called firmware) of the signal transmission device 10 without physically connecting to an internal circuit board.

In the non-contact communication, for example, power is supplied to the signal transmission device 10 by electromagnetic induction by transmitting a carrier wave from an antenna of a non-contact communication device (not shown) to the non-contact communication antenna 315 of the signal transmission device 10, and furthermore, information is transmitted to the signal transmission device 10 by modulating the carrier wave. In the non-contact communication, communication is performed after power is supplied to the signal transmission device 10 from the non-contact communication device, and thus communication can be performed even if the signal transmission device 10 does not include a power source such as a battery.

Moreover, since the non-contact communication is a communication method in which communication is available only within a close range with a distance of about several cm to several m between the non-contact communication antenna 315 and the antenna of the non-contact communication device, unlike other wireless communication methods, the signal transmission device 10 which writes information can be easily identified. Furthermore, since the non-contact communication is a communication method in which communication is available only within a close range with a distance of about several cm to several m between the non-contact communication antenna 315 and the antenna of the non-contact communication device, it is necessary to bring the signal transmission device 10 and the antenna of the non-contact communication device close to each other to perform communication. Therefore, the signal transmission device 10 can reduce a possibility that information is illegally rewritten by a remote connection from the outside.

The first antenna 328 and the second antenna 329 are wireless communication antennas that use electromagnetic waves or electric fields in different frequency bands. In the signal transmission device 10 according to the present embodiment, the first antenna 328 may be an antenna for Bluetooth low energy (BLE) in a band of, for example, 2.4 GHz, and may be a pattern antenna formed on the circuit board 331 (refer to FIG. 7). In addition, the second antenna 329 may be an antenna for communication based on a wavelength signal having a bandwidth of, for example, 920 MHz, and may include a metal foil or a metal plate disposed along the outer periphery of the antenna substrate 327.

The first antenna 328 and the second antenna 329 are not limited to the above described example, and may be antennas capable of communicating based on wavelength signals having a bandwidth of hundreds MHz to several GHz such as Wi-Fi (registered trademark), ZigBee (registered trademark), Bluetooth (registered trademark), ANT (registered trademark), ANT+ (registered trademark), and EnOcean Alliance (registered trademark), or mobile communication such as 3G or long term evolution (LTE). Note that, in a case in which the signal transmission device 10 is a wireless communication device capable of transmitting or receiving signals in at least two or more communication methods or frequencies, two or more the first antenna 328 and the second antenna 329 may be provided in accordance with a communication method or frequency, and may be multi-band antennas corresponding to a plurality of communication methods or frequency bands.

Figure 7:
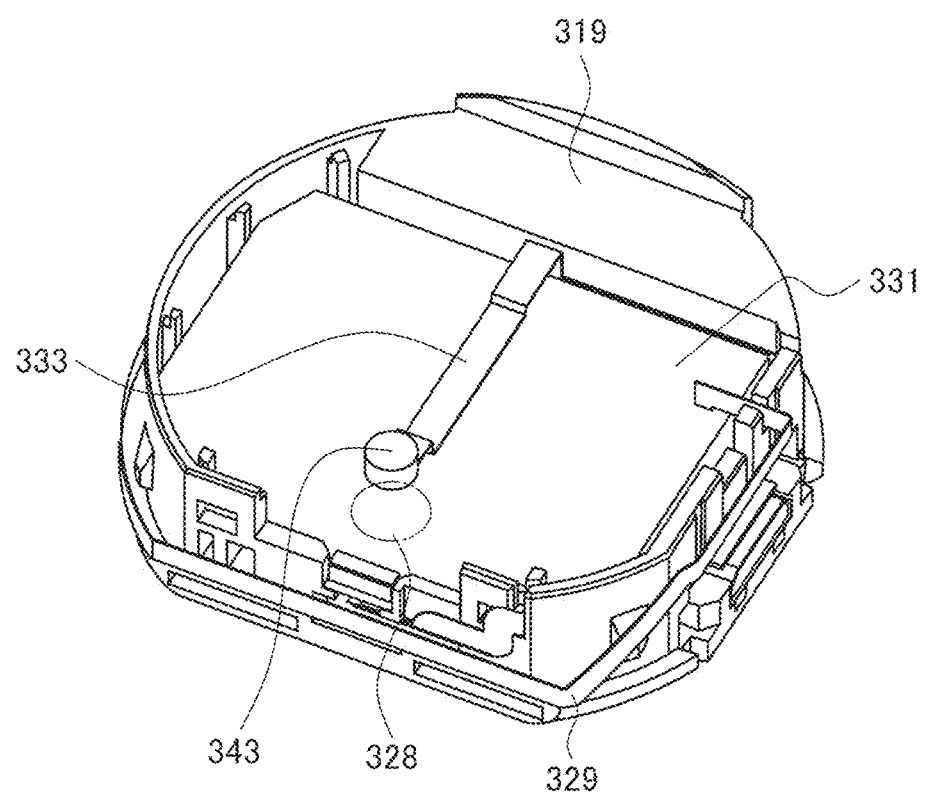
FIG. 7 is an explanatory diagram which shows a disposition of an antenna of the signal transmission device according to the embodiment.

FIG. 7 is a perspective view which shows a state in which the circuit board 331 and the antenna substrate 327 are assembled into the base member 319. However, the antenna substrate 327 is not shown in FIG. 7. The first antenna 328 not shown is formed as a pattern antenna on the circuit board 331. In addition, the second antenna 329 is disposed along the outer periphery of the antenna substrate 327. Since the second antenna 329 is not directly close to the flexible circuit board 333 routed along the first antenna 328 and the circuit board 331 disposed in the base member 319, electric field and electromagnetic interference between the first antenna 328 and the second antenna 329 does not occur.

Since the signal transmission device 10 according to the present embodiment can generate power using the first optical power generation unit 311, the second optical power generation unit 323, and the vibration sensor 335, it can transmit signals without having a power source such as a battery mounted thereon. As a result, the portability of the signal transmission device 10 can be improved, and the burden on an attachment target can be reduced. In addition, the signal transmission device 10 does not need to manage the lifetime of the power source such as a battery, and thus it is possible to more simplify the management of an attachment target.

Note that, in a case in which the signal transmission device 10 is used as the signal relay device 10B or the master relay device 10C, the signal transmission device 10 may be installed to be fixed at a predetermined position. In this case, since it is not necessary to consider the portability, the signal transmission device 10 may be connected to the power source such as a battery. In the case in which the signal transmission device 10 is used as the signal relay device 10B or the master relay device 10C, since the signal transmission device 10 is always in a reception standby state, and continuously consumes power, it is preferable that the signal transmission device 10 be connected to a stable power source such as a battery.

2-2. Cover Case (2-2-1. Overall Structure of Cover Case)

In a case in which the signal transmission device 10 is used as the signal transmission device 10A attached to cattle, the signal transmission device 10A is attached to the ear mark of cattle using, for example, a cover case 200. An ear mark for identifying an individual body is attached to the ear of cattle bred by a rancher and the like. Since cattle has a habit of moving ears, vibration which can be detected by the vibration sensor 335 increases as compared with a case in which the signal transmission device 10 is attached to the leg, the neck, or the like, and the activity information of cattle is more easily ascertained. In addition, due to the first temperature sensor 351 and the second temperature sensor 353 having thermal contacts on the first surface S1 and the second surface S2 oriented to the outside in opposite directions, it is possible to obtain a temperature difference between a temperature changing in accordance with a body temperature and the outside temperature, and to ascertain metabolic information of cattle.

Figure 8:
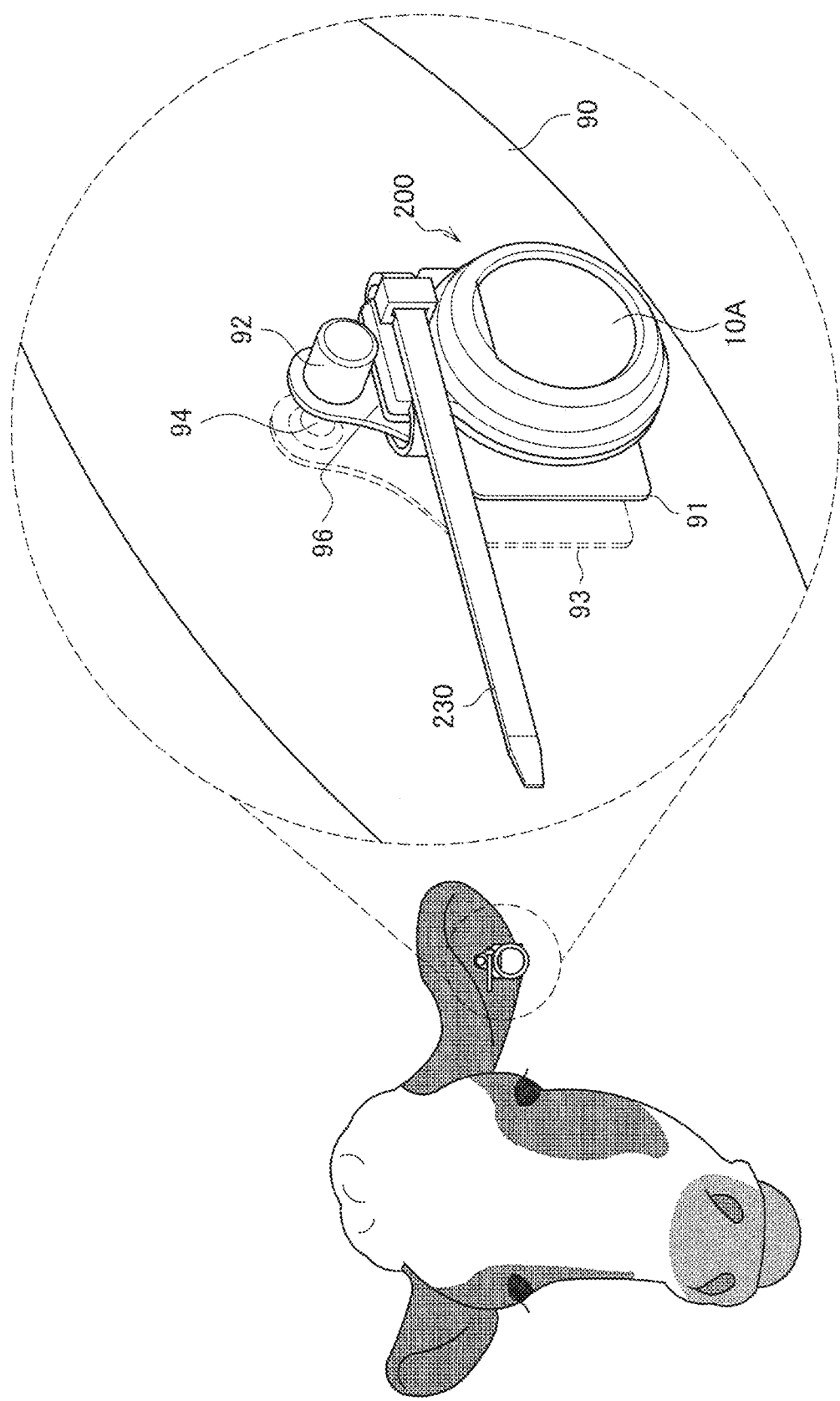
FIG. 8 is an explanatory diagram which shows a signal transmission device attached to an ear mark using a cover case.
Figure 9:
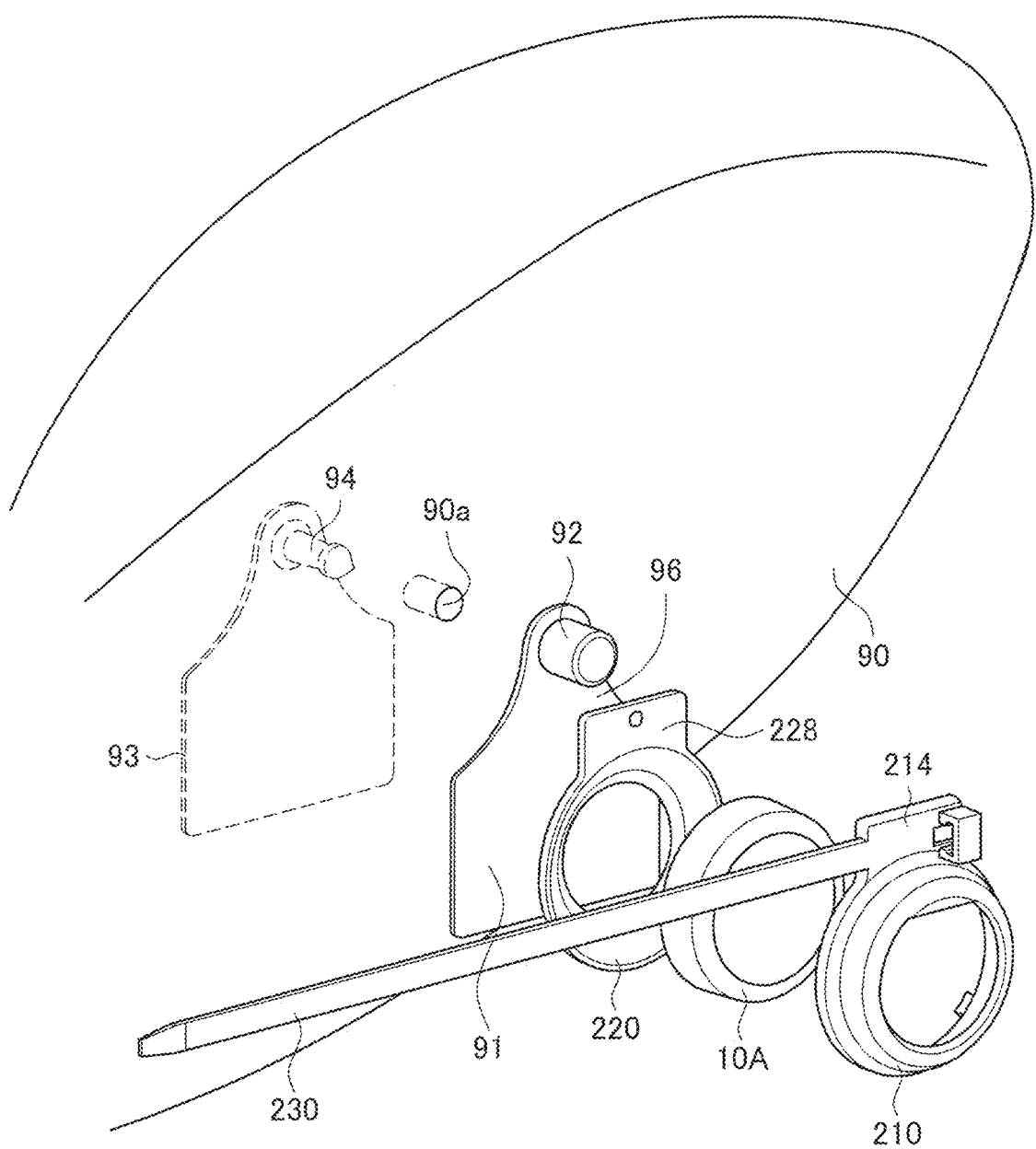
FIG. 9 is an exploded perspective view of the signal transmission device attached to an ear mark using the cover case.

FIGS. 8 and 9 show how the cover case 200 accommodating the signal transmission device 10A is attached to a first ear mark 91 attached to an ear 90 of cattle. FIG. 8 is a schematic diagram which shows a state in which the signal transmission device 10A that is a tool to be held is attached to the first ear mark 91 attached to the ear 90 of cattle using the cover case 200, and FIG. 9 is a perspective view which shows the cover case 200, the signal transmission device 10A, the first ear mark 91, and a second ear mark 93 in an exploded manner.

The first ear mark 91 and the second ear mark 93 cause a pin 94 provided in the second ear mark 93 to be inserted into a hole 90a provided in the ear 90 of cattle, inserts the pin 94 into a pin acceptance unit 92 provided in the first ear mark 91 to be attached to the ear 90, and connects them to be attached to the ear 90. The first ear mark 91 is disposed on a front side of the ear 90, and the second ear mark 93 is disposed on a rear side of the ear 90. In the illustrated example, the cover case 200 is attached to a neck portion 96 of the first ear mark 91.

The cover case 200 is constituted by a first half 210 and a second half 220. The signal transmission device 10A is accommodated inside the first half 210 and the second half 220 coupled to each other. Furthermore, the signal transmission device 10A accommodated in the cover case 200 is attached to the first ear mark 91 by winding a band portion 230 provided in the first half 210 around the neck portion 96 of the first ear mark 91.

Figure 10:
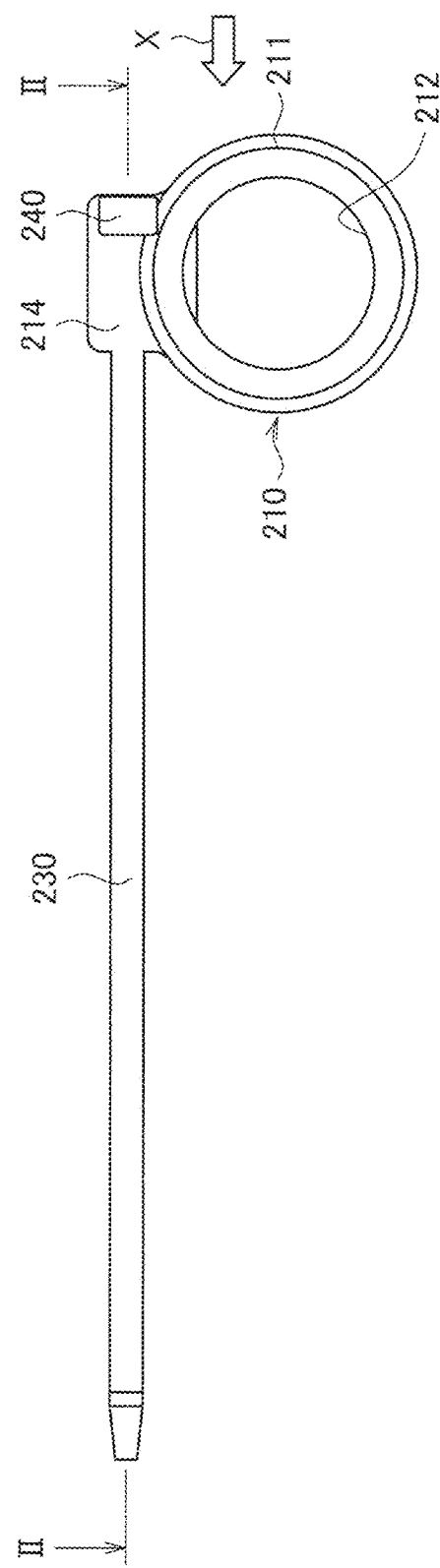
FIG. 10 is a plan view of a first half of the cover case of the signal transmission device according to the embodiment.
Figure 11:
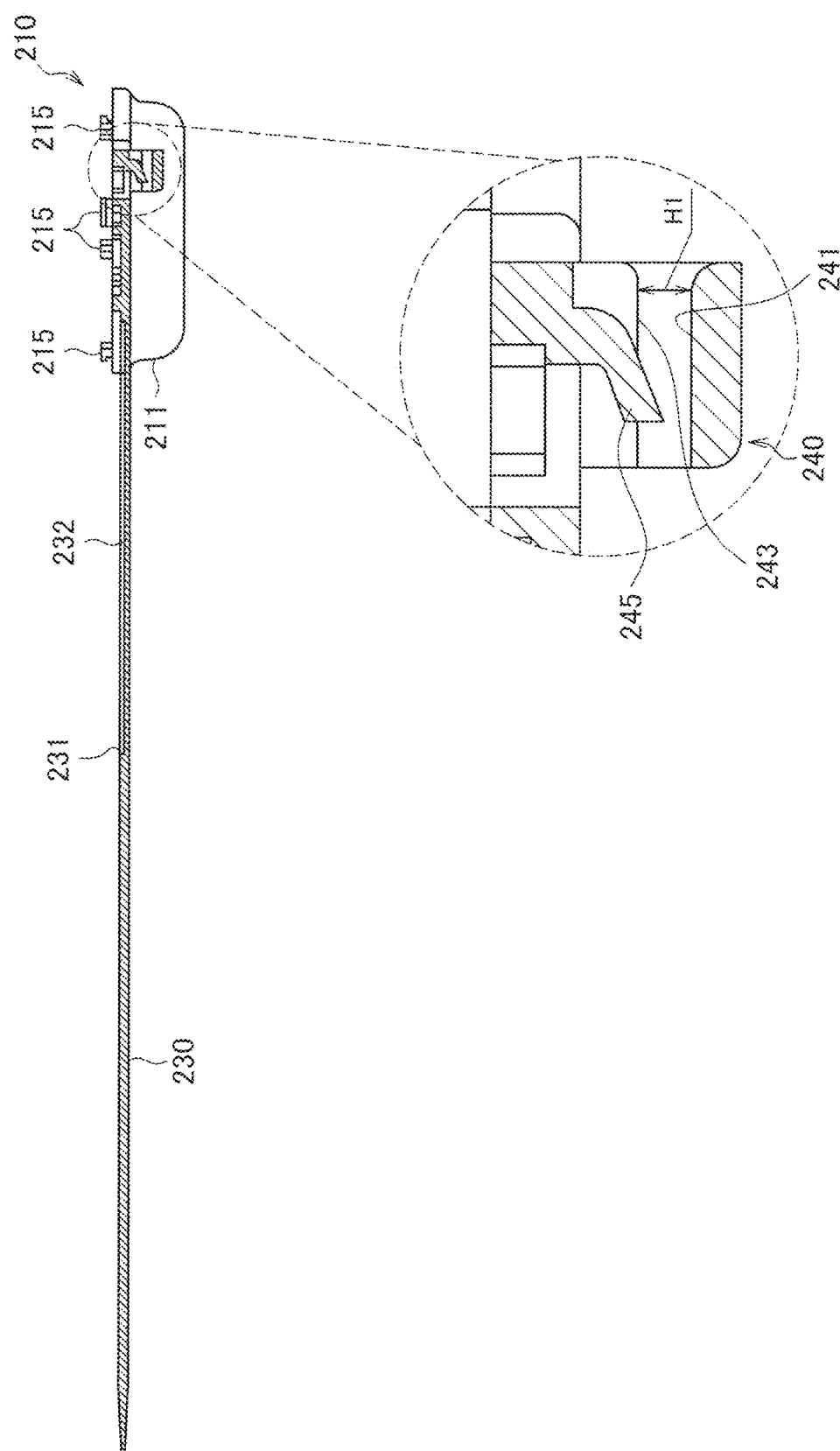
FIG. 11 is a cross-sectional view of a II-II cross-section of the first half shown in FIG. 10 which is viewed in an arrow direction.
Figure 12:
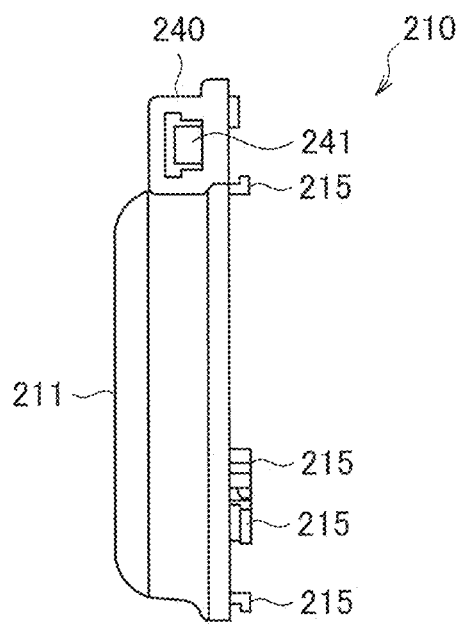
FIG. 12 is a side surface view of the first half shown in FIG. 10 as seen from a direction of an arrow X.
Figure 13:
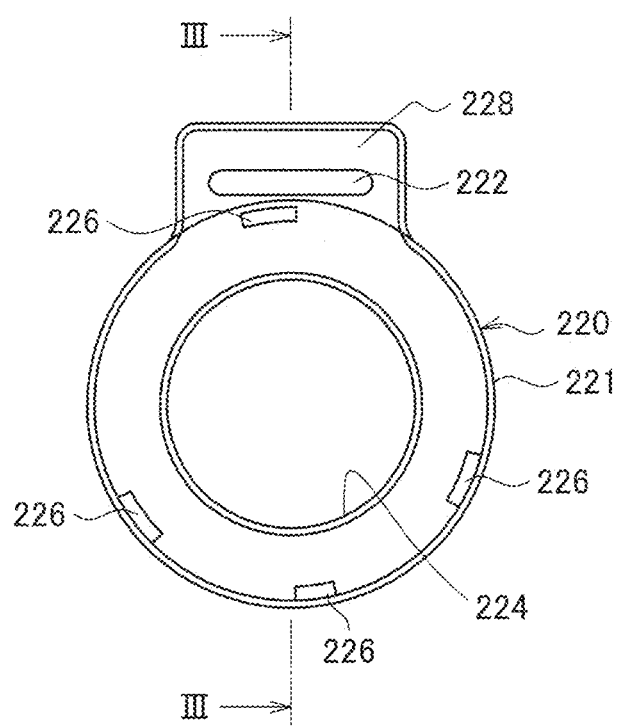
FIG. 13 is a plan view of a second half of the cover case of the signal transmission device according to the embodiment.
Figure 14:
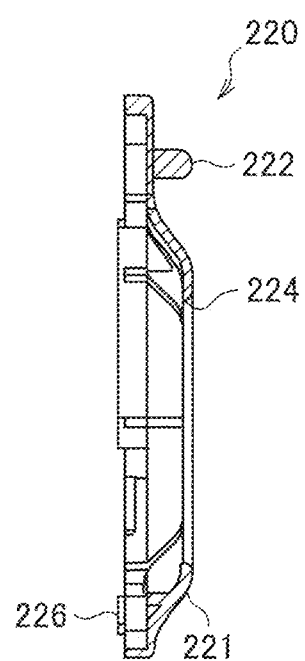
FIG. 14 is a cross-sectional view of a III-III cross-section of the second half shown in FIG. 13 as seen from the arrow direction.

FIGS. 10 to 12 are explanatory diagrams which show the first half 210 constituting the cover case 200. FIG. 10 is a plan view of the first half 210 as seen from the surface side, and FIG. 11 is a cross-sectional view of the first half 210 taken along a center line of the band portion 230, and corresponds to a cross-sectional view of a II-II cross-section of FIG. 10 as seen in an arrow direction. FIG. 12 is a side surface view of the first half 210 shown in FIG. 10 as seen in a direction of an arrow X. In addition, FIGS. 13 and 14 are explanatory diagrams which show the second half 220 constituting the cover case 200. FIG. 13 is a plan view of the second half 220 as seen from the surface side, and FIG. 14 is a cross-sectional view of a III-III cross-section of the second half 220 shown in FIG. 13 as seen in an arrow direction.

The first half 210 has a case main body portion 211, an overhanging portion 214, the band portion 230, and a connection portion 240. The first half 210 may be an integrally molded article made of a resin material. The first half 210 is coupled with the second half 220 while in contact on rear surface sides of the case main body portion 211 and the overhanging portion 214. The case main body portion 211 has a circular outer shape, and has a substantially dome shape that can accommodate a part of the signal transmission device 10A. A positioning structure (not shown) such as a rib or a uneven shape is provided such that the signal transmission device 10A is properly positioned and accommodated in a housing space formed by the case main body portion 211. As a result, the position and orientation of the signal transmission device 10A are made not to be shifted within the cover case 200.

In addition, the case main body portion 211 has an opening 212, and the first surface S1 or the second surface S2 of the signal transmission device 10A accommodated therein is exposed to outside. That is, for example, in a case in which the first surface S1 of the signal transmission device 10A is disposed on the first half 210 side, a thermal contact of the first temperature sensor 351 and the light receiving unit 312 of the first optical power generation unit 311 provided on the first surface S1 side is exposed to the outside. Therefore, an incident amount of external light such as sunlight incident on the light receiving unit 312 of the first optical power generation unit 311 is less likely to decrease, and an amount of heat sensed by the thermal contact of the first temperature sensor 351 is less likely to decrease.

The overhanging portion 214 is formed to protrude radially outward from the case main body portion 211, and the band portion 230 extending in a direction substantially orthogonal to an extending direction of the overhanging portion 214 is provided in the overhanging portion 214 of the first half 210. The band portion 230 is designed to have an appropriate length in accordance with a width of the neck portion 96 of the first ear mark 91. A rectangular groove 232 is formed on the rear surface side of the band portion 230. In the groove 232, a step portion 231 of an edge in a tip direction of the band portion 230 becomes an engaging portion to be locked at a locking portion in the connection portion 240.

Note that "substantially orthogonal" in the present specification does not necessarily have to be orthogonal, and includes a state of not being orthogonal within an error range.

The connection portion 240 into which the band portion 230 is inserted is provided at the end on a side opposite to the extending direction of the band portion 230 on the surface side of the overhanging portion 214 of the first half 210. A claw portion 245 serving as a locking portion which is locked at the step portion 231 of the band portion 230 is provided in the connection portion 240, and the band portion 230 inserted into the connection portion 240 is bound by the claw portion 245 being locked at the step portion 231, and the cover case 200 is made not to fall out of the first ear mark 91.

The second half 220 has a case main body portion 221, an overhanging portion 228, and a protruding portion 222. The second half 220 may be an integrally molded article made of resin material. The second half 220 is coupled to be in contact with the first half 210 on the rear surface side of the case main body portion 221 and the overhanging portion 228, and accommodates the signal transmission device 10A in the case main body portion 221. The case main body portion 221 of the second half 220 has a circular outer shape, and has a substantially dome shape capable of accommodating a part of the signal transmission device 10A. A positioning structure (not shown) such as a rib or uneven shape is provided such that the signal transmission device 10A is properly positioned and accommodated in a housing space formed by the case main body portion 221. As a result, the position and orientation of the signal transmission device 10A are made not to be shifted within the cover case 200.

In addition, the case main body portion 221 has an opening 224, and the first surface S1 or the second surface S2 of the signal transmission device 10A accommodated therein is exposed to outside. That is, for example, in a case in which the second surface S2 of the signal transmission device 10A is disposed on the second half 220 side, a thermal contact of the second temperature sensor 353 and the light receiving unit 324 of the second optical power generation unit 323 provided on the second surface S2 side is exposed to outside. Therefore, an incident amount of external light such as sunlight incident on the light receiving unit 324 of the second optical power generation unit 323 is less likely to decrease, and an amount of heat sensed by the thermal contact of the second temperature sensor 353 is less likely to decrease.

The overhanging portion 228 is formed to protrude radially outward from the case main body portion 221, and the protruding portion 222 extending in a direction substantially orthogonal to an extending direction of the overhanging portion 228 is provided on a surface side of the overhanging portion 228 of the second half 220. The protruding portion 222 has a function of stabilizing a posture of the cover case 200 when the cover case 200 is attached to the first ear mark 91.

Note that the signal transmission device 10 may be accommodated in the cover case 200 such that the weight 337 included therein is positioned on a side opposite to the positions of the overhanging portions 214 and 228. As a result, the cover case 200 can be attached to the first ear mark 91 with the overhanging portions 214 and 228 facing upward, and the signal transmission device 10 can be attached with the weight 337 facing downward.

(2-2-2. Coupling Structure)

An engaging claw 215 is provided on an outer periphery of the case main body portion 211 of the first half 210, which faces the second half 220. In addition, an engaging portion 226 is provided on an outer periphery of the case main body portion 221 of the second half 220, which faces the first half 210. The first half 210 and the second half 220 are coupled to each other by the engaging claw 215 of the first half 210 being locked at the engaging portion 226 of the second half 220. The shown example of the cover case 200 includes four engaging claws 215 and four engaging portions 226, but the number of the engaging claws 215 and the engaging portions 226 is not limited to four.

Figure 15:
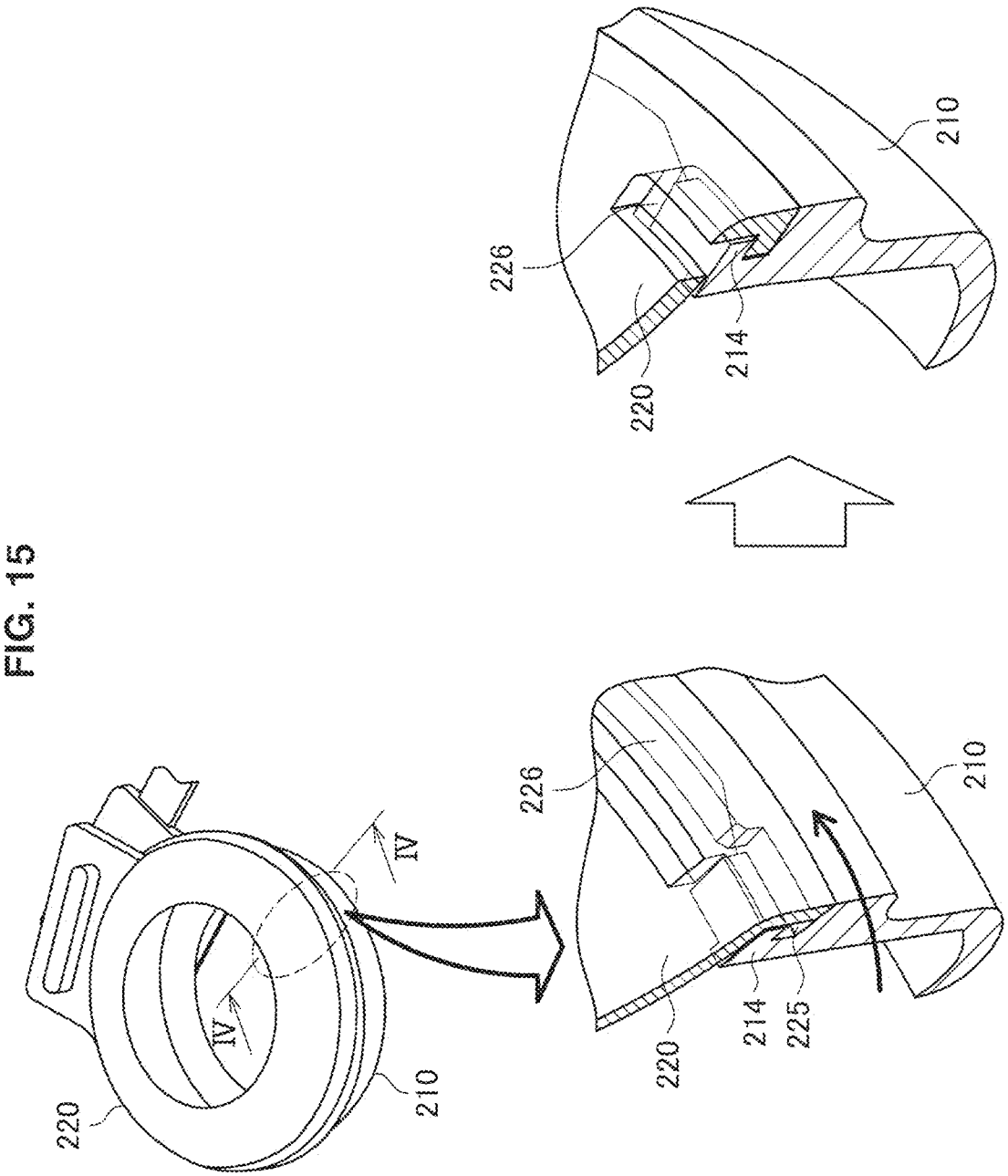
FIG. 15 is an explanatory diagram which shows how the first half and the second half are coupled.

FIG. 15 shows how the first half 210 and the second half 220 are coupled to each other. First, the engaging claw 215 of the first half 210 is inserted into an acceptance unit 225 adjacent to the engaging portion 226 of the second half 220, and an outer periphery of the case main body portion 211 of the first half 210 is brought into contact with an outer periphery of the case main body portion 221 of the second half 220 (a IV-IV cross-sectional view on a left side of FIG. 15). From this state, the engaging claw 215 is locked at the engaging portion 226, and the first half 210 and the second half 220 are coupled to each other by relatively rotating the first half 210 and the second half 220 in a circumferential direction (a right diagram of FIG. 15). Note that the signal transmission device 10A is not shown in FIG. 15.

(2-2-3. Locking Structure of Band)

Figure 16:
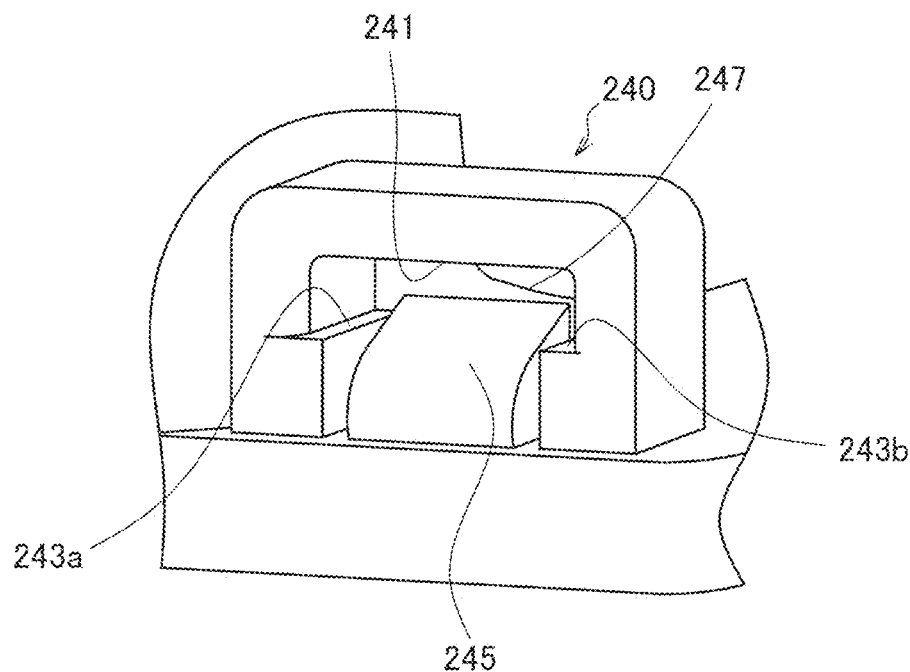
FIG. 16 is a perspective view of a connection portion of the first half according to the embodiment.
Figure 17:
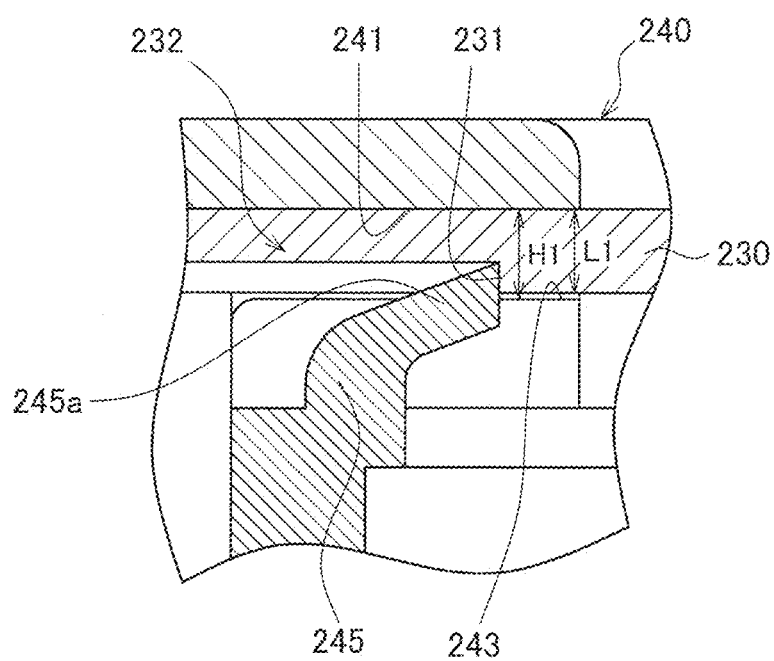
FIG. 17 is an explanatory diagram which shows a state in which a band portion is held in the connection portion.

FIG. 16 is a perspective view of the connection portion 240 as seen in an insertion direction of the band portion 230. FIG. 17 is a cross-sectional view which shows a state in which the band portion 230 is inserted into the connection portion 240 and the claw portion 245 serving as a locking portion is locked at a step portion 231 of the groove 232 of the band portion 230 as an engaging portion.

The connection portion 240 has an opening 247 and a claw portion 245 rising from the surface of the overhanging portion 214 in the opening 247. The opening 247 has a substantially T shape. The claw portion 245 rises from a bottom surface of the T-shaped opening 247. A distance H1 between a top surface of the T-shaped opening 247 (a first guide surface) 241 and surfaces of shoulder portions on both side of the T-shaped opening 247 (a second guide surface) 243 is designed to have a size obtained by adding a width of minute clearance to a thickness L1 of the band portion 230. The top surface of the opening 247 constitutes the first guide surface 241, and a first surface portion 243a and a second surface portion 243b of the shoulder portions on both sides of the opening 247 constitute the second guide surface 243. The first guide surface 241 and the second guide surface 243 are substantially parallel to an extending direction of the connection portion 240, that is, the surface of the overhanging portion 214. The posture of the band portion 230 is held parallel to the overhanging portion 214 by the first guide surface 241 and the second guide surface 243.

The groove 232 provided in the band portion 230 does not exist on both end sides in a width direction of the band portion 230, the groove 232 of the band portion 230 does not face at least one of the first surface portion 243a and the second surface portion 243b constituting the second guide surface 243. For this reason, both ends in the width direction of the band portion 230 inserted into the opening 247 of the connection portion 240 are guided by the first guide surface 241 and the second guide surface 243, and the band portion 230 is held parallel to the surface of the overhanging portion 214.

The claw portion 245 is shaped to be inclined toward the insertion direction of the band portion 230 after rising vertically from the surface of the overhanging portion 214. A tip end portion of the claw portion 245 protrudes further toward the first guide surface 241 side than the second guide surface 243, and is positioned inside the opening 247. For example, the tip end portion of the claw portion 245 may protrude further toward the first guide surface 241 side than the second guide surface 243 by a height corresponding to a height of one third to one half of the distance H1 between the first guide surface 241 and the second guide surface 243.

A tip end surface of the claw portion 245 extends in a direction substantially perpendicular to the surface of the overhanging portion 214. While an inclined portion 245a on the tip end side of the claw portion 245 bends when the band portion 230 is inserted, if the groove 232 provided in the band portion 230 comes to a position facing the inclined portion 245a, the inclined portion 245a enters the groove 232 due to a reaction force of deflection, and is locked at the step portion 231 of an edge of the groove 232. At this time, only the tip end of the claw portion 245 is in contact with the band portion 230, and the claw portion 245 is not pressed downward. Both the tip end surface of the claw portion 245, and the step portion 231 of the groove 232 of the band portion 230 extend in a direction substantially perpendicular to the surface of the overhanging portion 214. In addition, the band portion 230 is held to be parallel to the surface of the overhanging portion 214 by the first guide surface 241 and the second guide surface 243. For this reason, the claw portion 245 and the step portion 231 are locked in a relatively strong manner.

Furthermore, a length of the inclined portion 245a on the tip end side of the claw portion 245 is designed to be appropriately short, and a deflection amount of the claw portion 245 is relatively small. As a result, after the claw portion 245 is locked at the step portion 231 of the edge of the groove 232, a locking state is less likely to be released. Note that a slit (a long hole) may be provided instead of the groove 232.

Figure 18:
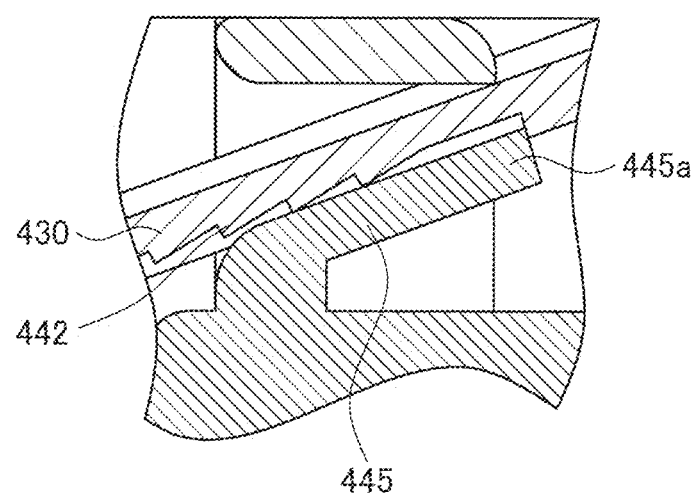
FIG. 18 is an explanatory diagram which shows how a band portion is held in a connection portion according to a reference example.

For comparison, FIG. 18 shows a locking state of a conventional tie-wrap. In a configuration of the conventional tie-wrap, since a band portion 430 is not held in a predetermined posture in the connection portion 440, the band portion 430 is disposed along a direction of an inclined portion 445a of a claw portion 445. In this case, in the conventional tie-wrap, the claw portion 445 is designed to be relatively long, and, since a plurality of steps 442 are continuously provided as engaging portions in the band portion 430, the claw portion 445 is pressed by the step 442 to bend downward, and an amount of locking between a tip of the claw portion 445 and a step 442 of the band portion 430 is likely to be small. For this reason, in a case in which a relatively small load (tension) is applied to the band portion 430, the band portion 430 is easily detached.

In this manner, in the cover case 200 of the signal transmission device 10A according to the present embodiment, the band portion 230 wound around the first ear mark 91 is less likely to be detached from the connection portion 240, and the signal transmission device 10A is less likely to fall out of cattle even by vibration, hooking, or the like. Note that only one step portion 231 at which the claw portion 445 of the connection portion 240 is locked is provided in accordance with the length of the band portion 230 wound around the first ear mark 91 in the cover case 200 of the signal transmission device 10A according to the present embodiment. Therefore, it can be guaranteed that the same attachment state is established for the same ear mark.

(2-2-4. Posture Stabilized Structure)

The signal transmission device 10A according to the present embodiment includes the vibration sensor 335, and vibration or impact in a direction intersecting the first surface S1 and the second surface S2 is detected. For this reason, in a case in which the posture of the cover case 200 is not stable, such as the cover case 200 is biased against the first ear mark 91, there is a concern that a detection accuracy of vibration may decrease. For this reason, the protruding portion 222 is provided in the overhanging portion 228 of the second half 220 in contact with the first ear mark 91 and the posture of the cover case 200 can be stabilized.

Figure 19:
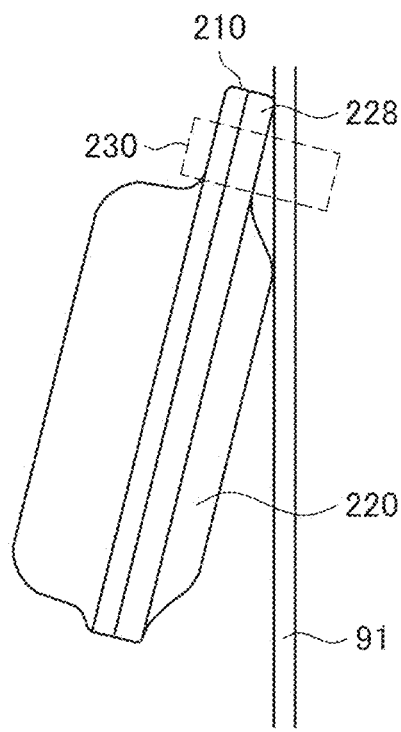
FIG. 19 is an explanatory diagram which shows a posture of a cover case in a case in which the cover case with no protruding portion is used.
Figure 20:
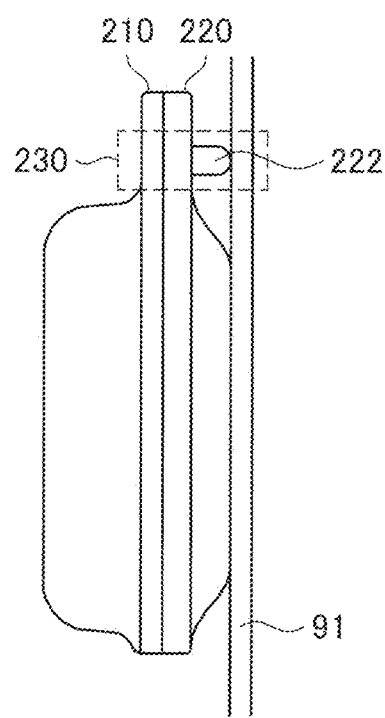
FIG. 20 is an explanatory diagram which shows a posture of a cover case in a case in which the cover case with a protruding portion is used.

FIGS. 19 and 20 are explanatory diagrams which show differences in the posture of the cover case 200 according to a presence or absence of the protruding portion 222. FIGS. 19 and 20 are views of the cover case 200 attached to the first ear mark 91 as seen from the side, respectively. As shown in FIG. 19, in a case in which the protruding portion is not provided in the cover case 200, when the band portion 230 is wound around the first ear mark 91, a space is generated between the overhanging portion 228 of the second half 220 and the first ear mark 91 at a winding position of the band portion 230, and thus a distance between the overhanging portion 228 and the first ear mark 91 is likely to change. For this reason, shaking of the cover case 200 results in the cover case 200 shaking in all directions: front and rear, and left and right, and the posture being not stable. For this reason, the detection accuracy of vibration is likely to decrease.

On the other hand, as shown in FIG. 20, in a case in which the protruding portion 222 is provided in the cover case 200, when the band portion 230 is wound around the first ear mark 91, the protruding portion 222 is in line contact or surface contact with the first ear mark 91 within a predetermined length range at a position at which the band portion 230 is wound. The protruding portion 222 functions as a spacer between the overhanging portion 214 and the first ear mark 91, and the posture of the cover case 200 is stabilized. A height position (tip position) of the protruding portion 222 may be caused to coincide with a height position of the case main body portion 221. Therefore, the detection accuracy of vibration with a direction substantially orthogonal to the first surface S1 and the second surface S2 set as a reference direction is improved.

Note that the protruding portion 222 provided in the cover case 200 according to the present embodiment is an elongated protruding portion 222 with a predetermined length, but the shape of the protruding portion can be variously changed. For example, the protruding portion 222 may be divided into a plurality of parts. In addition, the protruding portion may not be provided in a straight line, and may be arranged in zigzag.

Note that since a light receiving unit of an optical power generation unit and a thermal contact of a temperature sensor are provided in each of the first surface S1 and the second surface S2 in the signal transmission device 10 according to the present embodiment, an orientation of the signal transmission device 10 accommodated in the cover case 200 is not particularly limited. However, for example, in a case in which the light emitting element 345 such as an LED is provided on the first surface S1, the signal transmission device 10 may be attached to an attachment target such that the first surface S1 faces a side opposite to the attachment target. In this case, the signal transmission device 10 is accommodated in the cover case 200 such that the second surface S2 faces the second half 220 side, and is attached to the first ear mark 91.

2-3. Functional Configuration of Signal Transmission Device

Figure 21:
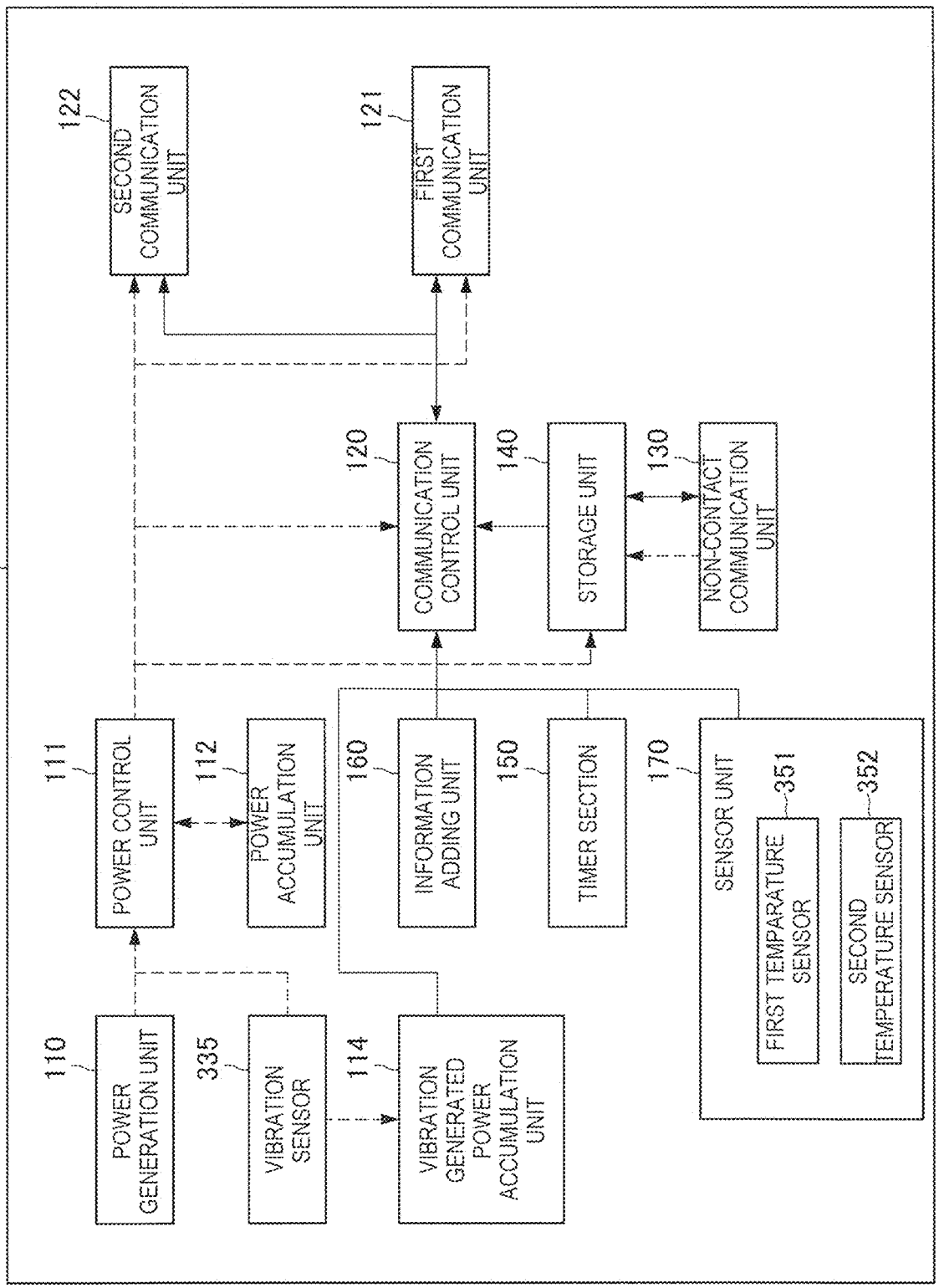
FIG. 21 is a block diagram which shows a functional configuration of the signal transmission device according to the embodiment.

Next, a functional configuration of the signal transmission device 10 according to the present embodiment will be described with reference to FIG. 21. FIG. 21 is a block diagram which shows the functional configuration of the signal transmission device 10 according to the present embodiment. AS shown in FIG. 21, the signal transmission device 10 includes a power generation unit 110, the vibration sensor 335, a power control unit 111, a power accumulation unit 112, a communication control unit 120, a first communication unit 121, a second communication unit 122, a non-contact communication unit 130, a storage unit 140, a timer section 150, an information adding unit 160, and a sensor unit 170.

(2-3-1. Power Generation Unit)

In the signal transmission device 10 according to the present embodiment, the power generation unit 110 includes the first optical power generation unit 311 and the second optical power generation unit 323 described above. In addition to these the power generation unit 110 may also include one or more of various types of power generation elements such as a thermoelectric conversion power generation element, an enzyme power generation element, a radio wave power generation element, and a near electromagnetic field power generation element.

For example, the thermoelectric conversion power generation element includes a power generation element using a Seebeck effect or a Thomson effect, a thermos-electronic power generation element, or a thermomagnetic power generation element, and is a power generation element that generates power using heat, a temperature difference, or the like. An enzyme power generation element is a power generation element that generates power by decomposing carbohydrates (for example, glucose and the like) contained in an organic matter and the like using enzymes. The radio wave power generation element is a power generation element that generates power using a radio wave such as Wi-Fi or terrestrial digital wave. The near electromagnetic field power generation element is a power generation element that generates power using, for example, an electromagnetic wave in a near field.

The power generation unit 110 includes at least the first optical power generation unit 311 and the second optical power generation unit 323, and thereby the signal transmission device 10 can transmit signals without having a power source mounted thereon. Note that power generated by the power generation unit 110 is accumulated in a power accumulation unit 112 to be described below.

(2-3-2. Vibration Sensor)

The vibration sensor 335 detects vibration occurring in the signal transmission device 10. The vibration sensor 335 of the signal transmission device 10 according to the present embodiment is configured using a piezoelectric element as an example, and generates power in accordance with occurring vibration. Therefore, the vibration sensor 335 also functions as a power generation element. Power generated by the vibration sensor 335 is accumulated in the power accumulation unit 112. In addition, a part of the power generated by the vibration sensor 335 is accumulated in a vibration power accumulation unit 114 as information (vibration information) indicating a presence or absence and a magnitude of vibration. The vibration power accumulation unit 114 may be a power storage device with a capacity smaller than that of the power accumulation unit 112 that accumulates power for communication. Power accumulated in the vibration power accumulation unit 114, that is, an inter-terminal voltage of the vibration power accumulation unit 114, changes in accordance with vibration detected by the vibration sensor 335, and a value of the voltage increases as the vibration detected by the vibration sensor 335 is larger or as the number of times of vibration increases. The inter-terminal voltage of the vibration power accumulation unit 114 can be added to a signal transmitted as vibration information, and can be reset whenever a signal is transmitted.

(2-3-3. Power Control Unit)

The power control unit 111 controls a supply of power to the first communication unit 121 and the second communication unit 122. The power control unit 111 may have a function realized by an IC mounted on the circuit board 331. Specifically, the power control unit 111 causes power generated by the power generation unit 110 and the vibration sensor 335 to be accumulated in the power accumulation unit 112. In addition, the power control unit 111 supplies power accumulated in the power accumulation unit 112 to the first communication unit 121 or the second communication unit 122 in a case in which the power accumulated in the power accumulation unit 112 reaches a predetermined amount. In a case in which the signal transmission device 10 functions as the signal transmission device 10A, the signal transmission device 10 can transmit a signal from the first communication unit 121 when an integrated value of the power generated by the power generation unit 110 and the vibration sensor 335 reaches a predetermined amount. The power control unit 111 may be an integrated circuit constituted by various types of circuits such as a switching element such as a transistor, a power control integrated circuit (IC), or a regulator circuit.

Note that, in a case in which the signal transmission device 10 functions as the signal relay device 10B or the master relay device 10C, the signal transmission device 10 transmits a signal received by the first communication unit 121 from the second communication unit 122 when the signal is received. At this time, the power control unit 111 may supply power supplied from a secondary battery or an external power source separately mounted to the second communication unit 122, and may supply the power accumulated in the power accumulation unit 112 to the second communication unit 122.

(2-3-4. Power Accumulation Unit)

The power accumulation unit 112 accumulates power generated by the power generation unit 110 and the vibration sensor 335. The power accumulated in the power accumulation unit 112 is used to cause the first communication unit 121 and the second communication unit 122 to operate. The power accumulation unit 112 may be one of various secondary batteries such as a lithium ion secondary battery, various capacitors such as an electric double layer capacitor or a lithium ion capacitor, and various capacitors such as a ceramic capacitor, a film capacitor, an aluminum electrolytic capacitor, and a tantalum capacitor, or a combination of a plurality of them. In the signal transmission device 10 according to the present embodiment, a capacitor mounted on the circuit board 135 functions as the power accumulation unit 112.

In addition, the power accumulation unit 112 may accumulate the power generated by the power generation unit 110 and the vibration sensor 335 by converting it into mechanical energy, thermal energy, light energy, or the like other than electric energy. In such a case, the signal transmission device 10 includes an energy conversion mechanism for converting electric energy into other types of energy, and a power accumulation device, a heat accumulation device, or a light accumulation device can be used as the power accumulation unit 112.

(2-3-5. Sensor Unit)

The sensor unit 170 includes various sensors that measure the state of livestock to which the signal transmission device 10A is attached, or the state of a surrounding environment of the livestock. In the signal transmission device 10A according to the present embodiment, the sensor unit 170 includes the first temperature sensor 351 and the second temperature sensor 353 described above. Information (sensor information) on a measurement value measured by the various sensors of the sensor unit 170 includes information (temperature information) detected by the first temperature sensor 351 and the second temperature sensor 353, and is added to a signal at the time of transmitting the signal from the first communication unit 121. As a result, the management system 1 can obtain not only the position of livestock to which the signal transmission device 10A is attached but also the state of livestock or the state of the surrounding livestock according to a signal from the signal transmission device 10A. Note that vibration information detected by the vibration sensor 335 can also be included in sensor information.

The sensor unit 170 may also include various sensors that measure the state of a surrounding environment such as a humidity sensor, a barometric pressure sensor, an illuminance sensor, a gas sensor, vibration sensors like an acceleration sensor and a gyro sensor, a geomagnetic sensor, a microphone, and an imaging device in addition to the first temperature sensor 351 and the second temperature sensor 353. In addition, the sensor unit 170 may be various sensors that measure the state of livestock such as a heart rate sensor, a blood sugar level sensor, and blood pressure sensor. Furthermore, the sensor unit 170 may be a combination of a plurality of types of sensors described above.

(2-3-6. First Communication Unit)

The first communication unit 121 includes a communication circuit and the first antenna 328, and transmits and receives signals in a first communication method. A communication circuit of the first communication unit 121 may be realized by an IC mounted on the circuit board 331. The first communication unit 121 may be a communication circuit and an antenna that perform communication using wavelength signals having bandwidths of hundreds MHz to several GHz (for example, 920 MHz and the like) such as Wi-Fi, ZigBee, Bluetooth, Bluetooth low energy, ANT, ANT+, and EnOcean Alliance, or mobile communication such as 3G or LTE. In the signal transmission device 10 according to the present embodiment, the first communication unit 121 includes a communication circuit and an antenna of Bluetooth Low Energy.

Note that the first communication method may be a communication method in which a communication available range is relatively short (for example, a communication available range is shorter than in a second communication method to be described below). In the management system 1 according to the present embodiment, the positions of the signal transmission device 10A and an attachment target to which the signal transmission device 10A is attached are ascertained using a positon of the signal relay device 10B which has received a signal transmitted by the first communication unit 121. For this reason, in a case in which the communication available range of the first communication method performed by the first communication unit 121 is relatively short, it is possible to ascertain the positions of the signal transmission device 10A and an attachment target with a higher resolution.

(2-3-7. Second Communication Unit)

The second communication unit 122 includes a communication circuit and a second antenna 329, and transmits and receives signals in a second communication method. The communication circuit of the second communication unit 122 may be realized by the IC mounted on the circuit board 331. The second communication unit 122 may be a communication circuit and an antenna that perform communication of wavelength signals having bandwidths of hundreds MHz to several GHz (for example, 920 MHz and the like) such as Wi-Fi, ZigBee, Bluetooth, Bluetooth low energy, ANT, ANT+, and EnOcean Alliance, or mobile communication such as 3G or LTE. In the signal transmission device 10 according to the present embodiment, the second communication unit 122 includes the communication circuit and the second antenna 329 for a communication method using a signal having a wavelength of 920 MHz.

The communication circuit and the second antenna 329 constituting the second communication unit 122 may be different from or the same as the communication circuit and the first antenna 328 constituting the first communication unit 121. For example, the communication circuit constituting the second communication unit 122 may be an IC or an electronic component common to the communication circuit constituting the first communication unit 121. In addition, the antenna constituting the second communication unit 122 may be a multi-band antenna common to the antenna constituting the first communication unit 121. Moreover, in a case in which a communication method or frequency in the second communication method performed by the second communication unit 122 is different from in the first communication method, the second communication unit 122 can prevent a transmitted signal from being confused with a signal transmitted from the first communication unit 121.

In addition, the second communication method performed by the second communication unit 122 may have a longer communication available range than in the first communication method. In a case in which the communication available range in the second communication method is longer than in the first communication method, the signal transmission device 10 can relay signals transmitted from the signal transmission device 10A to the master relay device 10C more efficiently as the signal relay device 10B.

(2-3-8. Communication Control Unit)

The communication control unit 120 controls transmission and reception of signals using the first communication unit 121 and the second communication unit 122 on the basis of communication control information stored in the storage unit 140. The communication control unit 120 may include, for example, an arithmetic processing unit such as a micro processing unit (MPU) or a central processing unit (CPU) mounted on the circuit board 331, and memories such as a read only memory (ROM) and a random access memory (RAM).

Specifically, the communication control unit 120 controls the first communication unit 121, in a case in which the signal transmission device 10 functions as the signal transmission device 10A, such that it transmits a signal including identification information, temperature information, and vibration information of the signal transmission device 10 using a predetermined amount of power accumulated in the power accumulation unit 112. That is, in a case in which power accumulated in the power accumulation unit 112 reaches a predetermined amount, the communication control unit 120 reads communication control information from the storage unit 140, and controls the first communication unit 121 such that it transmits a signal including various types of information on the basis of the read communication control information.

Note that the power accumulated in the power accumulation unit 112 is consumed once by the first communication unit 121 transmitting a signal, but is accumulated again as time elapses by the power generation unit 110 and the vibration sensor 335 generating power. For this reason, the communication control unit 120 may control the first communication unit 121 such that it transmits a signal whenever the power accumulated in the power accumulation unit 112 reaches a predetermined amount.

In addition, in a case in which the signal transmission device 10 functions as the signal relay device 10B or the master relay device 10C, the communication control unit 120 controls the first communication unit 121 such that it receives a signal transmitted from the first communication unit 121 of another signal transmission device 10.

Moreover, in a case in which the signal transmission device 10 functions as the signal relay device 10B or the master relay device 10C, the communication control unit 120 controls the second communication unit 122 such that it receives a signal transmitted from the second communication unit 122 of another signal transmission device 10 (that is, the signal relay device 10B). In addition, the communication control unit 120 controls the second communication unit 122 such that it transmits a signal from the signal transmission device 10 (that is, the signal transmission device 10A) received by the first communication unit 121 to a next signal relay device 10B or master relay device 10C. Furthermore, the communication control unit 120 controls the second communication unit 122 such that it transmits only a signal whose identification information coincides with its own identification information among signals from the signal transmission device 10 (that is, the signal relay device 10B) received by the second communication unit 122 to a next signal relay device 10B or master relay device 10C. Note that the communication control unit 120 performs control such that transmission and reception by the second communication unit 122 are not performed in a case in which the signal transmission device 10 functions as the signal transmission device 10A.

(2-3-9. Timer Section)

The signal transmission device 10 may include a timer section 150. The timer section 150 is, for example, an analog or digital time counter, and measures time. The timer section 150 may be used, for example, to adjust a signal transmission interval by the first communication unit 121. For example, in a case in which the signal transmission device 10 functions as the signal transmission device 10A, the communication control unit 120 may adjust a signal transmission interval of the first communication unit 121 on the basis of time measured by the timer section 150.

For example, in a case in which power generation by the power generation unit 110 is active, there is a possibility that the power accumulated in the power accumulation unit 112 reaches a predetermined amount in a short time (for example, less than 1 second). In such a case, a frequent transmission of signals from the first communication unit 121 may increase a processing load on each device of the management system 1 and decrease a processing capability of the management system 1. For this reason, the communication control unit 120 sets a threshold value with an interval at which the first communication unit 121 transmits a signal, and permits the first communication unit 121 to transmit a signal in a case in which time equal to or greater than a threshold value has passed since the first communication unit 121 has transmitted a signal. The threshold value with an interval at which the first communication unit 121 transmits a signal can be appropriately set, and may be, for example, about 10 seconds, 20 seconds, or 30 seconds. The threshold value described above may be set, for example, in the communication control information stored in the storage unit 140.

For example, the timer section 150 is a time counter in which an integrated value is reset each time the first communication unit 121 transmits a signal, and measures elapsed time since the first communication unit 121 transmits a signal. Note that, in a case in which the signal transmission device 10 operates only using power generated by the power generation unit 110 and the vibration sensor 335, the signal transmission device 10 is in an energized state when the first communication unit 121 transmits a signal, and is in an un-energized state after the transmission of a signal. For this reason, the timer section 150 may be an analog timer capable of measuring an elapsed time even in the un-energized state. The analog timer is, for example, a timer that prohibits the transmission of a signal by the first communication unit 121 until the power accumulated in the power accumulation unit 112 falls below a predetermined threshold value after the power accumulated in the power accumulation unit 112 exceeds a predetermined amount and the first communication unit 121 starts to transmit a signal.

(2-3-10. Information Adding Unit)

An information adding unit 160 adds information to a signal received by the first communication unit 121 or the second communication unit 122. Specifically, in a case in which the signal transmission device 10 functions as the signal relay device 10B, the information adding unit 160 adds identification information of the signal transmission device 10 (that is, the signal relay device 10B) which has received a signal to the signal received by the first communication unit 121. As a result, in the information processing device 30, it is possible to specify the signal transmission device 10 (that is, the signal relay device 10B) which has received a signal transmitted by the first communication unit 121 of the signal transmission device 10A. Since the signal transmission device 10 functioning as the signal relay device 10B is installed to be fixed at a predetermined position, and the position is ascertained, the information processing device 30 can ascertain the position of the signal transmission device 10A on the basis of the position of the signal relay device 10B. On the other hand, in a case in which the signal transmission device 10 functions as the signal transmission device 10A, functions of the information adding unit 160 can be omitted.

Note that the information adding unit 160 may be constituted by, for example, an arithmetic processing unit such as an MPU or a CPU and memories such as a ROM and a RAM.

In addition, the information adding unit 160 may add information related to radio wave intensity of a received signal to the signal transmitted by the first communication unit 121 of another signal transmission device 10. As a result, since a distance between the signal transmission device 10A which has transmitted a signal and the signal relay device 10B which has received the signal can be estimated on the basis of the radio wave intensity of the signal, it is possible to more accurately ascertain the position of the signal transmission device 10A. Note that information related to the radio wave intensity of a received signal may have three stages such as "strong," "normal," and "weak."

Moreover, the information adding unit 160 may add identification information of the signal transmission device 10 (that is, the signal relay device 10B) serving as a next receiver of a signal to the signal received by the first communication unit 121. For example, in a case in which a signal transmitted from the signal transmission device 10A is transmitted to the master relay device 10C through a plurality of signal relay devices 10B, a signal transmission path in each of the signal relay devices 10B may be specified to prevent occurrence of any confusion. Therefore, the information adding unit 160 adds the identification information of a signal transmission device 10 serving as a next receiver of a signal (that is, a second signal relay device 10B) to the signal, thereby specifying the transmission path of the signal. As a result, since a signal transmitted from the signal transmission device 10A can be transmitted to the master relay device 10C through the plurality of signal relay devices 10B in the management system 1, it is possible to ascertain the position of the signal transmission device 10A in a wider area.

Furthermore, in a case in which the signal transmission device 10 functions as the second and subsequent signal relay device 10B, the information adding unit 160 may update the identification information of the signal transmission device 10 serving as a next receiver of a signal included in the received signal. As a result, since the information adding unit 160 can designate a signal relay device 10B serving as a next receiver, it is possible to relay a signal over a longer distance by repeating relaying of the signal and transmit it to the master relay device 10C.

(2-3-11. Non-Contact Communication Unit)

The non-contact communication unit 130 receives communication control information using a non-contact communication, writes the communication control information in the storage unit 140, or rewrites the communication control information stored in the storage unit 140. Note that the communication control information is information used when the communication control unit 120 controls the transmission and reception of the first communication unit 121 and the second communication unit 122. The non-contact communication unit 130 may communicate with the outside using, for example, a communication method used in an RFID or an NFC, and may receive the communication control information. In this case, the non-contact communication unit 130 includes the non-contact communication antenna 315 and a communication circuit corresponding to the communication method used in an RFID or the NFC. The communication circuit may be realized by the IC mounted on the circuit board 331.

Specifically, the non-contact communication unit 130 receives communication control information in a non-contact communication, and applies power supplied to a received carrier wave to the storage unit 140, thereby rewriting the communication control information stored in the storage unit 140. According to the non-contact communication unit 130, the signal transmission device 10 can rewrite the communication control information stored in the built-in storage unit 140, a control program of the signal transmission device 10, and the like without providing switches, contacts, terminals, or the like in the housing.

(2-3-12. Storage Unit)

The storage unit 140 stores communication control information for controlling the transmission and reception of a signal by the signal transmission device 10. Specifically, the storage unit 140 may store identification information unique to the signal transmission device 10, information for controlling whether to permit transmission and reception of a signal by the signal transmission device 10, information related to various settings of the signal transmission device 10, and the like as communication control information. Note that the storage unit 140 is constituted by a non-volatile memory. As the non-volatile memory, for example, a flash memory, a ferroelectric random access memory (FeRAM), a magnetic random access memory (MRAM), a phase change random access memory (PCRMA), or the like can be used.

Note that power generated by the power generation unit 110 and power transmitted from the outside to the non-contact communication unit 130 are applied to the storage unit 140, and thereby a reading operation or rewriting operation of the stored information is performed in the storage unit 140. Specifically, power generated by the power generation unit 110 and accumulated in the power accumulation unit 112 is applied to the storage unit 140, and thereby the communication control information stored in the storage unit 140 is read. The read communication control information is used for control of the first communication unit 121 and the second communication unit 122 in the communication control unit 120. In addition, power transmitted using a carrier wave received by the non-contact communication unit 130 is applied to the storage unit 140, and thereby the communication control information stored in the storage unit 140 is rewritten using rewriting information received by the non-contact communication unit 130.

For example, the storage unit 140 may store information of each of items shown in FIG. 22. FIG. 22 is an explanatory diagram which shows an example of information stored in the storage unit 140.

As shown in FIG. 22, for example, the storage unit 140 may store version information of hardware of the signal transmission device 10, and may store version information of software (that is, firmware) of the signal transmission device 10. In addition, the storage unit 140 may also store identification information unique to the signal transmission device 10. In addition, the storage unit 140 may store reception control information indicating whether or not the signal transmission device 10 receives a signal as "0" or "1", and may store transmission control information indicating whether or not the signal transmission device 10 transmits a signal as "0" or "1". Note that these types of control information correspond to communication control information, "0" represents that the function is off, and "1" represents that the function is on.

Note that the reception control information and the transmission control information may be stored in the storage unit 140 in a form other than the above. For example, the reception control information is information indicating an object to be subjected to reception processing, and may be information indicating one of "performing only in the first communication unit 121," "performing only in the second communication unit 122," "performing in both the first communication unit 121 and the second communication unit 122," and "performing in neither the first communication unit 121 nor the second communication unit 122." In addition, the transmission control information is information indicating an object to be subjected to transmission processing, and may be information indicating one of "performing only in the first communication unit 121," "performing only in the second communication unit 122," "performing in both the first communication unit 121 and the second communication unit 122," and "performing in neither the first communication unit 121 nor the second communication unit 122."

Furthermore, the storage unit 140 may store destination information used in a case in which the signal transmission device 10 functions as the signal relay device 10B. The destination information is information indicating which signal relay device 10B is a next receiver to receive a signal transmitted from the signal relay device 10B, and specifically includes the identification information of a signal relay device 10B serving as a receiver. The signal relay device 10B or the master relay device 10C whose identification information coincides with the identification information included in the destination information transmits a received signal according to the second communication method to the signal relay device 10B or the network connection device 20 serving as a next destination.

2-4. Operation of Signal Transmission Device

Next, an operation of the signal transmission device 10 according to the present embodiment will be described with reference to FIGS. 23 to 28.

(2-4-1. Basic Operation of Signal Transmission Device)

Figure 23:
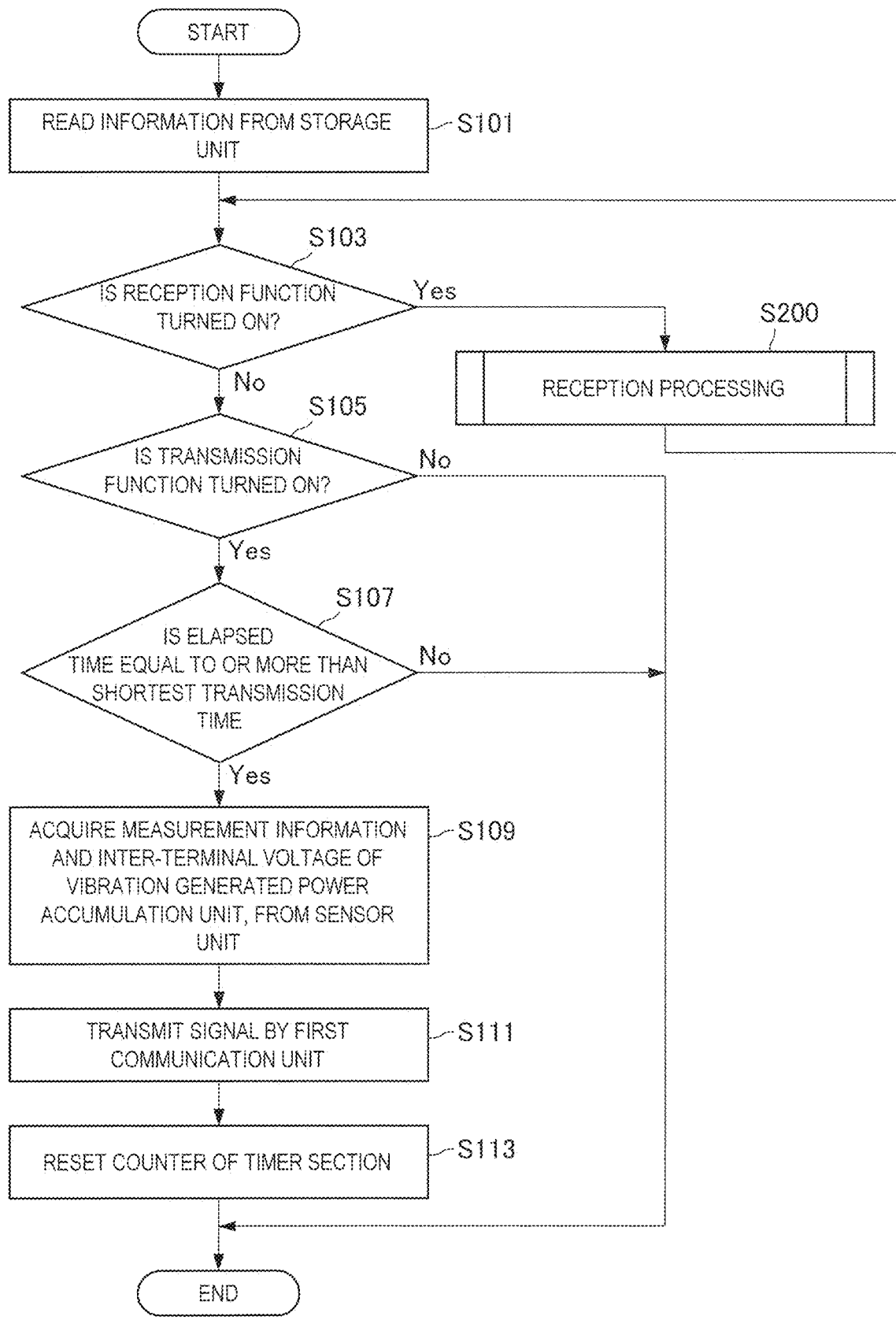
FIG. 23 is a flowchart which describes an example of a basic operation of the signal transmission device.

First, a basic operation of the signal transmission device 10 will be described with reference to FIGS. 23 to 24. FIG. 23 is a flowchart which describes an example of the basic operation of the signal transmission device 10. In addition, FIG. 24 is an explanatory diagram in which an example of information included in a signal transmitted by the signal transmission device 10A is shown.

As shown in FIG. 23, the signal transmission device 10 is activated using power accumulated in the power accumulation unit 112 or power from an external power source. Specifically, the power control unit 111 supplies the power accumulated in the power accumulation unit 112 to the communication control unit 120 and the storage unit 140. Thereafter, the communication control unit 120 reads communication control information from the storage unit 140 using the supplied power (S101). Note than the power control unit 111 may supply power to the storage unit 140 via the communication control unit 120. Next, the communication control unit 120 determines whether or not a reception function of each of the first communication unit 121 and the second communication unit 122 is ON on the basis of the read communication control information (S103). In a case in which the reception function of at least one of the first communication unit 121 and the second communication unit 122 is ON (Yes in S103), the communication control unit 120 causes the first communication unit 121 or the second communication unit 122 to shift to a reception standby state, and performs reception processing (S200). At this time, the signal transmission device 10 functions as the signal relay device 10B or the master relay device 10C.

On the other hand, in a case in which the reception functions of the first communication unit 121 and the second communication unit 122 are OFF (No in S103), the communication control unit 120 determines whether or not a transmission function of the first communication unit 121 is ON on the basis of the read communication control information (S105). In a case in which the transmission function of the first communication unit 121 is ON (Yes in S103), the communication control unit 120 determines whether or not time measured by the timer section 150 is equal to or greater than a threshold value set as the shortest transmission time (S107). In a case in which time equal to or greater than the shortest transmission time has elapsed (Yes in S107), the communication control unit 120 reads various types of measurement information from the sensor unit 170 and reads an inter-terminal voltage V of the vibration power accumulation unit 114 (S109). Next, the communication control unit 120 controls the first communication unit 121 such that it transmits a signal including various types of read information and the identification information of the signal transmission device 10 (S111).

Figure 25:
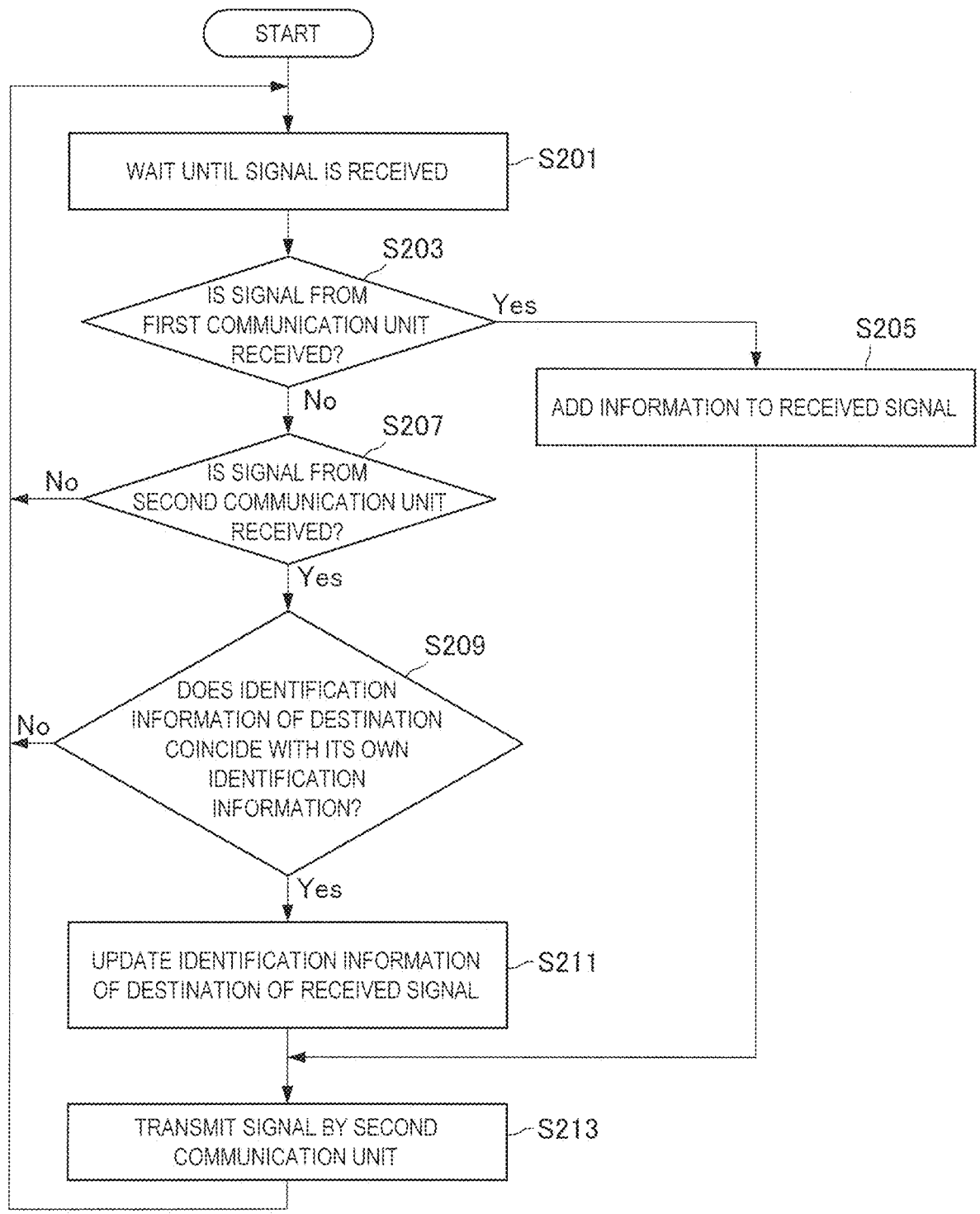
FIG. 25 is a flowchart which describes an example of an operation in a case in which the signal transmission device functions as a signal relay device.
Figure 27:
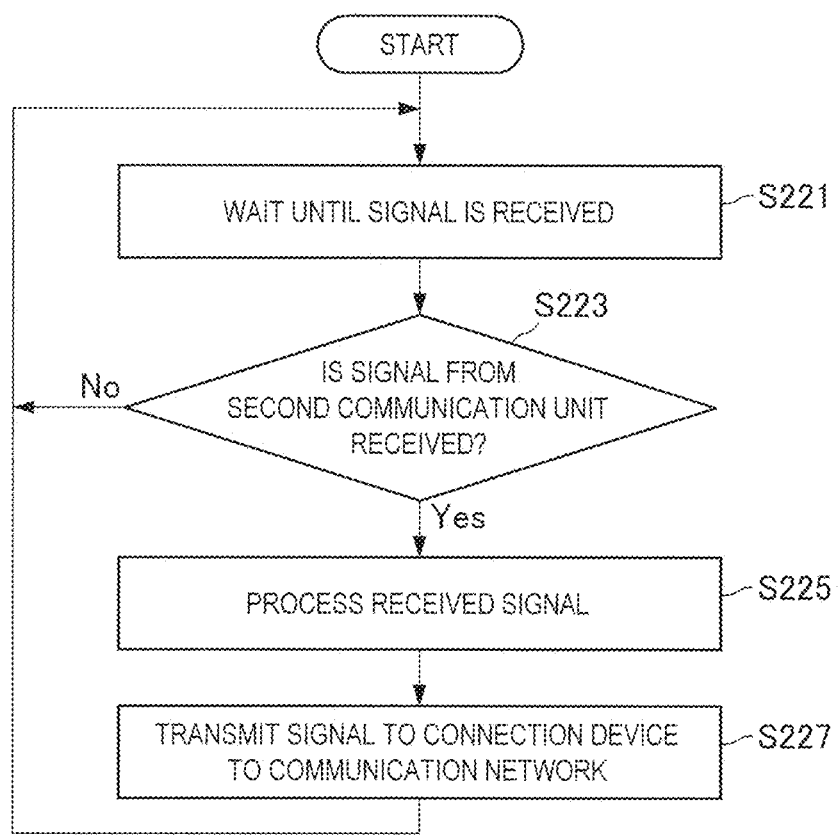
FIG. 27 is a flowchart which describes an example of an operation in a case in which the signal transmission device functions as a master relay device.

Note that, in a case in which the transmission function of the first communication unit 121 is ON, and the transmission function of the second communication unit 122 is OFF, a positive determination is made in step S103 (Yes in S103). In this case, the signal transmission device 10 functions as the signal transmission device 10A, and executes the operations described above. In addition, in a case in which the transmission function of the first communication unit 121 is ON, and the transmission function of the second communication unit 122 is ON, a positive determination is made in step S103 (Yes in S103). In this case, the signal transmission device 10 functions as the signal transmission device 10A and the signal relay device 10B, and executes the operations described above and operations to be described below as shown in FIG. 25. In addition, in a case in which the transmission function of the first communication unit 121 is OFF, and the transmission function of the second communication unit 122 is ON, a negative determination is made in step S103 (No in S103). In this case, the signal transmission device 10 functions as the signal relay device 10B or the master relay device 10C, and executes operations to be described below as shown in FIG. 25 or 27. Furthermore, in a case in which the transmission function of the first communication unit 121 is OFF, and the transmission function of the second communication unit 122 is OFF, a negative determination is made in step S103 (No in S103). In this case, the signal transmission device 10 is in a state in which the function is stopped, and the communication control unit 120 ends the operation.

Here, an example of information included in a signal transmitted by the signal transmission device 10 functioning as the signal transmission device 10A in S111 is shown in FIG. 24. As shown in FIG. 24, the signal transmitted by the signal transmission device 10A may also include, for example, data format information of a signal indicating what type of information is included in a signal, identification information for identifying a signal transmission device 10 which has transmitted a signal, and various types of measurement information measured by the sensor unit 170. Various types of measurement information include information of a first temperature T1 detected by the first temperature sensor 351, information of a second temperature T2 detected by the second temperature sensor 353, and vibration information detected by the vibration sensor 335. In a case in which the signal transmission device 10A includes a sensor other than the temperature sensor, measurement information detected by the sensor can also be included in a signal transmitted by the signal transmission device 10A.

Thereafter, the communication control unit 120 resets a counter of the timer section 150, and starts measurement of time after transmitting a signal (S113). At this time, the signal transmission device 10 functions as the signal transmission device 10A. Note that, in a case in which the transmission function of the first communication unit 121 is OFF (No in S105), or in a case in which time equal to or more than the shortest transmission time has not elapsed since a previous signal is transmitted (No in S107), the communication control unit 120 ends the operation and does not perform the transmission of a signal from the first communication unit 121.

(2-4-2. Operation of Signal Relay Device)

Next, an example of an operation in a case in which the signal transmission device 10 functions as the signal relay device 10B will be described with reference to FIGS. 25 and 26. FIG. 25 is a flowchart which describes an example of the operation in a case in which the signal transmission device 10 functions as the signal relay device 10B. In addition, FIG. 26 is an explanatory diagram in which an example of information included in a signal transmitted by the signal relay device 10B is shown. Note that the operation in a case in which the signal transmission device 10 functions as the signal relay device 10B corresponds to the operation of the reception processing shown in S200 of FIG. 23.

As shown in FIG. 25, in the reception processing (S200), first, the communication control unit 120 causes the first communication unit 121 and the second communication unit 122 to wait in a reception standby state until a signal is received (S201). Next, the communication control unit 120 determines whether or not a signal from another signal transmission device 10 has been received by the first communication unit 121 (S203). In a case in which a signal has been received by the first communication unit 121 (Yes in S203), the communication control unit 120 controls the information adding unit 160 such that it adds information to the signal (S205), and thereafter the communication control unit 120 controls the second communication unit 122 such that it transmits the signal added with information (S213).

Here, examples of the information added by the information adding unit 160 include, for example, the identification information of the signal transmission device 10 which has received a signal, information related to the radio wave intensity of a received signal, the identification information of the signal transmission device 10 serving as a next receiver of a signal, and the like. In addition, the information adding unit 160 may add information related to a time at which a signal has been received, information related to a communication method of a received signal, and the like.

On the other hand, in a case in which a signal is not received by the first communication unit 121 (No in S203), the communication control unit 120 determines whether or not the second communication unit 122 has received a signal from another signal transmission device 10 (S207). In a case in which a signal is received by the second communication unit 122 (Yes in S207), the communication control unit 120 determines whether or not the identification information of the signal transmission device 10 serving as a receiver of the received signal coincides with its own identification information (S209). In a case in which the identification information of the signal transmission device 10 serving as a receiver of the signal coincides with its own identification information (Yes in S209), the communication control unit 120 causes the identification information of the signal transmission device 10 serving as a next receiver of a signal to be updated by controlling the information adding unit 160 (S211), and controls the second communication unit 122 such that it transmits a signal with updated information (S213).

Here, an example of information included in a signal transmitted by the signal transmission device 10 functioning as the signal relay device 10B in S213 will be shown in FIG. 26. As shown in FIG. 26, the signal transmitted by the signal relay device 10B includes, for example, in the same manner as in FIG. 24, data format information of a signal indicating what type of information is included in a signal, identification information for identifying a signal transmission device 10 which has transmitted a received signal, and various types of measurement information measured by a sensor unit. Various types of measurement information include information of the first temperature T1 detected by the first temperature sensor 351, information of the second temperature T2 detected by the second temperature sensor 353, and vibration information detected by the vibration sensor 335. In addition, the signal transmitted by the signal relay device 10B may include, for example, identification information for identifying a signal transmission device 10 serving as a next receiver, identification information for identifying a signal transmission device 10 which has received a signal, information indicating time at which a signal is received, and information indicating the radio wave intensity of a received signal. These types of information are information added to a signal by the signal relay device 10B.

Thereafter, the signal transmission device 10 returns to the reception standby state of a signal (S201). As a result, the signal transmission device 10 can function as the signal relay device 10B. Note that, in a case in which a signal is not received by the second communication unit 122 (No in S207), or in a case in which the identification information of the signal transmission device 10 serving as a receiver is different from its own identification information (No in S209), the signal transmission device 10 ends the operation temporarily, and returns to the reception standby state of a signal (S201).

(2-4-3. Operation of Master Relay Device)

Next, an example of an operation in a case in which the signal transmission device 10 functions as the master relay device 10C will be described with reference to FIGS. 27 and 28. FIG. 27 is a flowchart which describes an example of the operation in a case in which the signal transmission device 10 functions as the master relay device 10C. In addition, FIG. 28 is an explanatory diagram in which an example of information included in a signal transmitted from the master relay device 10C to the network connection device 20 is shown. Note that the operation in a case in which the signal transmission device 10 functions as the master relay device 10C corresponds to the operation of the reception processing shown in S200 of FIG. 24.

As shown in FIG. 27, in the reception processing (S200), the communication control unit 120 first causes the second communication unit 122 to wait in the reception standby state until a signal is received (S221). Next, the communication control unit 120 determines whether or not the second communication unit 122 has received a signal from another signal transmission device 10 (S223). In a case in which a signal is received by the second communication unit 122 (Yes in S223), the communication control unit 120 causes information included in a signal to be processed by controlling the information adding unit 160 (S225).

Here, the information adding unit 160 deletes identification information for identifying a signal transmission device serving as a next receiver from a received signal in S225. The identification information for identifying a signal transmission device serving as a next receiver is information for relaying a signal, and is not used for managing of the signal transmission device 10A, and thus an amount of information of a signal can be reduced by deleting the information.

Next, the communication control unit 120 controls the first communication unit 121 or the second communication unit 122 such that it transmits a processed signal to the network connection device 20 connected to the communication network 40 (S227). Here, an example of information included in a signal transmitted by the signal transmission device 10 functioning as the master relay device 10C in S227 is shown in FIG. 28. As shown in FIG. 28, the signal transmitted by the master relay device 10C includes, for example, in the same manner as in FIG. 26, data format information of a signal indicating the type of information included in a signal, identification information for identifying a signal transmission device which has transmitted a signal, and various types of measurement information measured by a sensor unit. The measurement information can include at least information of the first temperature T1, information of the second temperature T2, and vibration information.

In addition, the signal transmitted by the master relay device 10C may also include, for example, in the same manner as FIG. 26, identification information for identifying a signal transmission device 10 which has received a signal, information indicating time at which a signal is received, and information indicating the radio wave intensity of a received signal. Note that since identification information for identifying a signal transmission device serving as a next receiver is deleted in S225, it is not included in a signal transmitted by the master relay device 10C.

Thereafter, the signal transmission device 10 returns to the reception standby state of a signal (S221). Note that, in a case in which a signal is not received by the second communication unit 122 (No in S223), the signal transmission device 10 ends the operation temporarily, and returns to the reception standby state of a signal (S221). As a result, the signal transmission device 10 can function as the master relay device 10C.

3. INFORMATION PROCESSING DEVICE

Next, the information processing device 30 which receives a signal transmitted from the signal transmission device 10 via the communication network 40, and obtains the state of an object to which the signal transmission device 10A is attached will be described. The information processing device 30 may be, for example, an information processing server, but the present disclosure is not limited to this example. The information processing device 30 may also be an information terminal such as a tablet terminal.

3-1. Functional Configuration of Information Processing Device

Figure 29:
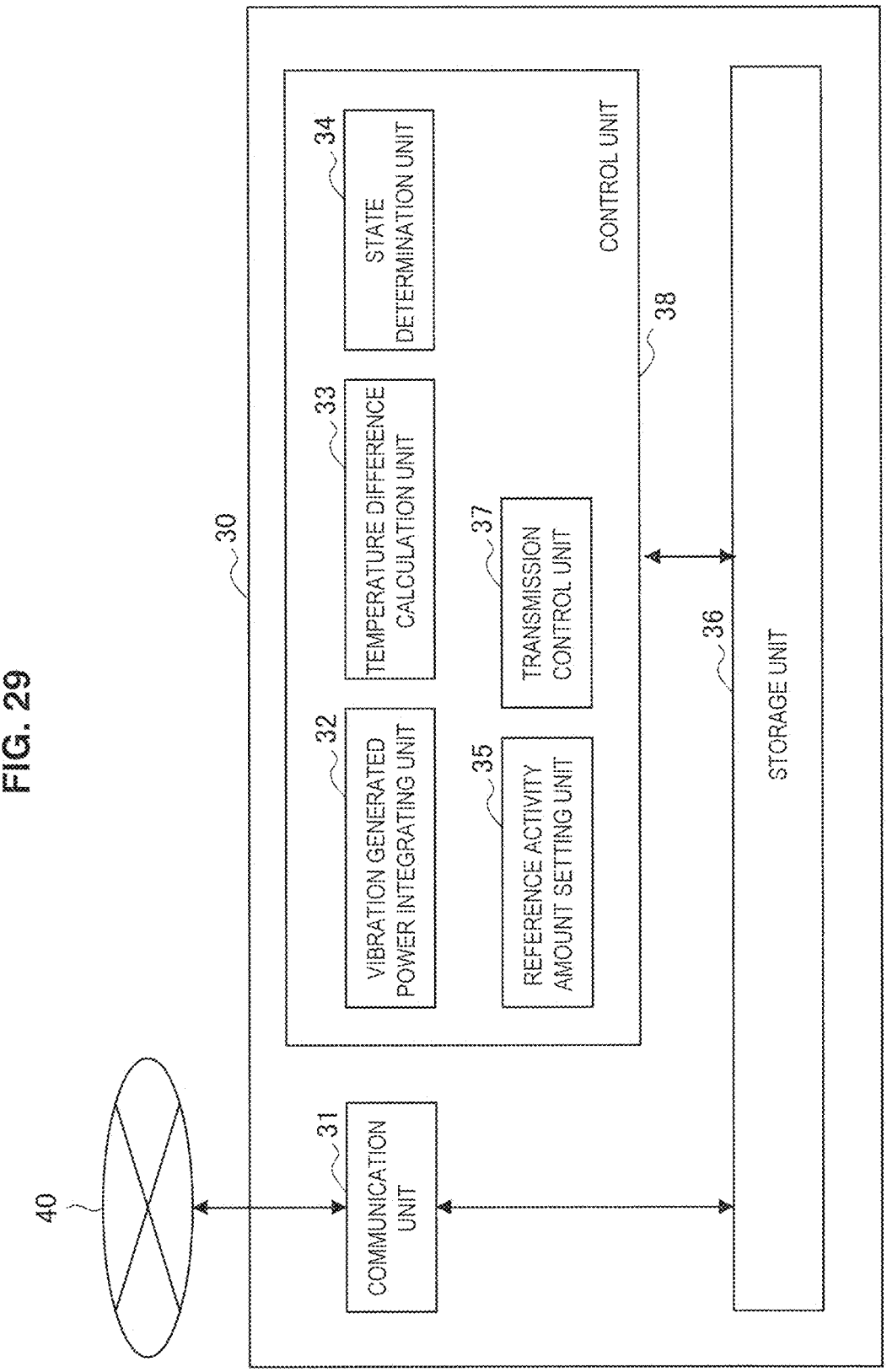
FIG. 29 is a block diagram which shows an example of a functional configuration of an information processing device of the management system according to the embodiment.

First, a functional configuration of the information processing device 30 of the management system 1 according to the present embodiment will be described with reference to FIG. 29. FIG. 29 is a block diagram which shows the functional configuration of the management system 1. As shown in FIG. 29, the information processing device 30 includes a communication unit 31, a control unit 38, and a storage unit 36. The control unit 38 includes a vibration generated power integrating unit 32, a temperature difference calculation unit 33, a state determination unit 34, a reference activity amount setting unit 35, a transmission control unit 37. The control unit 38 includes, for example, an arithmetic processing device such as CPU, and a storage element such as a ROM or RAM. The function of each unit may be realized by the arithmetic processing device executing a program stored in the storage element.

(3-1-1. Storage Unit)

The storage unit 36 stores various types of information such as information received via the communication unit 31, parameters used for arithmetic operations of other respective units, or results of the arithmetic operations. The storage unit 36 may also include at least one of a ROM, a RAM, a storage device, and a removable recording medium. Furthermore, a storage medium may be a storage server connected to the information processing device 30 via the communication network 40.

(3-1-2. Communication Unit)

The communication unit 31 receives a signal transmitted from the signal transmission device 10A, the signal relay device 10B, and the master relay device 10C via the communication network 40, and causes information included in the signal to be stored in the storage unit 36. The communication unit 31 includes a communication circuit, and a wired or wireless appropriate communication device, and can be connected to the communication network 40. The stored information can include, for example, identification information for identifying the signal transmission device 10 which has transmitted a signal, information of a first temperature T1, information of a second temperature T2, and vibration information detected by the first temperature sensor 351, the second temperature sensor 353, and the vibration sensor 335, respectively, information indicating time at which a signal is received, and the like. The vibration information may be, for example, a value of the inter-terminal voltage V of the vibration power accumulation unit 114 in which a part of the vibration generated power is accumulated. In a case in which the signal transmission device 10A includes a sensor other than the temperature sensor, the signal received by the communication unit 31 can include measurement information detected by the sensor.

(3-1-3. Transmission Control Unit)

The transmission control unit 37, for example, causes the communication unit 31 to output notification information for controlling notification in the information terminals 60 and 70 managed by a user such as the rancher 3A or the veterinarian 3B via the communication network 40. For example, the transmission control unit 37 may cause notification information for notifying the information terminals 60 and 70 managed by a user of information of the state of livestock obtained on the basis of a reception signal to be transmitted. In addition, the transmission control unit 37 causes the notification information for notifying the information terminals 60 and 70 of the state information of livestock to be transmitted in accordance with an access from the information terminals 60 and 70 managed by a user. Furthermore, the transmission control unit 37 may receive a notification request from an information terminal of a user to an information terminal of another user, and cause notification information for controlling notification to be transmitted to the information terminal of another user. Notification can be made in various methods such as an image display, a sound output, or lighting of the light source. Accordingly, a user such as the rancher 3A or the veterinarian 3B who has received a notification can ascertain the state of each head of livestock.

(3-1-4. Vibration Generated Power Integrating Unit)

The vibration generated power integrating unit 32 obtains information (activity information) on the activity amount of livestock on the basis of the vibration information stored in the storage unit 36. In the present embodiment, an integrated value of generated power caused by vibration is obtained as activity information. For example, the vibration generated power integrating unit 32 may obtain an integrated value of the inter-terminal voltage V of vibration generated power generated by the vibration sensor 335 in a predetermined unit time set in advance and accumulated in the vibration power accumulation unit 114. For example, since an amount of power generated by the first optical power generation unit 311 and the second optical power generation unit 323 is large during a time zone in which the sun can radiate, and a signal is transmitted at an appropriate frequency from the signal transmission device 10A, the vibration information correlating with the activity amount of livestock can be sequentially transmitted to the information processing device 30. On the other hand, since the amount of power generated by the first optical power generation unit 311 and the second optical power generation unit 323 is small during a time zone in which the sun does not radiate, and a transmission interval of a signal from the signal transmission device 10A is long, the information processing device 30 cannot ascertain accurately the vibration information in some cases.

For this reason, the vibration generated power integrating unit 32 performs calculation processing to be able to distinguish between a daytime time zone in which the sun can radiate and a nighttime time zone in which the sun hardly radiates. For example, the vibration generated power integrating unit 32 may set time from 8 o'clock to 15 o'clock as a unit time and integrate vibration information (inter-terminal voltage V) included in signals transmitted at the unit time every day. Alternatively, the vibration generated power integrating unit 32 may divide the time from 8 o'clock to 14 o'clock every two hours, set respective periods from 8 o'clock to 10 o'clock, 10 o'clock to 12 o'clock, and 12 o'clock to 14 o'clock as a unit time, and integrate vibration information (inter-terminal voltage V) included in signals transmitted at the unit time. The calculated voltage integrated value ∫V is output to and stored in the storage unit 36.

(3-1-5. Temperature Difference Calculation Unit)

The temperature difference calculation unit 33 obtains metabolic information of livestock on the basis of the information of a first temperature T1 and the information of a second temperature T2 stored in the storage unit 36. In the present embodiment, a temperature difference ΔT is obtained as the metabolic information. The temperature difference calculation unit 33 obtains the temperature difference ΔT between a first temperature T1 and a second temperature T2 included in each signal transmitted from the signal transmission device 10A, and causes it to be output to and stored in the storage unit 36. A healthy livestock has a large metabolism and a big temperature difference ΔT. The temperature difference ΔT between a first temperature T1 and a second temperature T2 included in each of received signals may be individually stored in the storage unit 36, and for example, an integrated value ∫T obtained by integrating temperature differences ΔT on a day basis may be stored in the storage unit 36.

Note that, in the signal transmission device 10 according to the present embodiment, since a light receiving unit of an optical power generation unit and thermal contact of a temperature sensor are provided on the first surface S1 and the second surface S2, respectively, when the signal transmission device 10 is mounted on livestock, any of the first face S1 and the second surface S2 may be oriented to livestock side. Therefore, the temperature difference calculation unit 33 may obtain an absolute value of a temperature difference ΔT between a first temperature T1 and a second temperature T2, and cause it to be stored in the storage unit 36.

(3-1-6. State Determination Unit)

The state determination unit 34 determines the state of livestock on the basis of the voltage integrated value ∫V stored in the storage unit 36 and information of the temperature difference ΔT. For example, the voltage integrated value ∫V obtained on basis of the vibration information correlates with the activity amount of livestock, and the activity amount of livestock correlates with an estrus state. In addition, the temperature difference ΔT obtained on the basis of temperature information correlates with the metabolism of livestock, and the metabolism correlates with a childbirth state. For this reason, the state determination unit 34 determines the state of livestock on the basis of the voltage integrated value ∫V obtained on the basis of vibration information and information of the temperature difference ΔT obtained on the basis of temperature information. The state determination unit 34 performs processing of outputting information of the determined state of livestock. For example, the state determination unit 34 performs processing of outputting and recording the state information of livestock to the storage unit 36. In addition, the information of the state of livestock can be transmitted to the information terminals 60 and 70 together with the identification number of the signal transmission device 10A or the identification number of livestock as notification information. The notification information may be provided in response to an access from the information terminals 60 and 70 of the rancher 3A or the veterinarian 3B. As a result, the rancher 3A or the veterinarian 3B can ascertain biological information of each head of livestock, and use it to determine the presence or absence of livestock requiring diagnosis and the like.

Figure 30:
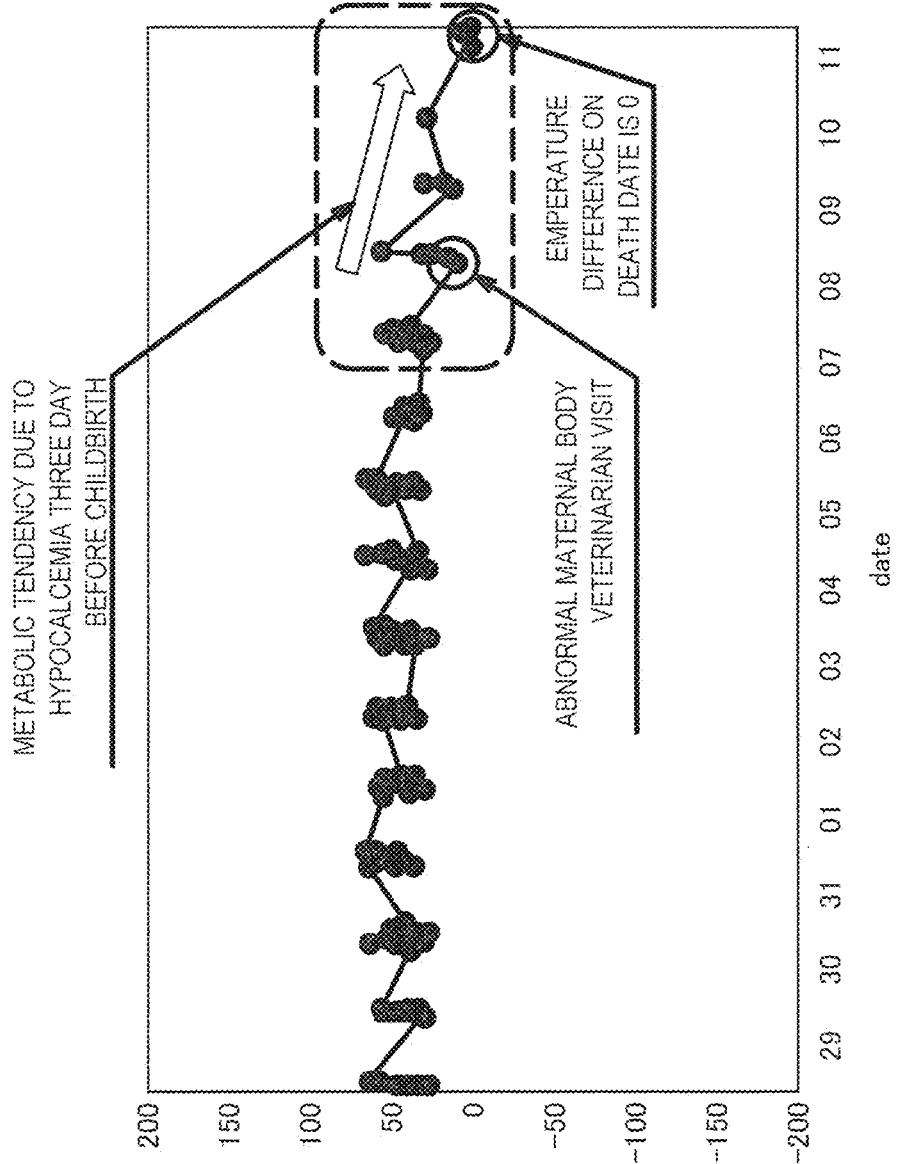
FIG. 30 is an explanatory diagram which shows a relationship between changes in metabolic rate and states of livestock (dairy cattle).

FIG. 30 shows a change in the temperature difference ΔT between a first temperature T1 detected on the body surface side of dairy cattle and a second temperature T2 detected toward a side opposite to the body surface side. A metabolic rate of dairy cattle replaced with the temperature difference ΔT and displayed shows that metabolism decreases due to hypocalcemia 3 days before childbirth, and thereafter, metabolism continues to weaken and the temperature difference ΔT becomes zero on the day of death. Therefore, it can be known that it is appropriate to regard the temperature difference ΔT between a first temperature T1 and a second temperature T2 as the metabolic rate of dairy cattle.

3-2. Hardware Configuration of Information Processing Device

Figure 31:
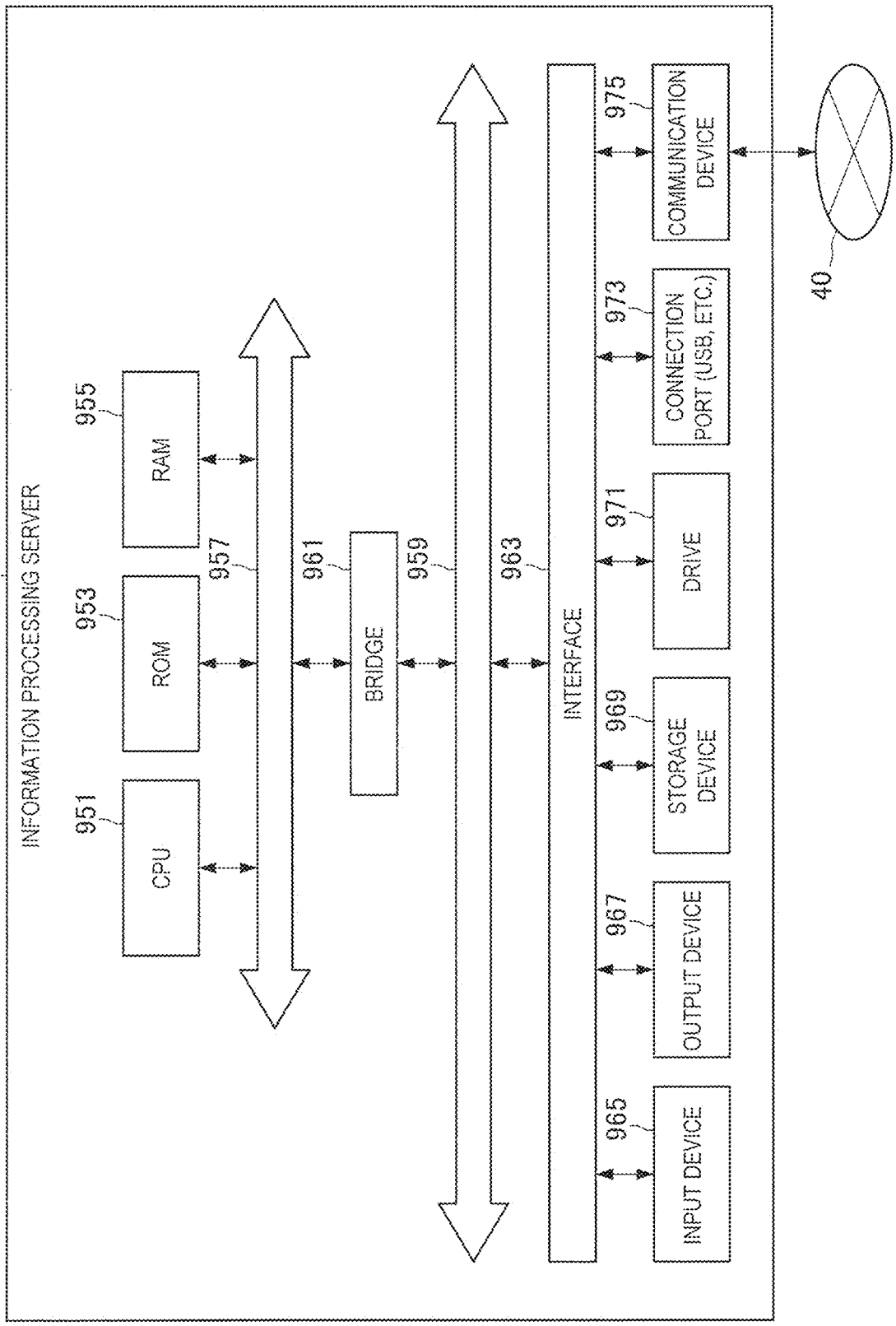
FIG. 31 is a block diagram which shows an example of a hardware configuration of the information processing device of the management system according to the embodiment.

Next, a hardware configuration of the information processing device 30 according to the present embodiment will be described with reference to FIG. 31. FIG. 31 is a block diagram which shows an example of the hardware configuration of the information processing device 30 according to the embodiment. Note that information processing by the information processing device 30 according to the present embodiment is realized by cooperation between software and hardware.

As shown in FIG. 31, the information processing device 30 includes a CPU 951, a ROM 953, a RAM 955, a bridge 961, internal buses 957 and 959, an interface 963, an input device 965, an output device 967, a storage device 969, a drive 971, a connection port 973, and a communication device 975.

The CPU 951 functions as an arithmetic processing device and a control device, controls an overall operation of the information processing device 30 according to various programs stored in the ROM 953 or the like. The ROM 953 stores programs and arithmetic operation parameters used by the CPU 951, and the RAM 955 temporarily stores a program to be used in an execution of the CPU 951, parameters that appropriately change in execution thereof, and the like. For example, the CPU 951 may execute the function of the control unit 38.

The CPU 951, the ROM 953, and the RAM 955 are connected to one another using the bridge 961, the internal buses 957, 959, and the like. In addition, the CPU 951, the ROM 953, and the RAM 955 are also connected to the input device 965, the output device 967, the storage device 969, the drive 971, the connection port 973, and the communication device 975 via the interface 963.

The input device 965 includes input devices such as a touch panel, a keyboard, a mouse, a button, a microphone, a switch, a lever to which information is input. The input device 965 also includes an input control circuit for generating an input signal on the basis of the input information and outputting the input signal to the CPU 951.

The output device 967 includes a display device such as a cathode ray tube (CRT) display device, a liquid crystal display device, an organic electro luminescence (organic EL) display device, or the like. Furthermore, the output device 967 may include a sound output device such as a speaker and a headphone.

The storage device 969 is a store device for storing data of the information processing device 30. The storage device 969 may include a storage medium, a storage device for storing data in the storage medium, a reading device for reading data from the storage medium, and a deletion device for deleting stored data. The storage device 969 may execute the function of the storage unit 36.

The drive 971 is a read/writer for a store medium, which is incorporated in the information processing device 30 or externally attached thereto. For example, the drive 971 can read information stored in an attached removable store medium such as a magnetic disk, an optical disk, a magneto-optical disk, or a semiconductor memory, and output it to the RAM 353. Moreover, the drive 971 can also write information to a removable storage medium.

The connection port 973 is a connection interface constituted by a connection port for connecting an external connection device such as a universal serial bus (USB) port, an Ethernet (registered trademark) port, an IEEE802.11 standard port, and an optical audio terminal.

The communication device 975 is a communication interface constituted by a communication device and the like for a connection to the communication network 40. In addition, the communication device 975 may be a wired or wireless LAN compliant communication device or a cable communication device that performs wired cable communication. The communication device 975 may execute the function of the communication unit 31.

In addition, a computer program for causing hardware such as the CPU, the ROM, and the RAM built in the information processing device 30 to exhibit the same functions as respective constituents of the information processing device according to the present embodiment described above can be created. In addition, a storage medium for storing the computer program is also provided.

3-3. Operation of Information Processing Device

Next, an example of the state determination processing of livestock executed by the control unit 38 of the information processing device 30 will be described with reference to FIG. 32.

First, the vibration generated power integrating unit 32 obtains the activity amount of livestock at every unit time set in advance. In the example of the present embodiment, the vibration generated power integrating unit 32 obtains the voltage integrated value ∫V correlating with the activity amount of livestock (S12). For example, the vibration generated power integrating unit 32 may integrate values of the inter-terminal voltage V of the vibration power accumulation unit 114 included in signals transmitted in the daytime time zone in which signals can be timely transmitted from the signal transmission device 10A attached to livestock. Next, the temperature difference calculation unit 33 obtains the metabolic information of livestock. In the example of the present embodiment, the temperature difference calculation unit 33 obtains the temperature difference ΔT between a first temperature T1 and a second temperature T2 included in each signal as a value correlated with the metabolic rate of livestock (S14). For example, the temperature difference calculation unit 33 may set an average value of the absolute values of differences between a first temperature T1 and a second temperature T2 per day as the temperature difference ΔT.

Next, the state determination unit 34 determines whether or not the voltage integrated value ∫V is zero (S16). In a case in which the voltage integrated value ∫V is zero (Yes in S16), the state determination unit 34 determines whether or not the temperature difference ΔT is zero (S18). A value used for comparison with the temperature difference ΔT may be a value obtained by adding a predetermined error range to zero. In a case in which the temperature difference ΔT is zero (Yes in S18), the state determination unit 34 determines whether or not a time differentiated value dΔT/dt of the temperature difference ΔT is less than a predetermined threshold value Δ on the basis of a history of a change in the accumulated temperature difference ΔT (S20). For example, in a case in which an average value of the temperature difference per day is assumed to be the temperature difference ΔT, an amount of change in the temperature difference ΔT per day is compared with the threshold value Δ from three to four days before the temperature difference ΔT becomes zero. The threshold value Δ can be set to an appropriate value as a threshold value for determining whether the temperature difference ΔT becomes zero as a result of gradual decrease or suddenly becomes zero.

In a case in which a time differentiated value dΔT/dt of the temperature difference ΔT is less than the threshold value Δ (Yes in S20), the temperature difference ΔT becomes zero as a result of the metabolism of livestock gradually decreasing, and thus the state determination unit 34 determines that the livestock has died (S40). Note that, although an example in which the death of livestock is determined in step S40 in a case in which it is determined whether or not a change in the temperature difference ΔT is zero in step S18 and a change in the temperature difference ΔT is zero is shown, the state determination unit 34 may further determine a hyposthenia state which is a preliminary stage of death. In a case of determining hyposthenia, a threshold value X for hyposthenia determination is provided in addition to determining whether or not the temperature difference ΔT is zero, the state determination unit 34 may determine that the state of livestock is in the hyposthenia state in a case in which the temperature difference ΔT is equal to or greater than zero and equal to or less than the threshold value X for hyposthenia determination. On the other hand, in a case in which the time differentiated value dΔT/dt of the temperature difference ΔT is equal to or greater than the threshold value Δ (No in S20), since the temperature difference ΔT becomes relatively abruptly zero, the state determination unit 34 determines that the signal transmission device 10A has fallen out of livestock (S38).

In step S16 described above, in a case in which the voltage integrated value ∫V is not zero (No in S16), the state determination unit 34 determines whether or not the voltage integrated value ∫V is less than a threshold value α (S22). The threshold value α can be set to an appropriate value as a threshold value for determining that the activity amount of livestock is reduced as compared with the normal level. In a case in which the voltage integrated value ∫V is less than the threshold value α (Yes in S22), the state determination unit 34 determines whether or not the temperature difference ΔT is stable on the basis of the history of a change in the accumulated temperature difference ΔT, for example, the time differentiated value of ΔT (S24).

In a case in which the temperature difference ΔT is not zero and is stable (Yes in S24), since the metabolism of livestock is normal but the activity amount is small, the state determination unit 34 determines that the livestock is injured (S44). On the other hand, in a case in which the temperature difference ΔT is not stable (No in S24), the state determination unit 34 determines whether or not the temperature difference ΔT tends to increase on the basis of the history of a change in the accumulated temperature difference ΔT (S26). In a case in which the temperature difference ΔT tends to increase (Yes in S26), since the livestock generates heat and the activity amount decreases, the state determination unit 34 determines that the livestock is sick (S46). Note that "determining that livestock is sick" includes not only concluding that livestock is sick, but also estimating that there is a possibility that livestock is sick or there is a high possibility that livestock is sick.

In step S22 described above, the voltage integrated value ∫V is equal to or greater than the threshold value α (No in S22), the state determination unit 34 determines whether or not the voltage integrated value ∫V exceeds a threshold value β (S28). The threshold value β can be set to an appropriate value as a threshold value for determining that the activity amount of livestock largely increases as compared to the normal level. In a case in which the voltage integrated value ∫V exceeds the threshold value β (Yes in S28), the state determination unit 34 determines whether or not the temperature difference ΔT tends to increase on the basis of the history of a change in the accumulated temperature difference ΔT (S30). In a case in which the temperature difference ΔT tends to increase (Yes in S30), the state determination unit 34 determines that the livestock is in an esthetic state (S48).

In step S28 described above, in a case in which the voltage integrated value ∫V is equal to or less than the threshold value β (No in S28), the state determination unit 34 determines whether or not the voltage integrated value ∫V exceeds a threshold value γ (S32). The threshold value γ can be set to an appropriate value as the threshold value γ for determining that the activity amount of livestock is not largely increased as compared with the normal level, but is somewhat increased. In a case in which the voltage integrated value ∫V exceeds the threshold values γ (Yes in S32), the state determination unit 34 determines whether or not the temperature difference ΔT tends to decrease on the basis of the history of a change in the accumulated temperature difference ΔT (S34). In a case in which the temperature difference ΔT tends to decrease (Yes in S34), the state determination unit 34 determines that the live stock is in the childbirth state (S50).

In a case in which the temperature difference ΔT is not zero (No in S18) in step S18, in a case in which the temperature difference ΔT does not tend to increase (No in S26) in step S26, in a case in which the temperature difference ΔT does not tend to increase (No in S30) in step S30, and in a case in which the voltage integrated value ∫V is equal to or less than the threshold value γ (No in S32) in step S32, the state determination unit 34 determines that there is no abnormality in the livestock (S42).

Figure 32:
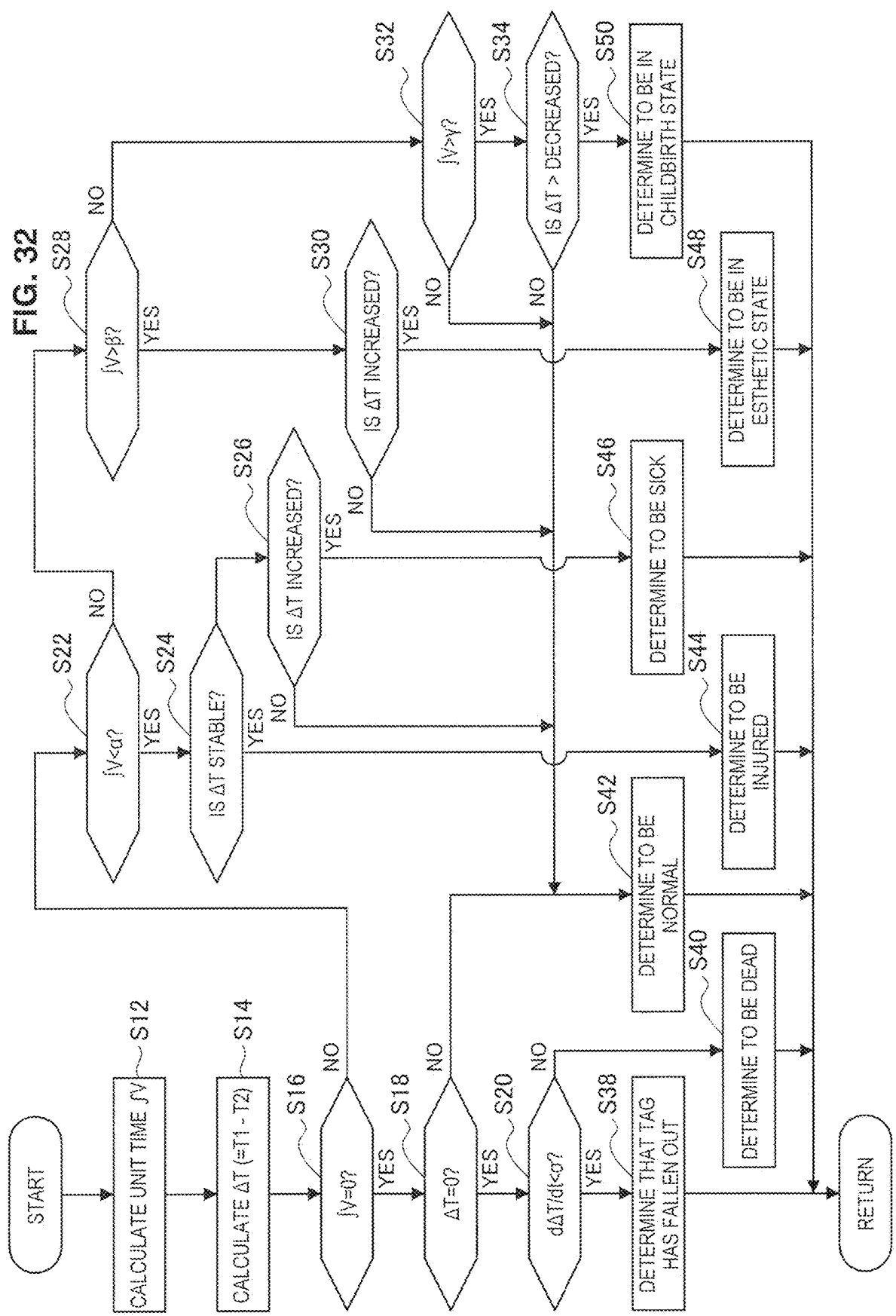
FIG. 32 is a flowchart which shows an example of state determination processing executed by the information processing device of the management system according to the embodiment.

Note that, after the state of livestock such as normal, injury, tag fall out, an estrus state, or a childbirth state, is determined by the state determination processing of FIG. 32, the control unit 38 outputs a result of the determination as state information. For example, the control unit 38 performs processing of recording state information "injury" in a database in the storage unit 36 in association with the identification information of the signal transmission device 10A which has transmitted information used in the state determination processing in a case in which a result of the determination is "injury.". Moreover, the control unit 38 may perform processing of transmitting notification information including the identification information of the signal transmission device 10A or the identification information and state information of livestock to the information terminal 60 or 70 using the transmission control unit 37 and the communication unit 31 in a case in which a determination result of the state determination processing is in a predetermined state as output processing.

As above, an example of the state determination processing has been described, and the information processing device 30 can determine the biological information of livestock on the basis of the information of a first temperature T1, the information of a second temperature T2, and the vibration information included in a signal transmitted from the signal transmission device 10A attached to each head of livestock. Therefore, the rancher 3A or the veterinarian 3B accesses the information processing device 30 via the information terminals 60 and 70, thereby ascertaining the state of individual livestock. As a result, diagnosis, treatment, or the like of livestock can be timely performed when necessary.

Moreover, the information processing device 30 can detect fall out of the signal transmission device 10A on the basis of the information of a first temperature T1, the information of a second temperature T2, and the vibration information included in a signal transmitted from the signal transmission device 10A attached to each head of livestock. In this case, since the transmission of a signal from the signal transmission device 10A can be continued even in a falling out state, the existence range of the signal transmission device 10 falling out can be narrowed on the basis of the identification information of the signal relay device 10B or the master relay device 10C, and the signal transmission device 10A is easy to be found.

Not that the state determination processing show in FIG. 32 is merely an example, and the information processing device 30 may perform another appropriate state determination processing. For example, in a case in which the signal transmission device 10A includes a sensor other than the temperature sensor and the vibration sensor 335, the information processing device 30 may execute desirable state determination processing using information of a measurement value detected by the sensor. In addition, the information processing device 30 may determine the state of livestock using a learning algorithm such as artificial intelligent (AI) processing or machine learning, for example, with the vibration information and temperature information as an input and the biological information serving as the state information of livestock as an output.

4. OTHER APPLICATION EXAMPLES OF MANAGEMENT SYSTEM

Figure 33:
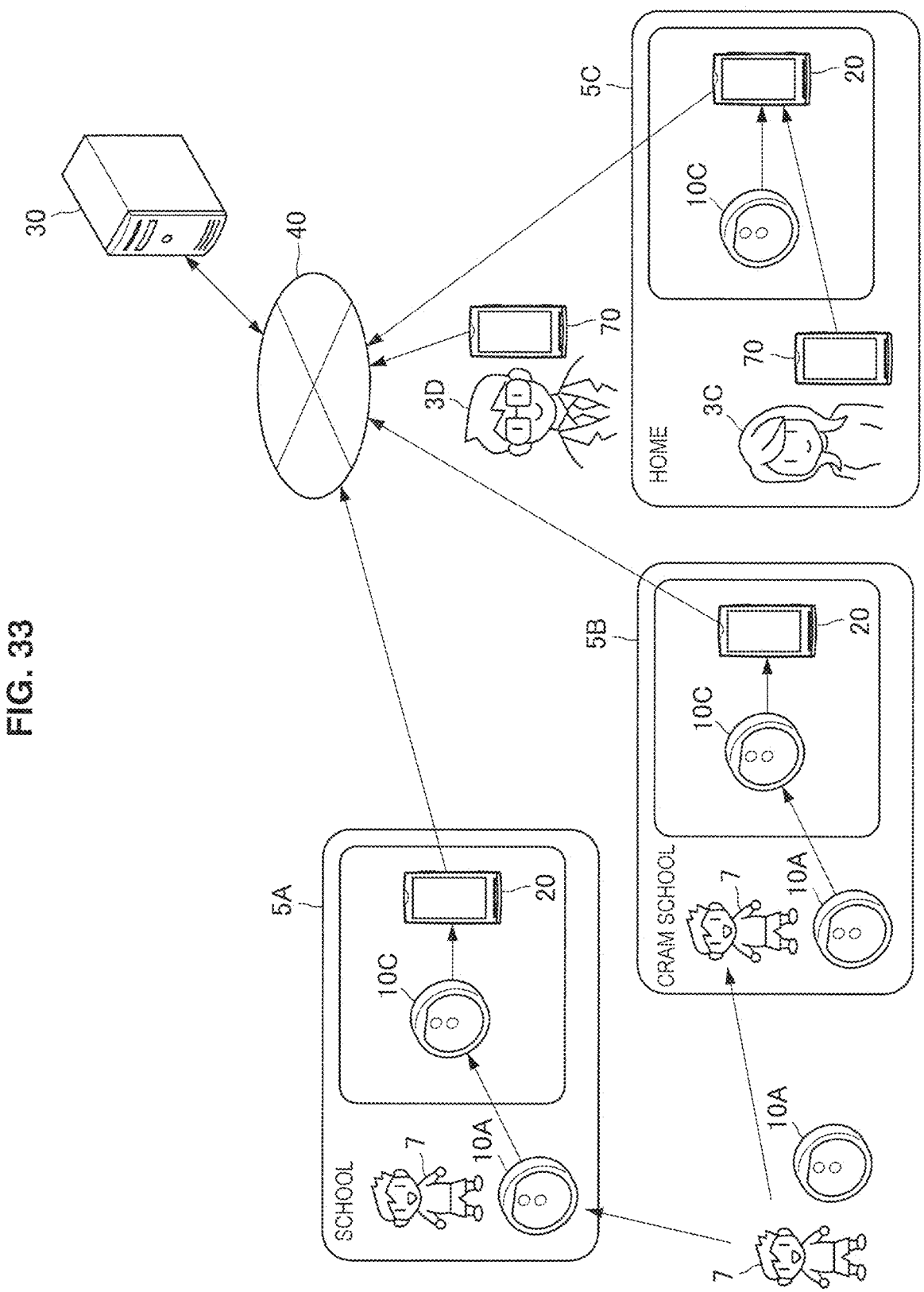
FIG. 33 is an explanatory diagram which describes another application example of the management system according to the embodiment.

Examples in which the signal transmission device 10 and the management system 1 according to the present embodiment are applied to a management system for mainly managing livestock such as cattle have been described. Hereinafter, another application example of the management system 1 according to the present embodiment will be described with reference to FIG. 33. FIG. 33 is an explanatory diagram which shows another application example of the management system 1 according to the present embodiment.

Another application example of the management system 1 according to the present embodiment is a system in which a guardian 3C ascertains position, temperature information, or vibration information of a watching target person 7 such as a child, thereby confirming the safety of the watching target person 7.

Specifically, in a mode shown in FIG. 33, the signal transmission device 10A is attached to the watching target person 7, and the master relay device 10C is installed at each facility such as a school 5A, a cram school 5B, and home 5C. In a case in which the watching target person 7 to whom the signal transmission device 10A is attached enters one of the facilities such as the school 5A, the cram school 5B, and the home 5C, since the signal transmission device 10A is within a communication range of the master relay device 10C, a signal is transmitted from the signal transmission device 10A to the master relay device 10C. The master relay device 10C which has received a signal from the signal transmission device 10A transmits the received signal to the information processing device 30 via the communication network 40 using the network connection device 20.

The information processing device 30 can determine which master relay device 10C has received a signal from the signal transmission device 10A, thereby determining which indoor place of the school 5A, the cram school 5B, or the home 5C the watching target person 7 to which the signal transmission device 10A is attached has entered. At this time, the signal from the signal transmission device 10A includes information of a first temperature T1, information of a second temperature T2, and vibration information, and thereby the information processing device 30 can determine the safety of the body of the watching target person 7. In addition, the information processing device 30, in a case in which the signal from a signal transmission device 10A is not received at a predetermine time by the master relay device 10C, it can be determined that the watching target person 7 to which the signal transmission device 10A is attached exits from the facility in which the master relay device 10C is installed.

Therefore, the guardians 3C and 3D of the watching target person 7 are connected to the information processing device 30 using an information terminal 80 such as a smart phone or a tablet terminal, thereby confirming the safety of the body together with whether or not the watching target person 7 has entered or has exited from any of the facilities, and which of the facilities the watching target person 7 has entered or has exited. As a result, the guardians 3C and 3D confirm a location of the watching target person 7, thereby confirming the safety of the watching target person 7.

Note that, in another application example of the management system 1, a place in which the master relay device 10C is installed is not limited to a school, a cram school, and home, and may be a house of friend or public facilities such as parks and police boxes, and major intersections, and the like. It is easier to ascertain the location or the state of the body of the watching target person 7 as the number of installation places of the master relay device 10C increases.

5. SUMMARY

As described above, in the management system 1 according to the present embodiment, the signal transmission device 10A transmits a signal using power generated by the first optical power generation unit 311, the second optical power generation unit 323, and the vibration sensor 335. Therefore, since the signal transmission device 10A does not need to have a power source such as a battery mounted thereon, the burden on an attachment target can be reduced and portability can be improved.

In the signal transmission device 10 according to the present embodiment, the light receiving units 312 and 324 of the first optical power generation unit 311 and the second optical power generation unit 323 are provided on the first surface S1 and the second surface S2 facing outward in opposite directions, respectively. Therefore, even in a case in which the signal transmission device 10 is attached to an attachment target such that one of the first surface S1 and the second surface S2 is in contact with the attachment target, a signal can be transmitted without interruption of power generation. Likewise, even in a case in which the signal transmission device 10 falls out of an attachment target, power generation is continued by the first optical power generation unit 311 or the second optical power generation unit 323, and a signal can be transmitted. Therefore, the existence range of the signal transmission device 10 can be narrowed on the basis of the identification information of the signal relay device 10B or the master relay device 10C included in a signal received by the information processing device 30, and the signal transmission device 10 is easy to be found.

Moreover, in the signal transmission device 10 according to the present embodiment, the first temperature sensor 351 and the second temperature sensor 353 each having thermal contacts are provided on the first surface S1 and the second surface S2. Therefore, for example, in a case in which the signal transmission device 10 is attached to livestock such as cattle, it is possible to ascertain the metabolic rate of the livestock on the basis of the temperature difference ΔT between a first temperature T1 detected by the first temperature sensor 351 and a second temperature T2 detected by the second temperature sensor 353. Furthermore, the signal transmission device 10 according to the present embodiment includes the vibration sensor 335. Therefore, it is possible to ascertain the activity information of an object to which the signal transmission device 10 is attached on the basis of the detected vibration information. For this reason, the information processing device 30 can ascertain the biological information on the basis of the metabolic information and activity information of an attachment target.

In addition, the signal transmission device 10 according to the present embodiment ascertains in which communication available range of the signal relay device 10B and the master relay device 10C the signal transmission device 10A which has transmitted a signal exists, thereby ascertaining the position of an attachment target to which the signal transmission device 10A is attached.

Furthermore, in the cover case 200 for attaching the signal transmission device 10 according to the present embodiment to an ear mark, the band portion 230 is strongly engaged with the connection portion 240, and this engagement is not easily released even by vibration, hooking, or the like. Therefore, falling out of the signal transmission device 10 can be prevented. In addition, the cover case 200 has the protruding portion 222 for causing the posture to be stabilized at the time of being attached to an ear mark. Therefore, the detection accuracy of vibration is guaranteed, the detection accuracy of temperature on the body surface side of livestock is guaranteed, and it is possible to accurately ascertain the biological information of livestock.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, in the management system 1 according to the present embodiment, the temperature difference ΔT is obtained after the information processing device 30 has received the information of a first temperature T1 and the information of a second temperature T2, but the technology of the present disclosure is not limited to this example. For example, when the signal transmission device 10A transmits a signal, the signal transmission device 10A may add the information of the temperature difference ΔT to the signal in advance and transmit it. Likewise, in the management system 1 according to the embodiment described above, the integration of vibration generated power, calculation of temperature difference, and state determination processing are executed by the information processing device 30, but some or all of these types of arithmetic operation processing may be executed by the signal transmission device 10A, the signal relay device 10B, or the master relay device 10C. In this case, the information processing device 30 may receive a signal including an arithmetic operation result.

In addition, in the management system 1 according to the present embodiment, a flowchart of state determination processing executed by the information processing device 30 is merely an example, and various modifications can be made. For example, each step may be replaced before and after.

Figure 34:
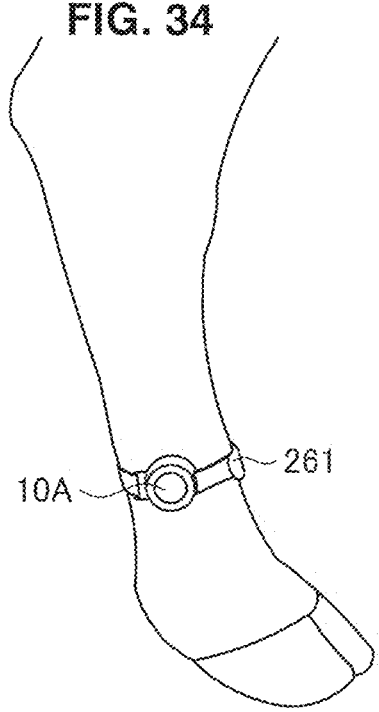
FIG. 34 is an explanatory diagram which shows how the signal transmission device is attached to a leg of livestock.
Figure 35:
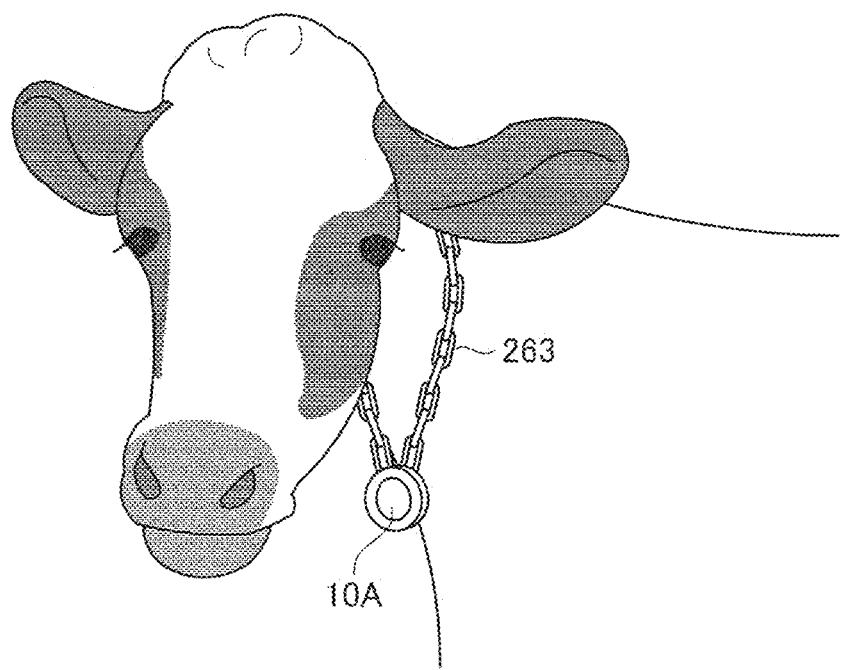
FIG. 35 is an explanatory diagram which shows how the signal transmission device is attached to a neck of livestock.

In addition, although the signal transmission device 10 according to the present embodiment is attached to an ear mark, the technology of the present disclosure is not limited to this example. For example, the signal transmission device 10A may be attached to the leg of livestock such as cattle using a fixing belt 261 as shown in FIG. 34, and may be attached to the neck using a chain 263 as shown in FIG. 35. In addition, the signal transmission device 10A may be attached to a tag.

In addition, a held instrument to be held in the cover case 200 is the signal transmission device 10 including a vibration sensor which detects vibration in a predetermined reference direction in the embodiment described above, but the technology of the present disclosure is not limited to the example. By using the cover case 200 according to the present disclosure even in instruments other than the signal transmission device 10, the instruments are also held in a predetermined posture commensurate with the reference direction, and the possibility of an instrument falling out can be reduced.

Moreover, in the present embodiment, as an object to be managed to which the signal transmission device 10A is attached, living being such as livestock or people is taken as an example, but an object to be managed is not limited to this example. For example, as an object to be managed, it is possible to exemplify a mobile machine in which the movement of unmanned vehicles, drones, and the like is automatically controlled in addition to a pet livestock such as pet, and a person to be watched over such as an infant and an elderly people. According to the management system 1 according to the present disclosure, it is possible to manage an object to be managed in a plurality of predetermined management states by causing the signal transmission device 10A to be attached to these objects to be managed.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A management system including: a signal transmission device including a housing that is attached to an object to be managed in a predetermined direction, a first optical power generation unit that includes a light receiving unit on a first surface facing outward in one direction along the predetermined direction, a second optical power generation unit that includes a light receiving unit on a second surface facing outward in another direction along the predetermined direction, a first temperature sensor that has a thermal contact on the first surface, a second temperature sensor that has a thermal contact on the second surface, a communication control unit that transmits a signal including temperature information detected by the first temperature sensor and the second temperature sensor using power generated by at least one of the first optical power generation unit and the second optical power generation unit; and an information processing device including a control unit configured to receive a signal transmitted from the signal transmission device and output the state information of the object to be managed to which the signal transmission device is attached, on a basis of the temperature information detected by at least the first temperature sensor and the second temperature sensor.

(2) The management system according to (1), in which at least one of the first temperature sensor and the second temperature sensor includes a resistance temperature detector disposed on a rear surface side of the light receiving unit of the first optical power generation unit or the light receiving unit of the second optical power generation unit, and a heat conductor that transmits heat from the thermal contact to the resistance temperature detector.

(3) The management system according to (1) or (2), in which the signal transmission device is a device attached to a living body, the predetermined direction is a direction facing a body surface of the living body, and the control unit of the information processing device outputs the state information of the living body to which the signal transmission device is attached, using metabolic information of the living body based on a temperature difference between a first temperature on the first surface side detected by the first temperature sensor and a second temperature on the second surface side detected by the second temperature sensor.

(4) The management system according to one of (1) to (3), in which the information processing device further includes a transmission control unit that transmits notification information for controlling notification in an information terminal.

(5) The management system according to one of (1) to (4), in which the signal transmission device further includes a vibration sensor that detects vibration in the predetermined direction.

(6) The management system according to (5), in which the vibration sensor includes a power generation element that generates power using vibration, and the communication control unit further transmits the signal using the power generated by the power generation element.

(7) The management system according to (5) or (6), in which the vibration sensor includes a plate-shaped piezoelectric element and a weight fixed to one end side of the piezoelectric element, and the vibration sensor is fixed to base material on the other end side of the piezoelectric element.

(8) The management system according to one of (5) to (7), in which the vibration sensor is disposed between the first optical power generation unit and the second optical power generation unit.

(9) The management system according to one of (5) to (8), in which the signal transmission device is a device attached to a moveable object to be managed, and the control unit of the information processing device outputs the state information of the object to be managed to which the signal transmission device is attached, using activity information of the object to be managed based on vibration information detected by the vibration sensor.

(10) The management system according to one of (5) to (9), in which the signal transmission device is a device attached to livestock, and the control unit of the information processing device outputs biological information of the livestock to which the signal transmission device is attached, using activity information of the livestock based on vibration information detected by the vibration sensor and metabolic information of the livestock based on a temperature difference between a first temperature on the first surface side detected by the first temperature sensor and a second temperature on the second surface side detected by the second temperature sensor.

(11) The management system according to (10), in which biological information of the livestock is information of at least one of an estrus state, a childbirth state, a death or hyposthenia state, and an injury or disease state.

(12) The management system according to one of (5) to (11), in which the object to be managed is livestock, and the control unit of the information processing device outputs information indicating that the signal transmission device has fallen out of the livestock, using activity information based on vibration information detected by the vibration sensor and metabolic information based on a temperature difference between a first temperature on the first surface side detected by the first temperature sensor and a second temperature on the second surface side detected by the second temperature sensor.

(13) The management system according to one of (5) to (12), in which the control unit of the information processing device outputs the state information of the object to be managed to which the signal transmission device is attached, using vibration information detected by the vibration sensor at a predetermined unit time set in advance.

(14) The management system according to one of (1) to (13), in which the signal transmission device includes a non-contact communication antenna for performing non-contact communication and a first antenna used in wireless communication by the communication control unit.

(15) The management system according to (14), in which the non-contact communication antenna is an antenna formed on a substrate, and the non-contact communication antenna is provided on a rear surface side of the light receiving unit of the first optical power generation unit.

(16) The management system according to one of (1) to (15), in which the signal transmission device is attached to the object to be managed via a cover case, and the cover case includes a case main body portion that accommodates the signal transmission device such that the signal transmission device faces the predetermine direction, a band portion that has an engaging portion on one surface and is wound around an attachment target portion, a connection portion into which the band portion is inserted, the connection portion having a locking portion configured to be locked at the engaging portion, and a guide portion that holds the band portion inserted into the connection portion in a predetermined posture.

(17) A signal transmission device including: a housing that is attached to an object to be managed in a predetermined direction; a first optical power generation unit that includes a light receiving unit on a first surface facing outward in one direction along the predetermined direction; a second optical power generation unit that includes a light receiving unit on a second surface facing outward in another direction along the predetermined direction; a first temperature sensor that has a thermal contact on the first surface; a second temperature sensor that has a thermal contact on the second surface; a communication control unit that transmits a signal including temperature information detected by the first temperature sensor and the second temperature sensor using power generated by at least one of the first optical power generation unit and the second optical power generation unit.

(18) The signal transmission device according to (17), in which at least one of the first temperature sensor and the second temperature sensor includes a resistance temperature detector disposed on a rear surface side of the light receiving unit of the first optical power generation unit or the light receiving unit of the second optical power generation unit, and a heat conductor that transmits heat from the thermal contact to the resistance temperature detector.

(19) The signal transmission device according to (17) or (18), in which the signal transmission device is a device attached to a living body, the predetermined direction is a direction facing a body surface of the living body, and information of a first temperature on the first surface side detected by the first temperature sensor and information of a second temperature on the second surface side detected by the second temperature sensor are used to obtain metabolic information of the living body to which the signal transmission device is attached.

(20) The signal transmission device according to one of (17) to (19), further including a vibration sensor that detects vibration in the predetermined direction.

(21) The signal transmission device according to (20), in which the vibration sensor includes a power generation element that generates power using vibration, and the communication control unit further transmits the signal using the power generated by the power generation element.

(22) The signal transmission device according to (20) or (21), in which the vibration sensor includes a plate-shaped piezoelectric element, and a weight fixed to one end side of the piezoelectric element, and the vibration sensor is fixed to base material on the other end side of the piezoelectric element.

(23) The signal transmission device according to one of (20) to (22), in which the vibration sensor is disposed between the first optical power generation unit and the second optical power generation unit.

(24) The signal transmission device according to one of (20) to (23), in which the signal transmission device is a device attached to a moveable object to be managed, and vibration information detected by the vibration sensor is used to obtain activity information of the object to be managed to which the signal transmission device is attached.

(25) The signal transmission device according to one of (20) to (24), in which the signal transmission device is a device attached to livestock, vibration information detected by the vibration sensor is used to obtain activity information of the livestock, information of a first temperature on the first surface side detected by the first temperature sensor and information of a second temperature on the second surface side detected by the second temperature sensor are used to obtain metabolic information of the livestock, and the activity information and the metabolic information of the livestock are used to obtain biological information of the livestock to which the signal transmission device is attached.

(26) The signal transmission device according to (25), in which biological information of the livestock is information of at least one of an estrus state, a childbirth state, a death or hyposthenia state, and an injury or disease state.

(27) The signal transmission device according to one of (20) to (26), in which the object to be managed is livestock, and vibration information detected by the vibration sensor is used to obtain activity information of the livestock, information of a first temperature on the first surface side detected by the first temperature sensor and information of a second temperature on the second surface side detected by the second temperature sensor are used to obtain metabolic information of the livestock, and the activity information and the metabolic information of the livestock are used to detect that the signal transmission device has fallen out of the livestock.

(28) The signal transmission device according to one of (20) to (27), in which a piece of vibration information detected at a predetermined unit time set in advance among pieces of the vibration information detected by the vibration sensor is used to obtain state information of the object to be managed to which the signal transmission device is attached.

(29) The signal transmission device according to one of (17) to (28), in which the signal transmission device includes a non-contact communication antenna for performing non-contact communication and a first antenna used in wireless communication by the communication control unit.

(30) The signal transmission device according to one of (17) to (29), in which the non-contact communication antenna is an antenna formed on a substrate, and the non-contact communication antenna is provided on a rear surface side of the light receiving unit of the first optical power generation unit.

(31) The signal transmission device according to one of (17) to (30), in which the signal transmission device is attached to the object to be managed via a cover case, and the cover case includes a case main body portion that accommodates the signal transmission device such that the signal transmission device faces the predetermine direction, a band portion that has an engaging portion on one surface and is wound around an attachment target portion, a connection portion into which the band portion is inserted, the connection portion having a locking portion configured to be locked at the engaging portion, and a guide portion that holds the band portion inserted into the connection portion in a predetermined posture.

(32) A cover case includes a case main body portion that accommodates a held instrument having a predetermined reference direction, a band portion that has an engaging portion on one surface and is wound around an attachment target portion, a connection portion that has a locking portion locked at the engaging portion, and into which the band portion is inserted, and a guide portion that holds the band portion inserted into the connection portion in a predetermined posture, in which a disposition direction of the band portion wound around the attachment target portion is substantially orthogonal to the reference direction.

(33) The cover case according to (32) includes a first guide surface and a second guide surface that face the front and rear surfaces of the band portion, respectively, and extend in an extending direction of the connection portion.

(34) The cover case according to (33) in which the second guide surface has a first surface portion and a second surface portion opposed to both end sides in a width direction of the one surface of the band portion, and the locking portion is provided between the first surface portion and the second surface portion.

(35) The cover case according to (34) in which the locking portion has an inclined portion inclined in an insertion direction of the band portion.

(36) The cover case according to any one of (32) to (35) in which the engaging portion is a step portion extending in a direction intersecting a longitudinal direction of the band portion, and the locking portion is a claw portion locked at the step portion.

(37) The cover case according to one of (32) to (36) in which the engaging portion is an edge of groove or slit provided in the band portion.

(38) The cover case according to one of (33) to (37) in which the locking portion protrudes further inward of the connection portion than the first guide surface or the second guide surface.

(39) The cover case according to one of (33) to (38) in which only a tip end portion of the locking portion is in contact with the band portion when the locking portion and the engaging portion are in a locking state.

(40) The cover case according to one of (32) to (39) in which the case main body portion has a protruding portion that is provided in an extending direction of the band portion wound around the attachment target portion and has a line contact or surface contact in a predetermined length range.

(41) The cover case according to (40) in which the height of the protruding portion is equal to the height of the case main body portion.

(42) The cover case according to (32) to (41) in which the cover case holds the held instrument including a vibration sensor for detecting vibration in the reference direction.

(43) The cover case according to (42) in which the cover case protrudes radially outward from the case main body portion, has an overhanging portion in which the band portion and the connection portion are provided, and is positioned on a side opposite to a position at which the overhanging portion is provided.

(44) The cover case according to (42) or (43) in which the vibration sensor of the held instrument is used to obtain activity information of an attachment target of the cover case on the basis of vibration information detected by the vibration sensor.

(45) The cover case according to one of (32) to (44) in which the held instrument includes a plurality of optical power generation units having light receiving unit on surfaces of both sides in a predetermined direction, and the case main body portion has openings corresponding to the surfaces of both sides.

(46) The cover case according to (45) in which the held instrument transmits a signal including sensor information detected by a sensor of the held instrument using power generated by at least one of the plurality of optical power generation units, and the sensor information is used to obtain state information of an attachment target of the cover case.

(47) The cover case according to one of (32) to (46) in which the held instrument includes a temperature sensor having thermal contacts respectively on the surfaces of both sides in a predetermined direction, and the case main body portion has openings corresponding to the surfaces of both sides.

(48) The cover case according to (47) in which the temperature sensor of the held instrument is used to obtain metabolic information of a living body to which the cover case is attached on the basis of temperature information detected by the temperature sensor.

(49) The cover case according to one of (32) to (48) in which the cover case is attached to livestock or people.

(50) The cover case according to one of (32) to (49) in which the cover case is attached to an ear mark of livestock.

REFERENCE SIGNS LIST 1 management system
10 signal transmission device
10A signal transmission device (tag)
10B signal relay device
10C master relay device
30 information processing device
311 first optical power generation unit
312 light receiving unit
315 non-contact communication antenna
323 second optical power generation unit
324 light receiving unit
328 first antenna
329 second antenna
331 circuit board
335 vibration sensor
341 first heat conductor
342 first resistance temperature detector
343 second heat conductor
344 second resistance temperature detector
351 first temperature sensor
353 second temperature sensor

The invention claimed is:

1. A management system comprising:
 a signal transmission device including
  a housing that is attached to an object to be managed in a predetermined direction,
  a first optical power generation unit that includes a light receiving unit on a first surface facing outward in one direction along the predetermined direction,
  a second optical power generation unit that includes a light receiving unit on a second surface facing outward in another direction along the predetermined direction,
  a first temperature sensor that has a thermal contact on the first surface,
  a second temperature sensor that has a thermal contact on the second surface,
  a communication control unit that transmits a signal including temperature information detected by the first temperature sensor and the second temperature sensor using power generated by at least one of the first optical power generation unit and the second optical power generation unit; and an information processing device including a control unit configured to receive a signal transmitted from the signal transmission device and output the state information of the object to be managed to which the signal transmission device is attached, on a basis of the temperature information detected by at least the first temperature sensor and the second temperature sensor.

2. The management system according to claim 1, wherein at least one of the first temperature sensor and the second temperature sensor includes a resistance temperature detector disposed on a rear surface side of the light receiving unit of the first optical power generation unit or the light receiving unit of the second optical power generation unit, and a heat conductor that transmits heat from the thermal contact to the resistance temperature detector.

3. The management system according to claim 1, wherein the signal transmission device is a device attached to a living body, the predetermined direction is a direction facing a body surface of the living body, and the control unit of the information processing device outputs the state information of the living body to which the signal transmission device is attached, using metabolic information of the living body based on a temperature difference between a first temperature on the first surface side detected by the first temperature sensor and a second temperature on the second surface side detected by the second temperature sensor.

4. The management system according to claim 1, wherein the information processing device further includes a transmission control unit that transmits notification information for controlling notification in an information terminal.

5. The management system according to claim 1, wherein the signal transmission device further includes a vibration sensor that detects vibration in the predetermined direction.

6. The management system according to claim 5, wherein the vibration sensor includes a power generation element that generates power using vibration, and the communication control unit further transmits the signal using the power generated by the power generation element.

7. The management system according to claim 5, wherein the vibration sensor includes a plate-shaped piezoelectric element and a weight fixed to one end side of the piezoelectric element, and the vibration sensor is fixed to base material on the other end side of the piezoelectric element.

8. The management system according to claim 5, wherein the vibration sensor is disposed between the first optical power generation unit and the second optical power generation unit.

9. The management system according to claim 5, wherein the signal transmission device is a device attached to a moveable object to be managed, and the control unit of the information processing device outputs the state information of the object to be managed to which the signal transmission device is attached, using activity information of the object to be managed based on vibration information detected by the vibration sensor.

10. The management system according to claim 5, wherein the signal transmission device is a device attached to livestock, and the control unit of the information processing device outputs biological information of the livestock to which the signal transmission device is attached, using activity information of the livestock based on vibration information detected by the vibration sensor and metabolic information of the livestock based on a temperature difference between a first temperature on the first surface side detected by the first temperature sensor and a second temperature on the second surface side detected by the second temperature sensor.

11. The management system according to claim 10, wherein biological information of the livestock is information of at least one of an estrus state, a childbirth state, a death or hyposthenia state, and an injury or disease state.

12. The management system according to claim 5, wherein the object to be managed is livestock, and the control unit of the information processing device outputs information indicating that the signal transmission device has fallen out of the livestock, using activity information based on vibration information detected by the vibration sensor and metabolic information based on a temperature difference between a first temperature on the first surface side detected by the first temperature sensor and a second temperature on the second surface side detected by the second temperature sensor.

13. The management system according to claim 5, wherein the control unit of the information processing device outputs the state information of the object to be managed to which the signal transmission device is attached, using vibration information detected by the vibration sensor at a predetermined unit time set in advance.

14. The management system according to claim 1, wherein the signal transmission device includes a non-contact communication antenna for performing non-contact communication and a first antenna used in wireless communication by the communication control unit.

15. The management system according to claim 14, wherein the non-contact communication antenna is an antenna formed on a substrate, and the non-contact communication antenna is provided on a rear surface side of the light receiving unit of the first optical power generation unit.

16. The management system according to claim 1, wherein the signal transmission device is attached to the object to be managed via a cover case, and the cover case includes
a case main body portion that accommodates the signal transmission device such that the signal transmission device faces the predetermine direction,
a band portion that has an engaging portion on one surface and is wound around an attachment target portion,
a connection portion into which the band portion is inserted, the connection portion having a locking portion configured to be locked at the engaging portion, and
a guide portion that holds the band portion inserted into the connection portion in a predetermined posture.

17. A signal transmission device comprising:
a housing that is attached to an object to be managed in a predetermined direction;

a first optical power generation unit that includes a light receiving unit on a first surface facing outward in one direction along the predetermined direction;

a second optical power generation unit that includes a light receiving unit on a second surface facing outward in another direction along the predetermined direction;

a first temperature sensor that has a thermal contact on the first surface;

a second temperature sensor that has a thermal contact on the second surface;

a communication control unit that transmits a signal including temperature information detected by the first temperature sensor and the second temperature sensor using power generated by at least one of the first optical power generation unit and the second optical power generation unit.

18. The signal transmission device according to claim 17, wherein at least one of the first temperature sensor and the second temperature sensor includes a resistance temperature detector disposed on a rear surface side of the light receiving unit of the first optical power generation unit or the light receiving unit of the second optical power generation unit, and a heat conductor that transmits heat from the thermal contact to the resistance temperature detector.

19. The signal transmission device according to claim 17, wherein the signal transmission device is a device attached to a living body,
the predetermined direction is a direction facing a body surface of the living body, and
information of a first temperature on the first surface side detected by the first temperature sensor and information of a second temperature on the second surface side detected by the second temperature sensor are used to obtain metabolic information of the living body to which the signal transmission device is attached.

20. The signal transmission device according to claim 17, further comprising
a vibration sensor that detects vibration in the predetermined direction.

21. The signal transmission device according to claim 20, wherein the vibration sensor includes a power generation element that generates power using vibration, and the communication control unit further transmits the signal using the power generated by the power generation element.

22. The signal transmission device according to claim 20, wherein the vibration sensor includes a plate-shaped piezoelectric element, and a weight fixed to one end side of the piezoelectric element, and the vibration sensor is fixed to base material on the other end side of the piezoelectric element.

23. The signal transmission device according to claim 20, wherein the vibration sensor is disposed between the first optical power generation unit and the second optical power generation unit.

24. The signal transmission device according to claim 20, wherein the signal transmission device is a device attached to a moveable object to be managed, and
vibration information detected by the vibration sensor is used to obtain activity information of the object to be managed to which the signal transmission device is attached.

25. The signal transmission device according to claim 20, wherein the signal transmission device is a device attached to livestock,
vibration information detected by the vibration sensor is used to obtain activity information of the livestock,
information of a first temperature on the first surface side detected by the first temperature sensor and information of a second temperature on the second surface side detected by the second temperature sensor are used to obtain metabolic information of the livestock, and
the activity information and the metabolic information of the livestock are used to obtain biological information of the livestock to which the signal transmission device is attached.

26. The signal transmission device according to claim 25, wherein biological information of the livestock is information of at least one of an estrus state, a childbirth state, a death or hyposthenia state, and an injury or disease state.

27. The signal transmission device according to claim 20, wherein the object to be managed is livestock, and
vibration information detected by the vibration sensor is used to obtain activity information of the livestock,
information of a first temperature on the first surface side detected by the first temperature sensor and information of a second temperature on the second surface side detected by the second temperature sensor are used to obtain metabolic information of the livestock, and
the activity information and the metabolic information of the livestock are used to detect that the signal transmission device has fallen out of the livestock.

28. The signal transmission device according to claim 20, wherein a piece of vibration information detected at a predetermined unit time set in advance among pieces of the vibration information detected by the vibration sensor is used to obtain state information of the object to be managed to which the signal transmission device is attached.

29. The signal transmission device according to claim 17, wherein the signal transmission device includes a non-contact communication antenna for performing non-contact communication and a first antenna used in wireless communication by the communication control unit.

30. The signal transmission device according to claim 29, wherein the non-contact communication antenna is an antenna formed on a substrate, and
the non-contact communication antenna is provided on a rear surface side of the light receiving unit of the first optical power generation unit.

31. The signal transmission device according to claim 17, wherein the signal transmission device is attached to the object to be managed via a cover case, and
the cover case includes
a case main body portion that accommodates the signal transmission device such that the signal transmission device faces the predetermine direction,
a band portion that has an engaging portion on one surface and is wound around an attachment target portion,
a connection portion into which the band portion is inserted, the connection portion having a locking portion configured to be locked at the engaging portion, and
a guide portion that holds the band portion inserted into the connection portion in a predetermined posture.

* * * * *